United States Patent
Kubo et al.

(10) Patent No.: US 9,663,717 B2
(45) Date of Patent: May 30, 2017

(54) LIQUID CRYSTAL COMPOUND HAVING CYCLOHEXENE RING, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Takahiro Kubo, Ichihara (JP); Masahide Kobayashi, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 15/079,218

(22) Filed: Mar. 24, 2016

(65) Prior Publication Data
US 2016/0280997 A1    Sep. 29, 2016

(30) Foreign Application Priority Data

Mar. 25, 2015    (JP) .................. 2015-062459

(51) Int. Cl.
| | |
|---|---|
| C09K 19/30 | (2006.01) |
| C09K 19/34 | (2006.01) |
| C07C 43/225 | (2006.01) |
| C07D 319/06 | (2006.01) |
| C07D 213/65 | (2006.01) |
| C07D 239/26 | (2006.01) |
| C07D 309/06 | (2006.01) |
| C07C 69/78 | (2006.01) |
| C07D 213/30 | (2006.01) |
| C07D 239/34 | (2006.01) |
| C07C 69/75 | (2006.01) |
| C07C 69/757 | (2006.01) |
| C09K 19/04 | (2006.01) |

(52) U.S. Cl.
CPC ........ *C09K 19/3458* (2013.01); *C07C 43/225* (2013.01); *C07C 69/75* (2013.01); *C07C 69/757* (2013.01); *C07C 69/78* (2013.01); *C07D 213/30* (2013.01); *C07D 213/65* (2013.01); *C07D 239/26* (2013.01); *C07D 239/34* (2013.01); *C07D 309/06* (2013.01); *C07D 319/06* (2013.01); *C09K 19/3066* (2013.01); *C09K 19/3098* (2013.01); *C07C 2101/14* (2013.01); *C07C 2101/16* (2013.01); *C09K 2019/0466* (2013.01); *C09K 2019/301* (2013.01); *C09K 2019/304* (2013.01); *C09K 2019/3009* (2013.01); *C09K 2019/3016* (2013.01); *C09K 2019/3019* (2013.01); *C09K 2019/3021* (2013.01); *C09K 2019/3025* (2013.01); *C09K 2019/3027* (2013.01); *C09K 2019/3042* (2013.01); *C09K 2019/3077* (2013.01); *C09K 2019/3422* (2013.01); *C09K 2019/3425* (2013.01)

(58) Field of Classification Search
CPC ..................................................... C09K 19/34
See application file for complete search history.

(56) References Cited

U.S. PATENT DOCUMENTS

| | | |
|---|---|---|
| 5,728,319 A | 3/1998 | Matsui et al. |
| 6,007,740 A | 12/1999 | Andou et al. |

FOREIGN PATENT DOCUMENTS

| | | |
|---|---|---|
| JP | H-10204016 A | 8/1998 |
| WO | 96-11897 A1 | 4/1996 |

*Primary Examiner* — Chanceity Robinson
(74) *Attorney, Agent, or Firm* — Hogan Lovells US LLP

(57) ABSTRACT

A liquid crystal compound is provided that satisfies at least one physical property such as high stability to heat and light, a high clearing point, low minimum temperature of liquid crystal phase, small viscosity, suitable optical anisotropy, large dielectric anisotropy, suitable elastic constant and compatibility with other liquid crystal compounds. A liquid crystal composition containing the compound and a liquid crystal display device including the composition is also provided. The liquid crystal compound is represented by formula (1)

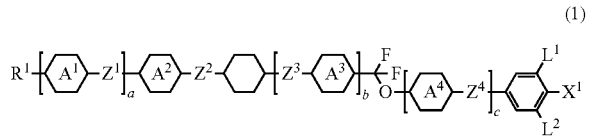

(1)

in which $R^1$ is alkyl having 1 to 10 carbons, rings $A^1$, $A^3$ and $A^4$ are independently 1,4-phenylene, ring $A^2$ is a divalent group represented by any one of formulas (Ch), (Cx) and (ch),

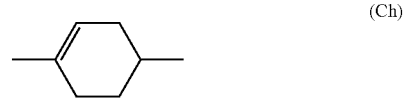

(Ch)

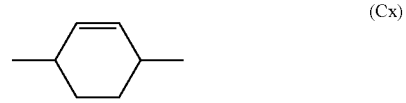

(Cx)

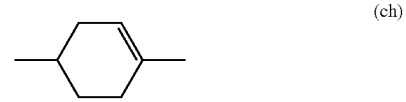

(ch)

$Z^1$, $Z^2$, $Z^3$ and $Z^4$ are a single bond, $X^1$ is fluorine, $L^1$ and $L^2$ are fluorine, a, b and c are independently 0 or 1, and a sum of a, b and c is 0 or 1.

16 Claims, No Drawings

US 9,663,717 B2

LIQUID CRYSTAL COMPOUND HAVING CYCLOHEXENE RING, LIQUID CRYSTAL COMPOSITION AND LIQUID CRYSTAL DISPLAY DEVICE

TECHNICAL FIELD

The invention relates to a liquid crystal compound, a liquid crystal composition and a liquid crystal display device. More specifically, the invention relates to a liquid crystal compound having a cyclohexene ring and a $CF_2O$ bonding group, a liquid crystal composition that contains the compound and has a nematic phase, and a liquid crystal display device including the composition.

The liquid crystal display device has been widely utilized for a display of a personal computer, a television or the like. The device utilizes physical properties such as optical anisotropy, dielectric anisotropy and so forth of the liquid crystal compound. Specific examples of an operating mode of the liquid crystal display device include a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode.

In such a liquid crystal display device, a liquid crystal composition having suitable physical properties is used. In order to further improve characteristics of the device, the liquid crystal compound contained in the composition preferably has physical properties described in (1) to (8) below: (1) a high stability to heat and light, (2) a high clearing point, (3) a low minimum temperature of the liquid crystal phase, (4) a small viscosity (η), (5) a suitable optical anisotropy (Δn), (6) a large dielectric anisotropy (Δ∈), (7) a suitable elastic constant (K) and (8) an excellent compatibility with other liquid crystal compounds.

An effect of the physical properties of the liquid crystal compound on the characteristics of the device is as described below. A compound having the high stability to heat and light as described in (1) increases a voltage holding ratio of the device. Therefore, a service life of the device becomes longer. A compound having the high clearing point as described in (2) extends a temperature range in which the device can be used. A compound having the low minimum temperature of the liquid crystal phase such as the nematic phase and a smectic phase as described in (3), in particular, a compound having the low minimum temperature of the nematic phase, also extends the temperature range in which the device can be used. A compound having the small viscosity as described in (4) shortens a response time of the device.

According to a design of the device, a compound having the suitable optical anisotropy as described in (5), more specifically, a compound having a large optical anisotropy or a small optical anisotropy is required. When the response time is shortened by decreasing a cell gap of the device, a compound having the large optical anisotropy is suitable. A compound having the large dielectric anisotropy as described in (6) decreases a threshold voltage of the device. Thus, an electric power consumption of the device is decreased. On the other hand, a compound having a small dielectric anisotropy shortens the response time of the device by decreasing viscosity of the composition. The compound extends the temperature range in which the device can be used by increasing a maximum temperature of the nematic phase.

With regard to (7), a compound having a large elastic constant decreases the response time of the device. A compound having a small elastic constant decreases the threshold voltage of the device. Therefore, the suitable elastic constant is required according to characteristics to be desirably improved. A compound having the excellent compatibility with other liquid crystal compounds as described in (8) is preferred. The reason is that the physical properties of the composition are adjusted by mixing liquid crystal compounds having different physical properties.

A variety of liquid crystal compounds having the large dielectric anisotropy have been so far prepared. A variety of liquid crystal compounds having the large optical anisotropy also have been prepared. The reason is that excellent physical properties that are not found in a conventional compound are expected from a new compound. The reason is that, when the new compound is added to the liquid crystal composition, a suitable balance regarding at least two physical properties is obtained in the composition. From such a situation, a compound having the excellent physical properties and the suitable balance has been desired with regard to the physical properties (1) to (8) described above.

CITATION LIST

Patent Literature

Patent literature No. 1: WO 1996/011897 A.
Patent literature No. 2: JP H10-204016 A.

SUMMARY OF INVENTION

Technical Problem

A first object is to provide a liquid crystal compound satisfying at least one of physical properties such as a high stability to heat and light, a high clearing point (or a high maximum temperature of a nematic phase), a low minimum temperature of a liquid crystal phase, a small viscosity, a suitable optical anisotropy, a large dielectric anisotropy, a suitable elastic constant and an excellent compatibility with other liquid crystal compounds. In particular, the object is to provide a compound having an excellent compatibility with other liquid crystal compounds. A second object is to provide a liquid crystal composition that contains the compound and satisfies at least one of physical properties such as a high stability to heat and light, a high maximum temperature of a nematic phase, a low minimum temperature of the nematic phase, a small viscosity, a suitable optical anisotropy, a large dielectric anisotropy, a large specific resistance and a suitable elastic constant. The object is to provide a liquid crystal composition having a suitable balance regarding at least two of the physical properties. A third object is to provide a liquid crystal display device including the composition and having a wide temperature range in which the device can be used, a short response time, a large voltage holding ratio, a low threshold voltage, a large contrast ratio and a long service life.

Solution to Problem

The invention concerns a compound represented by formula (1), a liquid crystal composition containing the compound, and a liquid crystal display device including the composition:

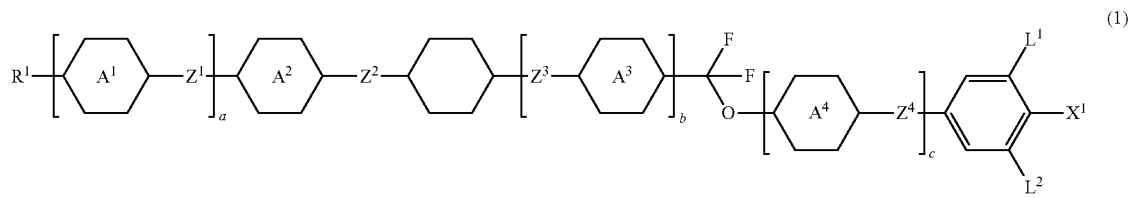

wherein, in formula (1),

R¹ is hydrogen, fluorine, chlorine or alkyl having 1 to 10 carbons, and in R¹, at least one piece of —CH₂— may be replaced by —O—, at least one piece of —CH₂CH₂— may be replaced by —CH=CH—, and at least one piece of hydrogen may be replaced by fluorine;

ring A¹, ring A³ and ring A⁴ are independently 1,4-cyclohexylene, 1,4-phenylene, 1,4-phenylene in which at least one piece of hydrogen is replaced by fluorine, tetrahydropyran-2,5-diyl, 1,3-dioxane-2,5-diyl, pyridine-2,5-diyl or pyrimidine-2,5-diyl, and ring A² is a divalent group represented by any one of formula (Ch), formula (Cx) and formula (ch);

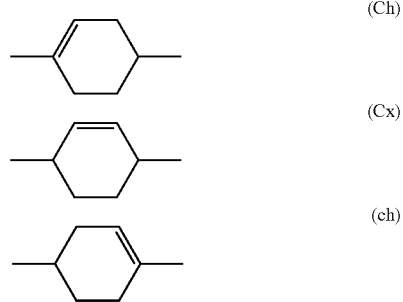

wherein, Z¹, Z², Z³ and Z⁴ are independently a single bond, —COO—, —OCH₂—, —CF₂O—, —CH₂CH₂—, —CH=CH—, —CF₂CF₂—, —CF=CF—, —(CH₂)₄— or —CH₂CH=CHCH₂—;

X¹ is hydrogen, fluorine, —CF₃ or —OCF₃;

L¹ and L² are independently hydrogen or fluorine; and a, b and c are independently 0 or 1, and a sum of a, b and c is 0 or 1.

Advantageous Effects of Invention

A first advantage is to provide a liquid crystal compound satisfying at least one of physical properties such as a high stability to heat and light, a high clearing point (or a high maximum temperature of a nematic phase), a low minimum temperature of a liquid crystal phase, a small viscosity, a suitable optical anisotropy, a large dielectric anisotropy, a suitable elastic constant and an excellent compatibility with other liquid crystal compounds. The compound has a larger dielectric anisotropy and a superb compatibility in comparison with a similar compound (see Comparative Examples 1 and 2). A second advantage is to provide a liquid crystal composition that contains the compound and satisfies at least one of physical properties such as a high stability to heat and light, a high maximum temperature of a nematic phase, a low minimum temperature of the nematic phase, a small viscosity, a suitable optical anisotropy, a large dielectric anisotropy, a large specific resistance and a suitable elastic constant. The advantage is to provide a liquid crystal composition having a suitable balance regarding at least two of the physical properties. A third advantage is to provide a liquid crystal display device including the composition and having a wide temperature range in which the device can be used, a short response time, a large voltage holding ratio, a low threshold voltage, a large contrast ratio and a long service life.

DESCRIPTION OF EMBODIMENTS

Usage of terms herein is as described below. Terms "liquid crystal compound," "liquid crystal composition" and "liquid crystal display device" may be occasionally abbreviated as "compound," "composition" and "device," respectively. "Liquid crystal compound" is a generic term for a compound having a liquid crystal phase such as a nematic phase and a smectic phase, and a compound having no liquid crystal phase but being added for the purpose of adjusting physical properties of the composition, such as a maximum temperature, a minimum temperature, viscosity and dielectric anisotropy. The compound has a six-membered ring such as 1,4-cyclohexylene and 1,4-phenylene, and rod-like molecular structure. "Liquid crystal display device" is a generic term for a liquid crystal display panel and a liquid crystal display module. "Polymerizable compound" includes a compound to be added to the composition for the purpose of forming a polymer in the composition.

The liquid crystal composition is prepared by mixing a plurality of liquid crystal compounds. A proportion (content) of the liquid crystal compounds is expressed in terms of weight percent (% by weight) based on the weight of the liquid crystal composition. An additive such as a polymerizable compound, a polymerization initiator, a polymerization inhibitor, an optically active compound, an antioxidant, an ultraviolet light absorber, a light stabilizer, a heat stabilizer, a dye and an antifoaming agent is added to the composition, when necessary. A proportion of the additive (amount of addition) is expressed in terms of weight percent (% by weight) based on the weight of the liquid crystal composition in a manner similar to the proportion of the liquid crystal compounds. Weight parts per million (ppm) may be occasionally used. A proportion of the polymerization initiator or the polymerization inhibitor is exceptionally expressed based on the weight of the polymerizable compound.

"Clearing point" is a transition temperature between the liquid crystal phase and an isotropic phase in the liquid crystal compound. "Minimum temperature of the liquid crystal phase" is a transition temperature between a solid and the liquid crystal phase (the smectic phase, the nematic phase or the like) in the liquid crystal compound. "Maximum temperature of the nematic phase" is a transition temperature between the nematic phase and the isotropic phase in a mixture of the liquid crystal compound and a base liquid crystal or in the liquid crystal composition, and may be occasionally abbreviated as the maximum temperature. "Lower limit of the temperature range of the nematic phase" may be occasionally abbreviated as "minimum temperature." An expression "to increase the dielectric anisotropy" means that a value thereof positively increases for the composition having a positive dielectric anisotropy, and that the value negatively increases for the composition having a negative dielectric anisotropy.

A compound represented by formula (1) may be occasionally abbreviated as "compound (1)." At least one compound selected from the group of compounds represented by formula (1) may be occasionally abbreviated as "compound (1)." "Compound (1)" means one compound represented by formula (1), a mixture of two compounds or a mixture of three or more compounds represented by formula (1). A same rule also applies to any other compound represented by any other formula. In formulas (1) to (15), a symbol such as $A^1$, $B^1$, $C^1$ or the like surrounded by a hexagonal shape corresponds to ring $A^1$, ring $B^1$, ring $C^1$ or the like, respectively. The hexagonal shape means a six-membered ring such as cyclohexane and benzene. The hexagonal shape may occasionally mean a condensed ring such as naphthalene or a bridged ring such as adamantane.

A symbol of terminal group $R^1$ is used for a plurality of compounds in chemical formulas of component compounds. In the compounds, two groups represented by two pieces of arbitrary $R^1$ may be identical or different. In one case, for example, $R^1$ of compound (1-1) is ethyl and $R^1$ of compound (1-2) is ethyl. In another case, $R^1$ of compound (1-1) is ethyl and $R^1$ of compound (1-2) is propyl. A same rule also applies to a symbol such as $R^{11}$ and $Z^{11}$. In compound (8), when i is 2, two rings $D^1$ exist. In the compound, two groups represented by two rings $D^1$ may be identical or different. A same rule also applies to two of arbitrary rings $D^1$ when i is larger than 2. A same rule also applies to any other symbol.

An expression "at least one piece of 'A'" means that the number of 'A' is arbitrary. An expression "at least one piece of 'A' may be replaced by 'B'" means that, when the number of 'A' is 1, a position of 'A' is arbitrary, and when the number of 'A' is 2 or more, positions thereof can be selected without restriction. A same rule also applies to an expression "at least one piece of 'A' is replaced by 'B'." An expression "at least one piece of 'A' may be replaced by 'B', 'C' or" includes a case where arbitrary 'A' is replaced by 'B', a case where arbitrary 'A' is replaced by 'C', and a case where arbitrary 'A' is replaced by 'D', and also a case where plural pieces of 'A' are replaced by at least two pieces of 'B', 'C' and/or 'D'. For example, "alkyl in which at least one piece of —$CH_2$— may be replaced by —O— or —CH=CH—" includes alkyl, alkoxy, alkoxyalkyl, alkenyl, alkoxyalkenyl and alkenyloxyalkyl. In addition, a case where replacement of two successive —$CH_2$— by —O— results in forming —O—O— is not preferred. In the alkyl or the like, a case where replacement of —$CH_2$— of a methyl part (—$CH_2$—H) by —O— results in forming —O—H is not preferred, either.

Halogen means fluorine, chlorine, bromine and iodine. Preferred halogen is fluorine and chlorine. Further preferred halogen is fluorine. Alkyl of the liquid crystal compound is straight-chain alkyl or branched-chain alkyl, but includes no cyclic alkyl. Straight-chain alkyl is generally preferred to branched-chain alkyl. A same rule also applies to a terminal group such as alkoxy and alkenyl. With regard to a configuration of 1,4-cyclohexylene, trans is preferred to cis for increasing the maximum temperature. Then, 2-fluoro-1,4-phenylene means two divalent groups described below. In a chemical formula thereof, fluorine may be leftward (L) or rightward (R). A same rule also applies to an asymmetrical divalent group formed by eliminating two pieces of hydrogen from a ring, such as tetrahydropyran-2,5-diyl.

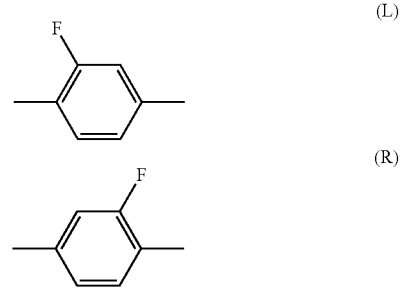

The invention includes items described below.
Item 1. A compound represented by formula (1):

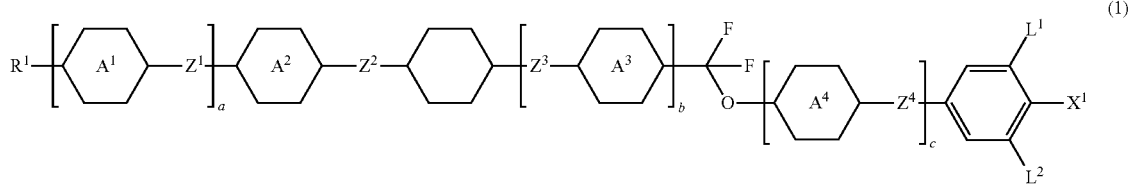

wherein, in formula (1), $R^1$ is hydrogen, fluorine, chlorine or alkyl having 1 to 10 carbons, and in $R^1$, at least one piece of —$CH_2$— may be replaced by —O—, at least one piece of —$CH_2CH_2$— may be replaced by —CH=CH—, and at least one piece of hydrogen may be replaced by fluorine;

ring $A^1$, ring $A^3$ and ring $A^4$ are independently 1,4-cyclohexylene, 1,4-phenylene, 1,4-phenylene in which at least one piece of hydrogen is replaced by fluorine, tetrahydropyran-2,5-diyl, 1,3-dioxane-2,5-diyl, pyridine-2,5-diyl or pyrimidine-2,5-diyl, and ring $A^2$ is a divalent group represented by any one of formula (Ch), formula (Cx) and formula (ch);

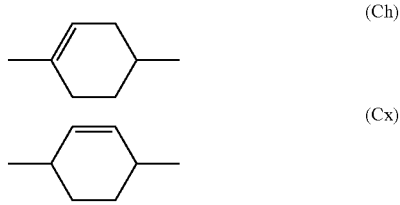

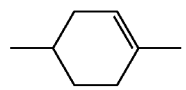 (ch)

wherein, $Z^1$, $Z^2$, $Z^3$ and $Z^4$ are independently a single bond, —COO—, —OCH$_2$—, —CF$_2$O—, —CH$_2$CH$_2$—, —CH=CH—, —CF$_2$CF$_2$—, —CF=CF—, —(CH$_2$)$_4$— or —CH$_2$CH=CHCH$_2$—;

$X^1$ is hydrogen, fluorine, —CF$_3$ or —OCF$_3$;

$L^1$ and $L^2$ are independently hydrogen or fluorine; and a, b and c are independently 0 or 1, and a sum of a, b and c is 0 or 1.

Item 2. The compound according to item 1, wherein, in formula (1) described in item 1, $R^1$ is alkyl having 1 to 10 carbons, and in at least one piece of —CH$_2$— may be replaced by —O—, at least one piece of —CH$_2$CH$_2$— may be replaced by —CH=CH—, and at least one piece of hydrogen may be replaced by fluorine;

ring $A^1$, $A^3$ and $A^4$ are independently 1,4-cyclohexylene, 1,4-phenylene, 1,4-phenylene in which at least one piece of hydrogen is replaced by fluorine, tetrahydropyran-2,5-diyl or 1,3-dioxane-2,5-diyl, and ring $A^2$ is a divalent group represented by any one of formula (Ch), formula (Cx) and formula (ch);

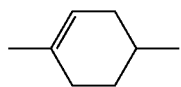 (Ch)

 (Cx)

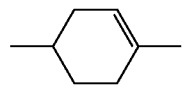 (ch)

wherein, $Z^1$, $Z^2$, $Z^3$ and $Z^4$ are independently a single bond, —COO—, —OCH$_2$—, —CF$_2$O—, —CH$_2$CH$_2$—, —CH=CH— or —C≡C—;

$X^1$ is hydrogen, fluorine, —CF$_3$ or —OCF$_3$;

$L^1$ and $L^2$ are independently hydrogen or fluorine; and a, b and c are independently 0 or 1, and a sum of a, b and c is 0 or 1.

Item 3. The compound according to item 1 or 2, represented by any one of formula (1-1), formula (1-2), formula (1-3) and formula (1-4):

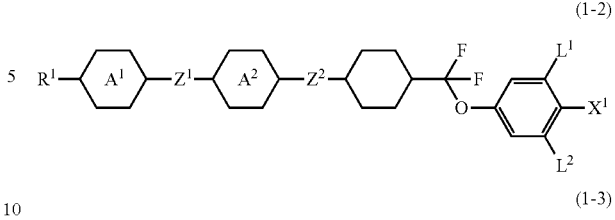

wherein, in formula (1-1) to formula (1-4), $R^1$ is alkyl having 1 to 10 carbons, alkoxy having 1 to 10 carbons, alkenyl having 2 to 10 carbons or alkenyloxy having 2 to 10 carbons;

ring $A^1$, ring $A^3$ and ring $A^4$ are independently 1,4-cyclohexylene, 1,4-phenylene, or 1,4-phenylene in which at least one piece of hydrogen is replaced by fluorine, and ring $A^2$ is a divalent group represented by any one of formula (Ch), formula (Cx) and formula (ch);

wherein, $Z^1$, $Z^2$, $Z^3$ and $Z^4$ are independently a single bond, —COO—, —OCH$_2$—, —CF$_2$O—, —CH$_2$CH$_2$—, —CH=CH— or —C≡C—;

$X^1$ is fluorine, —CF$_3$ or —OCF$_3$; and $L^1$ and $L^2$ are independently hydrogen or fluorine.

Item 4. The compound according to any one of items 1 to 3, wherein, in formula (1-1), formula (1-2), formula (1-3) and formula (1-4) described in item 3, $R^1$ is alkyl having 1 to 10 carbons, alkoxy having 1 to 10 carbons, alkenyl having 2 to 10 carbons or alkenyloxy having 2 to 10 carbons;

ring $A^1$, ring $A^3$ and ring $A^4$ are independently 1,4-cyclohexylene, 1,4-phenylene, or 1,4-phenylene in which one or two pieces of hydrogen are replaced by fluorine, and ring $A^2$ is a divalent group represented by any one of formula (Ch), formula (Cx) and formula (ch);

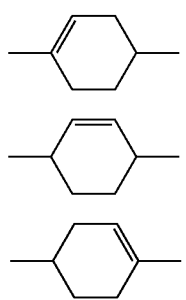

(Ch)

(Cx)

(ch)

wherein, $Z^1$, $Z^2$, $Z^3$ and $Z^4$ are independently a single bond, —COO—, —OCH$_2$—, —CF$_2$O— or —CH$_2$CH$_2$—;

$X^1$ is fluorine, —CF$_3$ or —OCF$_3$; and $L^1$ is fluorine, and $L^2$ is hydrogen or fluorine.

Item 5. The compound according to any one of items 1 to 4, represented by any one of formula (1-3a), formula (1-3b) and formula (1-3c):

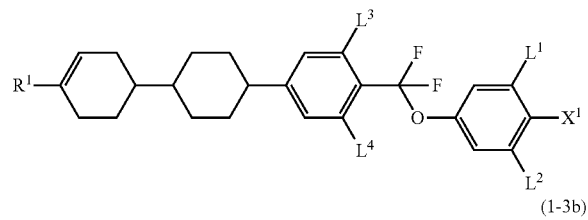

(1-3a)

(1-3b)

(1-3c)

wherein, in formula (1-3a), formula (1-3b) and formula (1-3c), $R^1$ is alkyl having 1 to 10 carbons, alkoxy having 1 to 10 carbons, alkenyl having 2 to 10 carbons or alkenyloxy having 2 to 10 carbons; $X^1$ is fluorine, —CF$_3$ or —OCF$_3$; and $L^1$, $L^2$, $L^3$ and $L^4$ are independently hydrogen or fluorine.

Item 6. The compound according to any one of items 1 to 5, wherein, in formula (1-3a), formula (1-3b) and formula (1-3c) described in item 5, $L^1$, $L^2$, $L^3$ and $L^4$ are independently hydrogen or fluorine, and at least two pieces of $L^1$, $L^2$, $L^3$ and $L^4$ are fluorine.

Item 7. The compound according to any one of items 1 to 4, represented by any one of formula (1-2a), formula (1-2b) and formula (1-2c):

(1-2a)

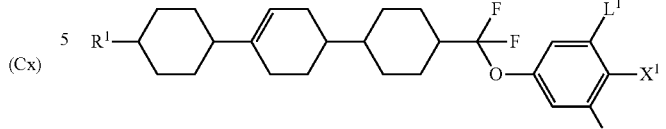

(1-2b)

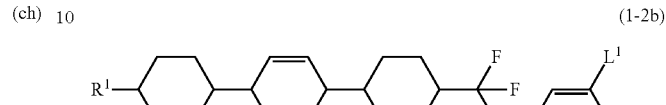

(1-2c)

wherein, in formula (1-2a), formula (1-2b) and formula (1-2c), $R^1$ is alkyl having 1 to 10 carbons, alkoxy having 1 to 10 carbons, alkenyl having 2 to 10 carbons or alkenyloxy having 2 to 10 carbons; $X^1$ is fluorine, —CF$_3$ or —OCF$_3$; and $L^1$ and $L^2$ are independently hydrogen or fluorine.

Item 8. The compound according to any one of items 1 to 4, represented by any one of formula (1-2d), formula (1-2e) and formula (1-2f):

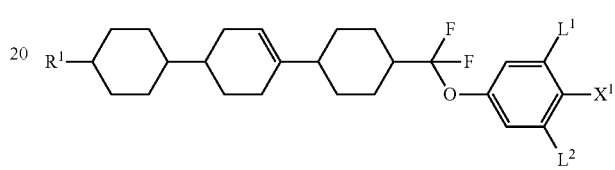

(1-2d)

(1-2e)

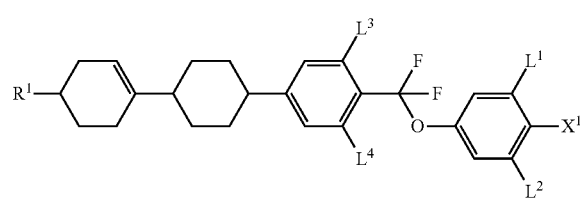

(1-2f)

wherein, in formula (1-2d), formula (1-2e) and formula (1-2f), $R^1$ is alkyl having 1 to 10 carbons, alkoxy having 1 to 10 carbons, alkenyl having 2 to 10 carbons or alkenyloxy having 2 to 10 carbons; $X^1$ is fluorine, —$CF_3$ or —$OCF_3$; and $L^1$, $L^2$, $L^3$ and $L^4$ are independently hydrogen or fluorine.

Item 9. The compound according to any one of items 1 to 4, represented by any one of formula (1-1a), formula (1-1b) and formula (1-1c):

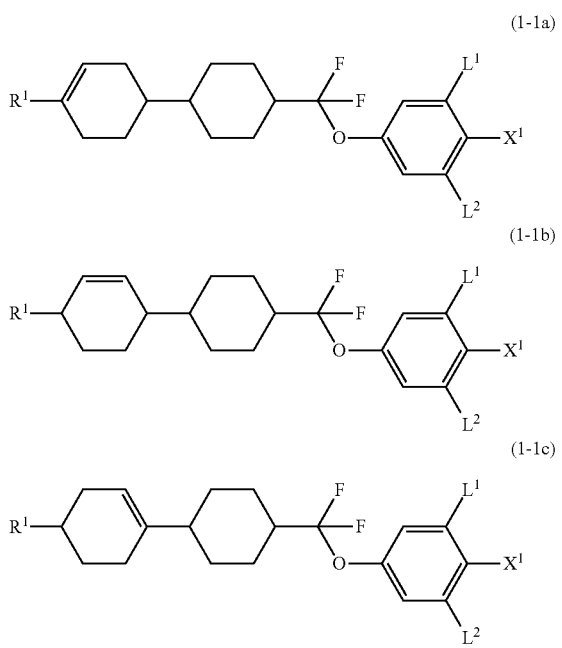

wherein, in formula (1-1a), formula (1-1b) and formula (1-1c), $R^1$ is alkyl having 1 to 10 carbons, alkoxy having 1 to 10 carbons, alkenyl having 2 to 10 carbons or alkenyloxy having 2 to 10 carbons; $X^1$ is fluorine, —$CF_3$ or —$OCF_3$; and $L^1$ and $L^2$ are independently hydrogen or fluorine.

Item 10. A liquid crystal composition, containing at least one compound according to any one of items 1 to 9.

Item 11. The liquid crystal composition according to item 10, further containing at least one compound selected from the group of compounds represented by formulas (2) to (4):

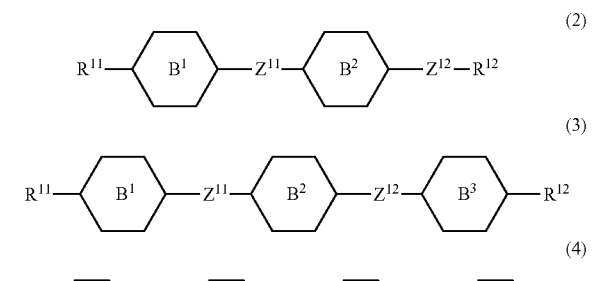

wherein, in formulas (2) to (4), $R^{11}$ and $R^{12}$ are independently alkyl having 1 to 10 carbons or alkenyl having 2 to 10 carbons, and in $R^{11}$ and $R^{12}$, at least one piece of —$CH_2$— may be replaced by —O—, and at least one piece of hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —$CH_2CH_2$—, —CH=CH—, —C≡C— or —COO—.

Item 12. The liquid crystal composition according to item 10 or 11, further containing at least one compound selected from the group of compounds represented by formulas (5) to (7):

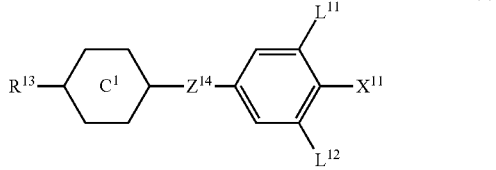

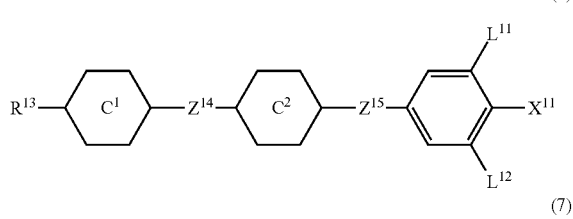

wherein, in formulas (5) to (7), $R^{13}$ is alkyl having 1 to 10 carbons or alkenyl having 2 to 10 carbons, and in $R^{13}$, at least one piece of —$CH_2$— may be replaced by —O—, and at least one piece of hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $C^1$, ring $C^2$ and ring $C^3$ are independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or $(CH_2)_4$; and $L^{11}$ and $L^{12}$ are independently hydrogen or fluorine.

Item 13. The liquid crystal composition according to any one of items 10 to 12, further containing at least one compound selected from the group of compounds represented by formula (8):

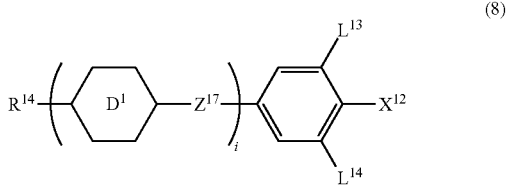

wherein, in formula (8), $R^{14}$ is alkyl having 1 to 10 carbons or alkenyl having 2 to 10 carbons, and in $R^{14}$, at least one piece of —$CH_2$— may be replaced by —O—, and at least one piece of hydrogen may be replaced by fluorine;

$X^{12}$ is —C≡N or —C≡C—C≡N;

ring $D^1$ is independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl, and when a plurality of rings $D^1$ exist, rings $D^1$ may be identical or different;

$Z^{17}$ is independently a single bond, —$CH_2CH_2$—, —C≡C—, —COO—, —$CF_2O$—, —$OCF_2$— or —$CH_2O$—, and when a plurality of $Z^{17}$ exist, $Z^{17}$ may be identical or different;

$L^{13}$ and $L^{14}$ are independently hydrogen or fluorine; and i is 1, 2, 3 or 4.

Item 14. The liquid crystal composition according to any one of items 10 to 13, further containing at least one compound selected from the group of compounds represented by formulas (9) to (15):

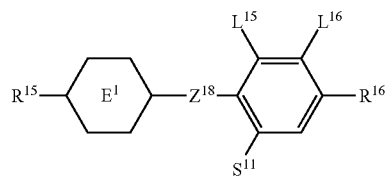
(9)

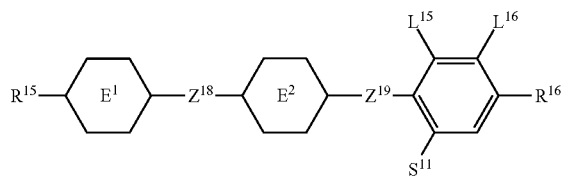
(10)

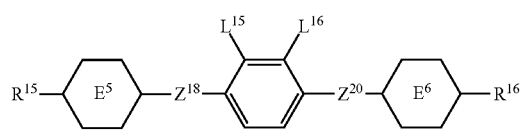
(11)

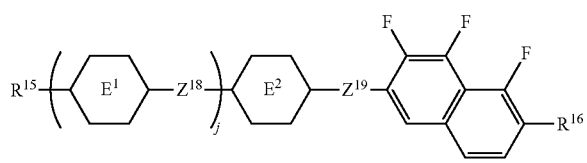
(12)

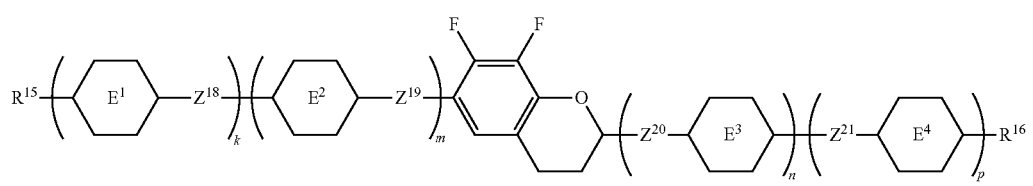
(13)

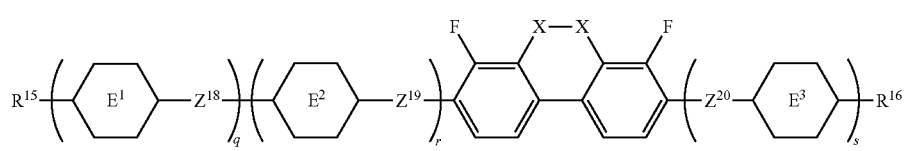
(14)

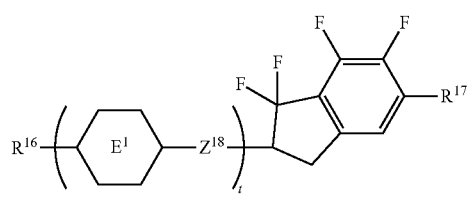
(15)

wherein, in formulas (9) to (15), $R^{15}$ and $R^{16}$ are independently alkyl having 1 to 10 carbons or alkenyl having 2 to 10 carbons, and in $R^{15}$ or $R^{16}$, at least one piece of —$CH_2$— may be replaced by —O—, and at least one piece of hydrogen may be replaced by fluorine;

$R^{17}$ is hydrogen, fluorine, alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

ring $E^1$, ring $E^2$, ring $E^3$ and ring $E^4$ are independently 1,4-cyclohexylene, 1,4-cyclohexenylene, 1,4-phenylene in which at least one piece of hydrogen may be replaced by fluorine, tetrahydropyran-2,5-diyl or decahydronaphthalene-2,6-diyl, and when a plurality of ring $E^1$, ring $E^2$, ring $E^3$ and ring $E^4$ exist, ring $E^1$, ring $E^2$, ring $E^3$ and ring $E^4$ may be identical or different;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —$CH_2CH_2$—, —COO—, —$CH_2O$—, —$OCF_2$— or —$OCF_2CH_2CH_2$—, and when a plurality of $Z^{18}$, $Z^{19}$, $Z^{20}$ and $Z^{21}$ exist, $Z^{18}$, $Z^{19}$, $Z^{20}$ and $Z^{21}$ may be identical or different;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3, and t is 1, 2 or 3.

Item 15. The liquid crystal composition according to any one of items 10 to 14, further containing at least one additive selected from the group of a polymerizable compound, a polymerization initiator, a polymerization inhibitor, an optically active compound, an antioxidant, an ultraviolet light absorber, a light stabilizer, a heat stabilizer, a dye and an antifoaming agent.

Item 16. A liquid crystal display device, including the liquid crystal composition according to any one of items 10 to 15.

The invention further includes the following items: (a) the composition, further containing one, two or at least three additives selected from the group of a polymerizable compound, a polymerization initiator, a polymerization inhibitor, an optically active compound, an antioxidant, an ultraviolet light absorber, a light stabilizer, a heat stabilizer, a dye and an antifoaming agent; (b) the liquid crystal composition, wherein a maximum temperature of a nematic phase is 70° C. or more, an optical anisotropy at a wavelength of 589 nanometers (measured at 25° C.) is 0.07 or more, and a dielectric anisotropy at a frequency of 1 kHz (measured at 25° C.) is 2 or more; and (c) the liquid crystal display device, wherein an operating mode in the liquid crystal display device is a TN mode, an ECB mode, an OCB mode, an IPS mode or an FPA mode, and a driving mode in the liquid crystal display device is an active matrix (AM) mode.

An aspect of compound (1), a method for preparing compound (1), the liquid crystal composition and the liquid crystal display device will be described in the order.

1. Aspect of compound (1)

Compound (1) has a feature of having a cyclohexene ring and a $CF_2O$ bonding group. Compound (1) has a larger dielectric anisotropy and a superb compatibility in comparison with a similar compound (see Comparative Examples 1 and 2). Preferred examples of compound (1) are described. Preferred examples of terminal group $R^1$ and $X^1$, ring $A^1$ to ring $A^4$, bonding groups $Z^1$ to $Z^4$ and substituents $L^1$ to $L^4$ in compound (1) are also applied to a subordinate formula of formula (1) for compound (1). In compound (1), physical properties can be arbitrarily adjusted by suitably combining the groups. Compound (1) may contain an isotope such as $^2H$ (deuterium) and $^{13}C$ in an amount larger than an amount of natural abundance because no significant difference exists in the physical properties of the compound. In addition, symbols in compound (1) are defined as described in item 1.

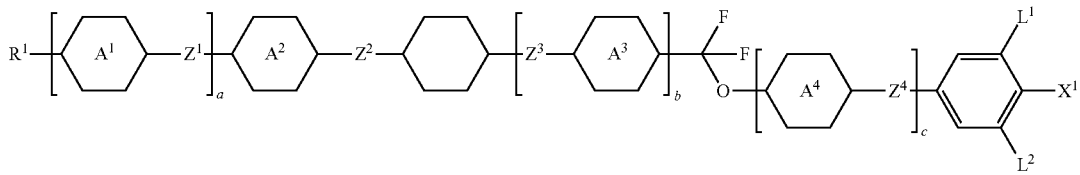

(1)

In formula (1), $R^1$ is hydrogen, fluorine, chlorine or alkyl having 1 to 10 carbons, and in the alkyl, at least one piece of —$CH_2$— may be replaced by —O—, at least one piece of —$CH_2CH_2$— may be replaced by —CH═CH—, and in the monovalent groups, at least one piece of hydrogen may be replaced by fluorine.

Specific examples of $R^1$ include hydrogen, fluorine, chlorine, alkyl, alkoxy, alkoxyalkyl, alkoxyalkoxy, alkenyl, alkenyloxy, alkenyloxyalkyl and alkoxyalkenyl. Preferred examples of $R^1$ include alkyl, alkoxy, alkoxyalkyl, alkoxyalkenyl, alkenyl, alkenyloxy, alkenyloxyalkyl and alkoxyalkenyl. Further preferred examples of $R^1$ include alkyl, alkoxy, alkoxyalkyl, alkenyl and alkenyloxy. Still further preferred examples of $R^1$ also include alkyl, alkoxy, alkenyl and alkenyloxy. Particularly preferred examples of $R^1$ include alkyl and alkenyl. Most preferred examples of $R^1$ include alkyl.

Preferred examples of alkyl include —$CH_3$, —$C_2H_5$, —$C_3H_7$, —$C_5H_{11}$, —$C_6H_{13}$ and —$C_7H_{15}$.

Preferred examples of alkoxy include —$OCH_3$, —$OC_2H_5$, —$OC_3H_7$, —$OC_4H_9$, —$OC_5H_{11}$, —$OC_6H_{13}$ and —$OC_7H_{15}$.

Preferred examples of alkoxyalkyl include —$CH_2OCH_3$, —$CH_2OC_2H_5$, —$CH_2OC_3H_7$, —$(CH_2)_2$—$OCH_3$, —$(CH_2)_2$—$OC_2H_5$, —$(CH_2)_2$—$OC_3H_7$, —$(CH_2)_3$—$OCH_3$, —$(CH_2)_4$—$OCH_3$ or —$(CH_2)_5$—$OCH_3$.

Preferred examples of alkenyl include —CH═$CH_2$, —CH═$CHCH_3$, —$CH_2$CH═$CH_2$, —CH═$CHC_2H_5$, —$CH_2$CH═$CHCH_3$, —$(CH_2)_2$—CH═$CH_2$, —CH═$CHC_3H_7$, —$CH_2$CH═$CHC_2H_5$, —$(CH_2)_2$—CH═$CHCH_3$ and —$(CH_2)_3$—CH═$CH_2$.

Preferred examples of alkenyloxy include —$OCH_2$CH═$CH_2$, —$OCH_2$CH═$CHCH_3$ and —$OCH_2$CH═$CHC_2H_5$.

Preferred examples of $R^1$ include hydrogen, —$CH_3$, —$C_2H_5$, —$C_3H_7$, —$C_4H_9$, —$C_5H_{11}$, —$C_6H_{13}$, —$OCH_3$, —$OC_2H_5$, —$OC_3H_7$, —$OC_4H_9$, —$OC_5H_{11}$, —$CH_2OCH_3$, —$CH$=$CH_2$, —$CH$=$CHCH_3$, —$(CH_2)_2$—$CH$=$CH_2$, —$CH_2CH$=$CHC_2H_5$, —$(CH_2)_2$—$CH$=$CHCH_3$, —$OCH_2CH$=$CH_2$, —$OCH_2CH$=$CHCH_3$ and —$OCH_2CH$=$CHC_2H_5$. Further preferred examples of $R^1$ include —$C_3H_7$, —$C_4H_9$, —$C_5H_{11}$, —$C_6H_{13}$, —$(CH_2)_2$—$CH$=$CH$ and —$(CH_2)_2$—$CH$=$CHCH_3$ When $R^1$ has a straight chain, compound (1) has a wide temperature range of the liquid crystal phase and a small viscosity. When $R^1$ has a branched chain, compound (1) has a good compatibility with other liquid crystal compounds. A compound in which $R^1$ is optically active is useful as a chiral dopant. A reverse twisted domain to be generated in the liquid crystal display device can be prevented by adding the compound to the composition. A compound in which $R^1$ is not optically active is useful as a component of the composition. When $R^1$ is alkenyl, a preferred configuration depends on a position of a double bond. An alkenyl compound having the preferred configuration has the small viscosity, the high maximum temperature or the wide temperature range of the liquid crystal phase.

A preferred configuration of —$CH$=$CH$— in the alkenyl depends on a position of a double bond. In alkenyl having the double bond in an odd-numbered position, such as —$CH$=$CHCH_3$, —$CH$=$CHC_2H_5$, —$CH$=$CHC_3H_7$, —$CH$=$CHC_4H_9$, —$C_2H_4CH$=$CHCH_3$ and —$C_2H_4CH$=$CHC_2H_5$, a trans configuration is preferred. In alkenyl having the double bond in an even-numbered position, such as —$CH_2CH$=$CHCH_3$, —$CH_2CH$=$CHC_2H_5$ and —$CH_2CH$=$CHC_3H_7$, a cis configuration is preferred. An alkenyl compound having the preferred configuration has a high clearing point or a wide temperature range of the liquid crystal phase. A detailed description is found in Mol. Cryst. Liq. Cryst., 1985, 131, 109 and Mol. Cryst. Liq. Cryst., 1985, 131 and 327.

In formula (1), ring $A^1$, ring $A^3$ and ring $A^4$ are independently 1,4-cyclohexylene, 1,4-phenylene, 1,4-phenylene in which at least one piece of hydrogen is replaced by fluorine, tetrahydropyran-2,5-diyl, 1,3-dioxane-2,5-diyl, pyridine-2,5-diyl or pyrimidine-2,5-diyl, and ring $A^2$ is a divalent group represented by any one of formula (Ch), formula (Cx) and formula (ch).

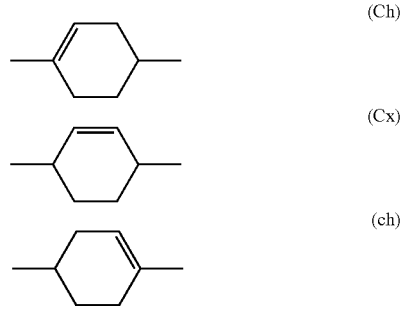

Preferred examples of ring $A^1$, ring $A^3$ or ring $A^4$ include 1,4-cyclohexylene, 1,4-phenylene, 2-fluoro-1,4-phenylene, 2,3-difluoro-1,4-phenylene, 2,6-difluoro-1,4-phenylene, 2,3,5-trifluoro-1,4-phenylene, tetrahydropyran-2,5-diyl, 1,3-dioxane-2,5-diyl or pyrimidine-2,5-diyl. Further preferred examples of ring $A^1$, ring $A^3$ or ring $A^4$ include 1,4-cyclohexylene, 1,4-phenylene, 2-fluoro-1,4-phenylene, 2,6-difluoro-1,4-phenylene or tetrahydropyran-2,5-diyl. Particularly preferred examples of ring $A^1$, ring $A^3$ or ring $A^4$ include 1,4-cyclohexylene, 1,4-phenylene, 2-fluoro-1,4-phenylene or 2,6-difluoro-1,4-phenylene.

When ring $A^1$, ring $A^3$ or ring $A^4$ is 1,4-cyclohexylene, compound (1) has a high clearing point and a small viscosity. When ring $A^1$, ring $A^3$ or ring $A^4$ is 1,4-phenylene, or 1,4-phenylene in which at least one piece of hydrogen is replaced by fluorine, compound (1) has a large optical anisotropy and a comparatively large orientational order parameter. When ring $A^1$, ring $A^3$ or ring $A^4$ is 1,4-phenylene in which at least one piece of hydrogen is replaced by fluorine, compound (1) has a large dielectric anisotropy.

In formula (1), $Z^1$, $Z^2$, $Z^3$ and $Z^4$ are independently a single bond, —COO—, —$OCH_2$—, —$CF_2O$—, —$CH_2CH_2$—, —$CH$=$CH$—, —$C$≡$C$—, —$CF_2CF_2$—, —$CF$=$CF$—, —$(CH_2)_4$— or —$CH_2CH$=$CHCH_2$—.

Preferred examples of $Z^1$, $Z^2$, $Z^3$ or $Z^4$ include a single bond, —COO—, —$OCH_2$—, —$CF_2O$—, —$CH_2CH_2$—, —$CH$=$CH$—, —$CF_2CF_2$— or —$CF$=$CF$—. Further preferred examples include a single bond, —COO—, —$OCH_2$—, —$CF_2O$—, —$CH_2CH_2$— or —$CH$=$CH$—. Particularly preferred examples include a single bond, —COO— or —$CH_2CH_2$—. Most preferred examples include a single bond.

When $Z^1$, $Z^2$, $Z^3$ or $Z^4$ is a single bond, compound (1) has a high chemical stability and a small viscosity. When $Z^1$, $Z^2$, $Z^3$ or $Z^4$ is —$CF_2O$—, compound (1) has a small viscosity, a large dielectric anisotropy and a high maximum temperature.

In formula (1), $X^1$ is hydrogen, fluorine, —$CF_3$ or —$OCF_3$. Preferred $X^1$ is fluorine, —$CF_3$ or —$OCF_3$. Further preferred $X^1$ is fluorine or —$OCF_3$. Particularly preferred $X^1$ is fluorine. When $X^1$ is fluorine, compound (1) has a small viscosity. When $X^1$ is —$CF_3$, compound (1) has a large dielectric anisotropy. When $X^1$ is —$OCF_3$, compound (1) has an excellent compatibility with other liquid crystal compounds.

In formula (1), $L^1$ and $L^2$ are independently hydrogen or fluorine. Preferred $L^1$ and $L^2$ are a combination of hydrogen and fluorine. Preferred $L^1$ and $L^2$ are a combination of fluorine and fluorine. When $L^1$ and $L^2$ are the combination of hydrogen and fluorine, compound (1) has a large dielectric anisotropy. When $L^1$ and $L^2$ are the combination of fluorine and fluorine, compound (1) has a particularly large dielectric anisotropy.

In formula (1), a, b and c are independently 0 or 1, and a sum of a, b and c is 0 or 1. When the sum is 0, compound (1) has a tricycle. The compound has a small viscosity. When the sum is 1, compound (1) has a tetracycle. The compound has a high clearing point.

Preferred examples of compound (1) include compounds (1-1) to (1-4) described in item 3. Compound (1-1) is preferred from a viewpoint of a low minimum temperature. Compound (1-2) is preferred from a viewpoint of a high maximum temperature. Compound (1-3) is preferred from a viewpoint of a large dielectric anisotropy and a comparatively low viscosity. Compound (1-4) is preferred from a viewpoint of an excellent compatibility. In the compounds, compound (1-3) is further preferred from a viewpoint of a suitable balance regarding the physical properties. Further preferred examples of compounds (1-1) to (1-4) are described in items 5 to 8.

2. Synthesis of Compound (1)

A method for synthesizing compound (1) is described. Compound (1) can be prepared by suitably combining methods in synthetic organic chemistry. Methods for introducing an objective terminal group, ring and bonding group into a starting material are described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course (Shin Jikken Kagaku Koza in Japanese)" (Maruzen Co., Ltd.).

2-1. Formation of Bonding Group Z

First, schemes are shown with regard to a method for forming bonding groups $Z^1$ to $Z^3$. Next, reactions described in the schemes in methods (1) to (11) are described. In the schemes, $MSG^1$ (or $MSG^2$) is a monovalent organic group having at least one ring. The monovalent organic groups represented by a plurality of $MSG^1$ (or $MSG^2$) may be identical or different. Compounds (1A) to (1J) correspond to compound (1).

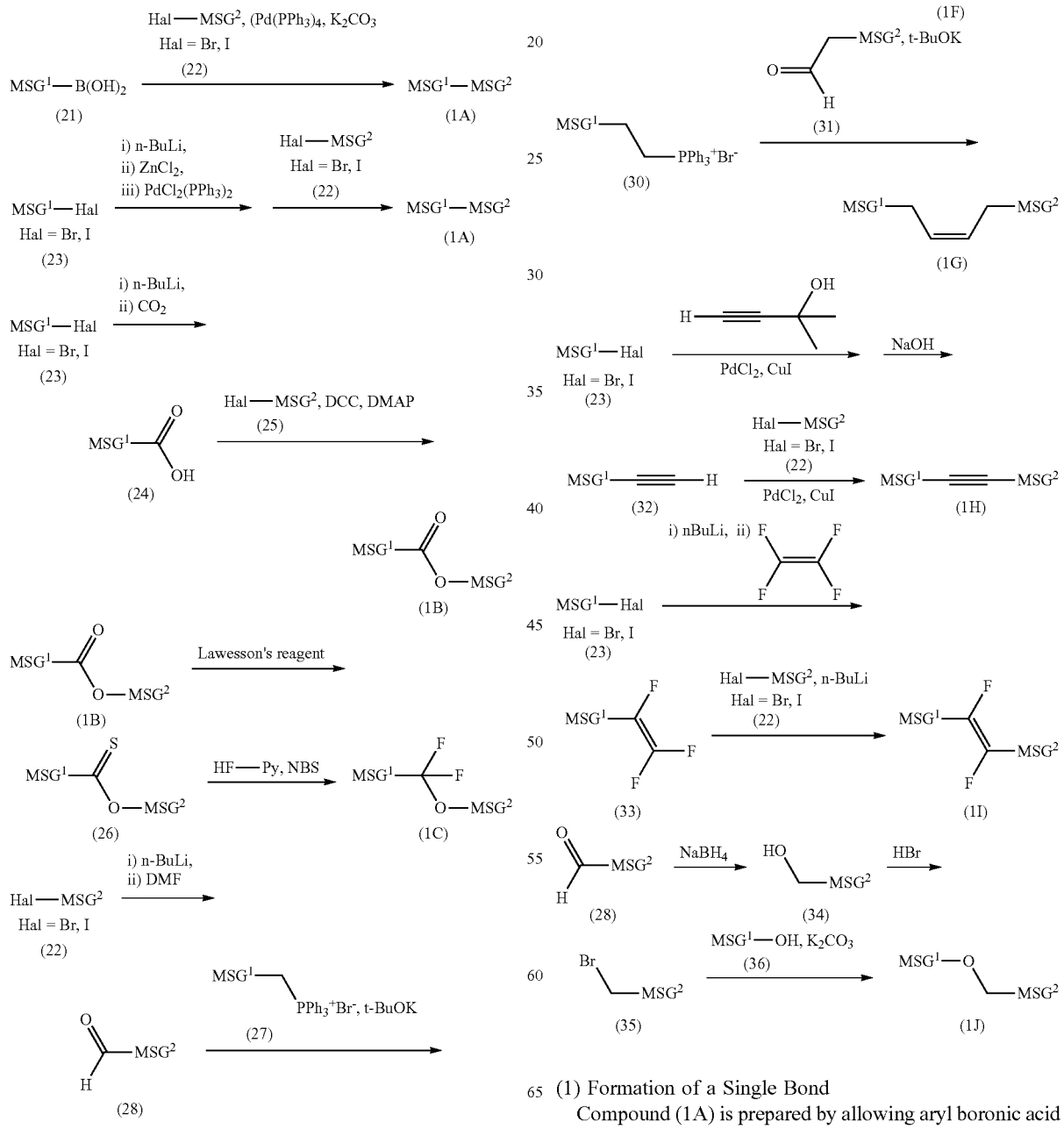

(1) Formation of a Single Bond

Compound (1A) is prepared by allowing aryl boronic acid (21) prepared according to a known method to react with halide (22) in the presence of carbonate and a catalyst such as tetrakis(triphenylphosphine)palladium. Compound (1A) is also prepared by allowing halide (23) prepared according to a known method to react with n-butyllithium and subsequently with zinc chloride, and further with halide (22) in the presence of a catalyst such as dichlorobis(triphenylphosphine)palladium.

(2) Formation of —COO—

Carboxylic acid (24) is obtained by allowing halide (23) to react with n-butyllithium and subsequently with carbon dioxide. Compound (1B) is prepared by dehydration of compound (25) prepared according to a known method and carboxylic acid (24) in the presence of 1,3-dicyclohexylcarbodiimide (DCC) and 4-dimethylaminopyridine (DMAP).

(3) Formation of —$CF_2O$—

Thionoester (26) is obtained by treating compound (1B) with a thiation reagent such as Lawesson's reagent. Compound (1C) is prepared by fluorinating thionoester (26) with a hydrogen fluoride-pyridine complex and N-bromosuccinimide (NBS). See M. Kuroboshi et al., Chem. Lett., 1992, 827. Compound (1C) is also prepared by fluorinating thionoester (26) with (diethylamino)sulfur trifluoride (DAST). See W. H. Bunnelle et al., J. Org. Chem. 1990, 55, 768. The bonding group can also be formed according to the method described in Peer. Kirsch et al., Angew. Chem. Int. Ed. 2001, 40, 1480.

(4) Formation of —CH=CH—

Aldehyde (28) is obtained by treating halide (22) with n-butyllithium and then allowing the treated halide to react with formamide such as N,N-dimethylformamide (DMF). Phosphorus ylide is generated by treating phosphonium salt (27) prepared according to a known method with a base such as potassium t-butoxide. Compound (1D) is prepared by allowing the phosphorus ylide to react with aldehyde (28). A cis isomer is generated depending on reaction conditions, and therefore the cis isomer is isomerized into a trans isomer according to a known method, when necessary.

(5) Formation of —$(CH_2)_2$—

Compound (1E) is prepared by hydrogenating compound (1D) in the presence of a catalyst such as palladium on carbon.

(6) Formation of —$(CH_2)_4$—

A compound having —$(CH_2)_2$—CH=CH— is obtained according to a method of the method (4) by using phosphonium salt (29) in place of phosphonium salt (27). Compound (1F) is prepared by performing catalytic hydrogenation of the compound obtained.

(7) Formation of —$CH_2CH=CHCH_2$—

Compound (1G) is prepared according to the method of the method (4) by using phosphonium salt (30) in place of phosphonium salt (27) and aldehyde (31) in place of aldehyde (28). A trans isomer is generated depending on reaction conditions, and therefore the trans isomer is isomerized to a cis isomer according to a known method, when necessary.

(8) Formation of —C≡C—

Compound (32) is obtained by allowing halide (23) to react with 2-methyl-3-butyn-2-ol in the presence of a catalyst including dichloropalladium and copper halide and then performing deprotection under basic conditions. Compound (1H) is prepared by allowing compound (32) to react with halide (22) in the presence of the catalyst including dichloropalladium and copper halide.

(9) Formation of —CF=CF—

Compound (33) is obtained by treating halide (23) with n-butyllithium and then allowing the treated halide to react with tetrafluoroethylene. Compound (11) is prepared by treating halide (22) with n-butyllithium and then allowing the treated halide to react with compound (33).

(10) Formation of —$OCH_2$—

Compound (34) is obtained by reducing aldehyde (28) with a reducing agent such as sodium borohydride. Bromide (35) is obtained by brominating compound (34) with hydrobromic acid or the like. Compound (1J) is prepared by allowing bromide (35) to react with compound (36) in the presence of a base such as potassium carbonate or the like.

(11) Formation of —$(CF_2)_2$—

A compound having —$(CF_2)_2$— is obtained by fluorinating diketone (—COCO—) with sulfur tetrafluoride, in the presence of a hydrogen fluoride catalyst, according to the method described in J. Am. Chem. Soc., 2001, 123, 5414.

2-2. Formation of ring $A^1$ to ring $A^4$

With regard to a ring such as 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl, pyrimidine-2,5-diyl, or pyridine-2,5-diyl, a starting material thereof is commercially available or a synthetic method thereof is well known.

2-3. Method for Preparing Compound (1)

A method for preparing compound (1) is as described in a scheme below. In the compounds, symbols such as $R^1$ and ring $A^1$ are defined in a manner identical with the definitions of symbols described in item 1.

2-3a. Compound Having Divalent Group Represented by Formula (ch)

Bromide (41) is prepared according to a known method. Alcohol (43) is obtained by allowing a Grignard reagent prepared from bromide (41) to react with ketone (42). Compound (1) is prepared by dehydration of alcohol (43) in the presence of p-toluenesulfonic acid monohydrate (PTSA).

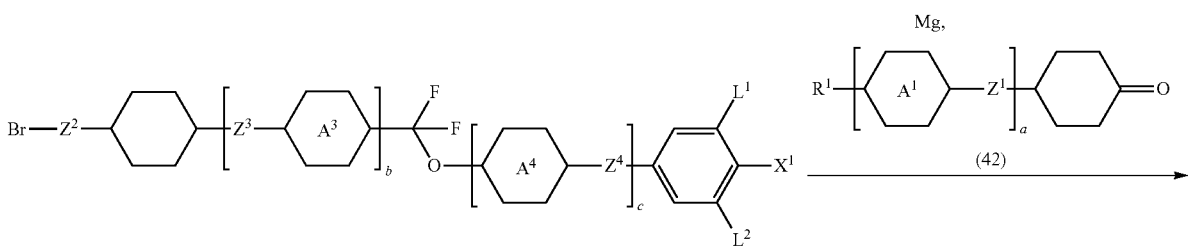

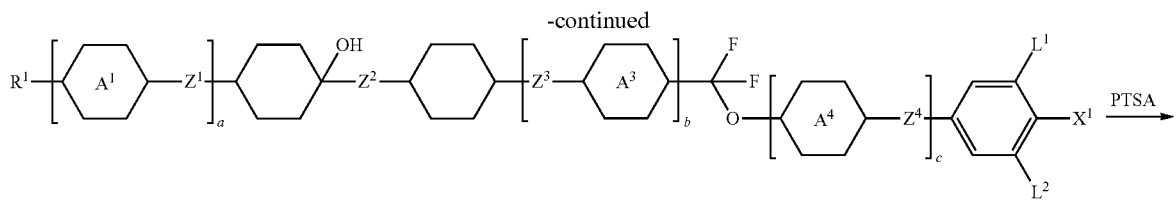

(43)

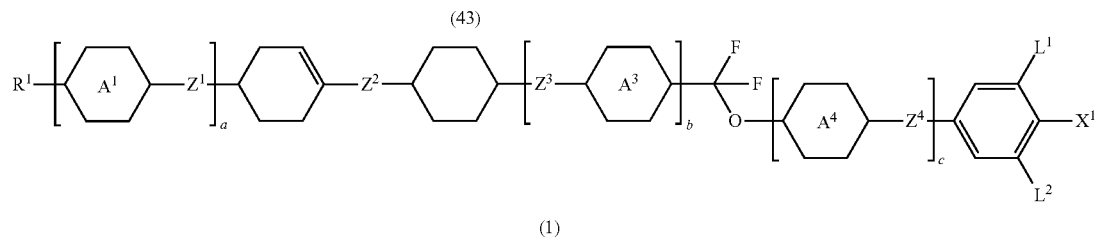

(1)

2-3b. Compound Having Divalent Group Represented by Formula (Cx)

Ketone (44) is prepared according to a known method. Bromide (45) is obtained by brominating ketone (44) in the presence of N-bromosuccinimide (NBS) and PTSA. Ketone (46) is obtained by allowing a dehydrobromination reaction of bromide (45) in the presence of lithium carbonate and lithium bromide. Alcohol (48) is obtained by allowing a Grignard reagent prepared from bromide (47) to react with ketone (46). Compound (1) is prepared by reducing alcohol (48) in the presence of triethylsilane and boron trifluoride diethyl ether complex.

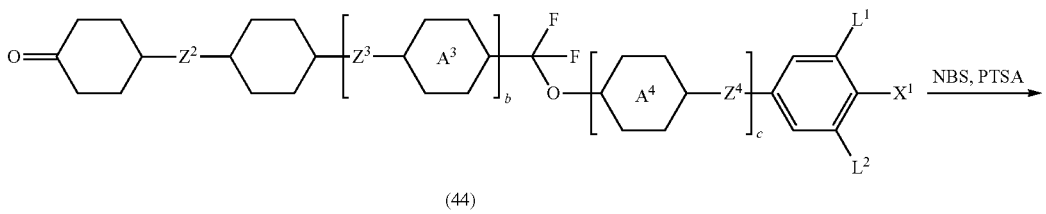

(44)

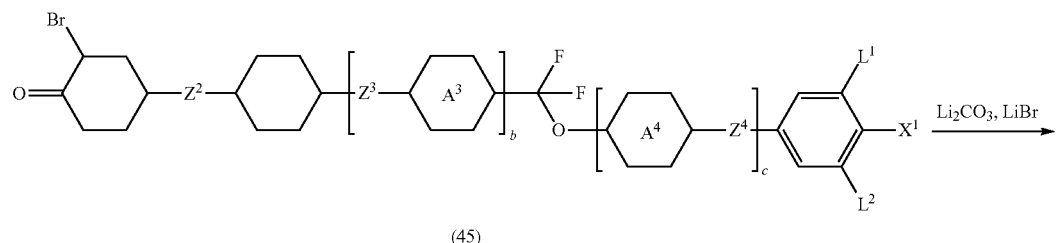

(45)

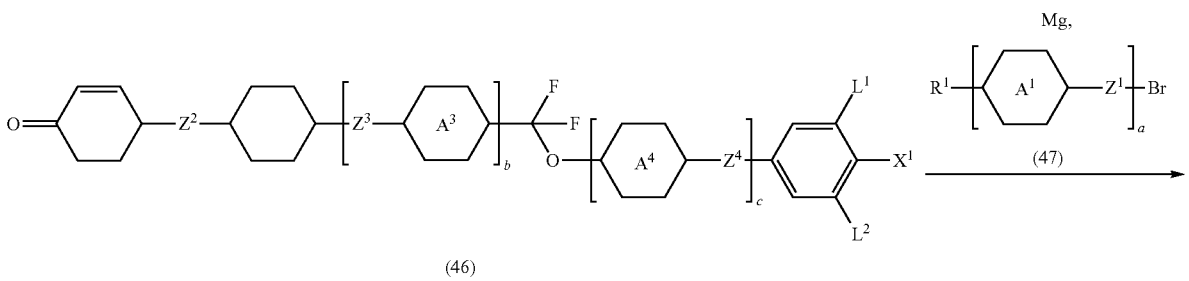

(46)

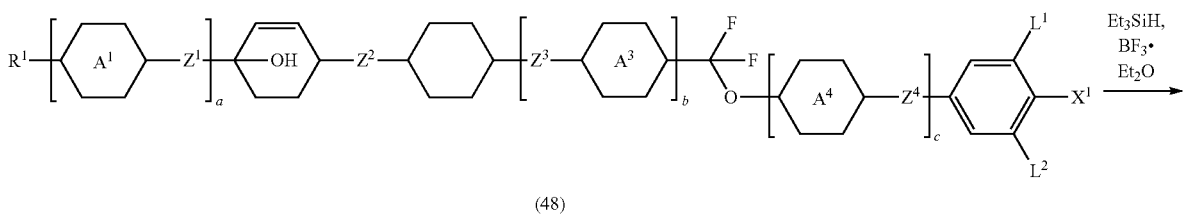

(48)

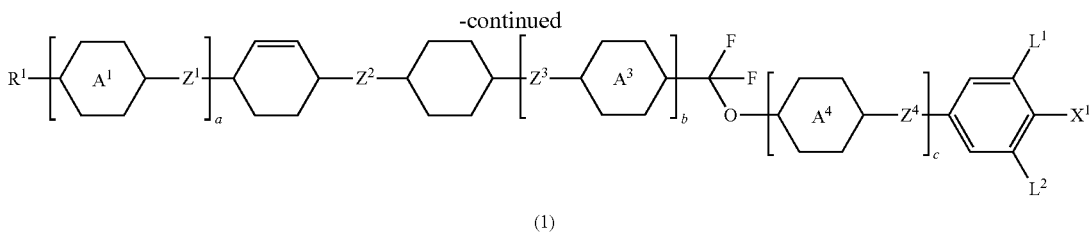

(1)

2-3c. Compound Having Divalent Group Represented by Formula (Ch)

Alcohol (49) is obtained by allowing a Grignard reagent prepared from bromide (47) to react with ketone (44). Compound (1) is prepared by dehydrating alcohol (49) in the presence of PTSA.

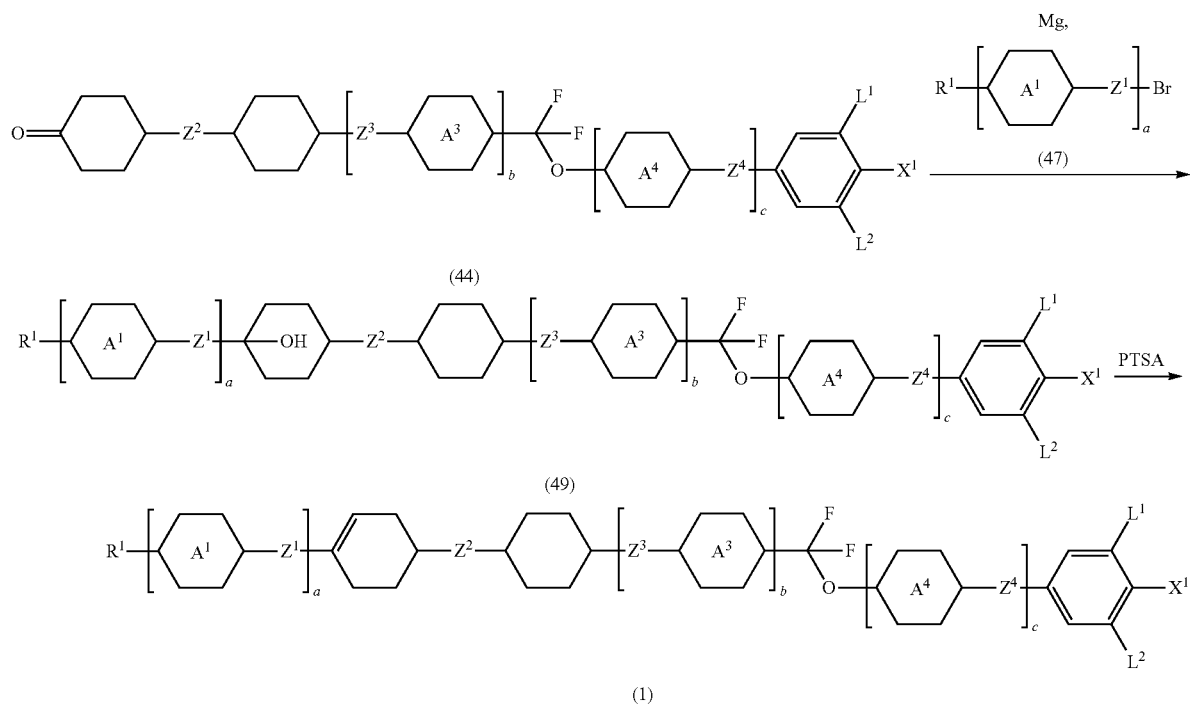

(1)

3. Liquid Crystal Composition
3-1. Component Compound

A liquid crystal composition of the invention is described. The composition contains at least one compound (1) as component A. The composition may contain two, three or more compounds (1). A component in the composition may be only compound (1). In order to develop excellent physical properties, the composition preferably contains at least one of compounds (1) in the range of approximately 1 to approximately 99% by weight. In a composition having a positive dielectric anisotropy, a preferred content of compound (1) is in the range of approximately 5 to approximately 60% by weight. In a composition having a negative dielectric anisotropy, a preferred content of compound (1) is approximately 30% by weight or less. The composition may contain compound (1) and liquid crystal compounds that are not described herein.

The composition contains compound (1) as component A, and preferably further contains a liquid crystal compound selected from components B, C, D and E described below. Component B includes compounds (2) to (4). Component C includes compounds (5) to (7). Component D includes compound (8). Component E includes compounds (9) to (15). The composition may contain any other liquid crystal compound different from compounds (2) to (15). When the composition is prepared, components B, C, D and E are preferably selected by taking into account a positive or negative dielectric anisotropy and magnitude of the dielectric anisotropy. A composition in which the components are suitably selected has a high stability to heat and light, a high maximum temperature, a low minimum temperature, a small viscosity, a suitable optical anisotropy (namely, a large optical anisotropy or a small optical anisotropy), a large dielectric anisotropy, a large specific resistance and a suitable elastic constant (namely, a large elastic constant or a small elastic constant).

Component B includes a compound in which two terminal groups are alkyl or the like. Preferred examples of component B include compounds (2-1) to (2-11), compounds (3-1) to (3-19) and compounds (4-1) to (4-7). In the compounds, $R^{11}$ and $R^{12}$ are independently alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine.

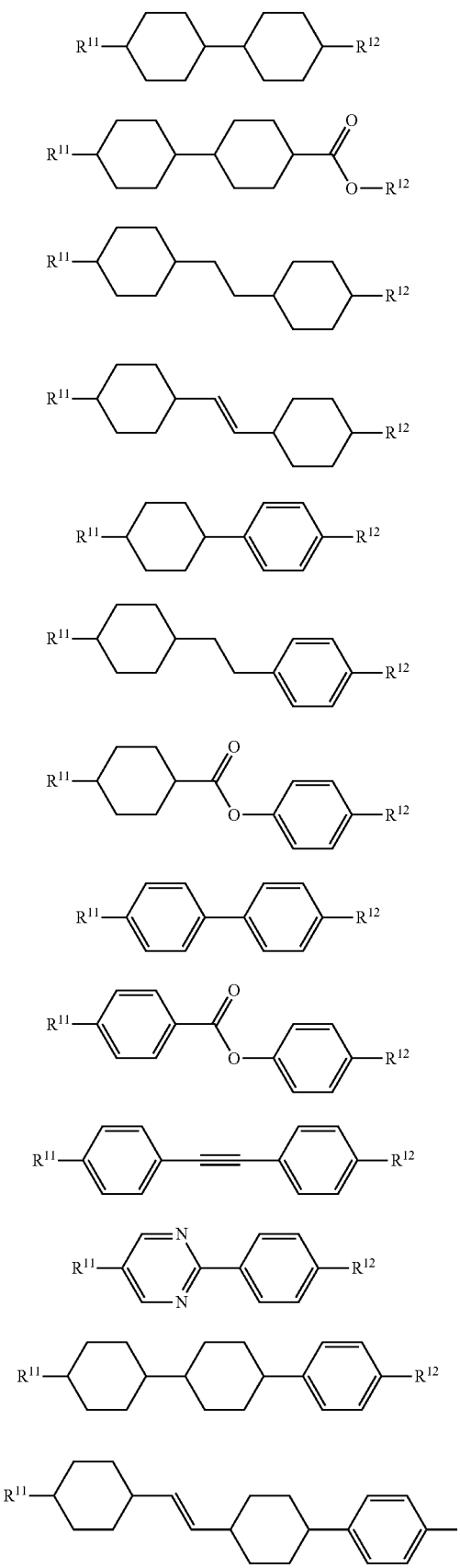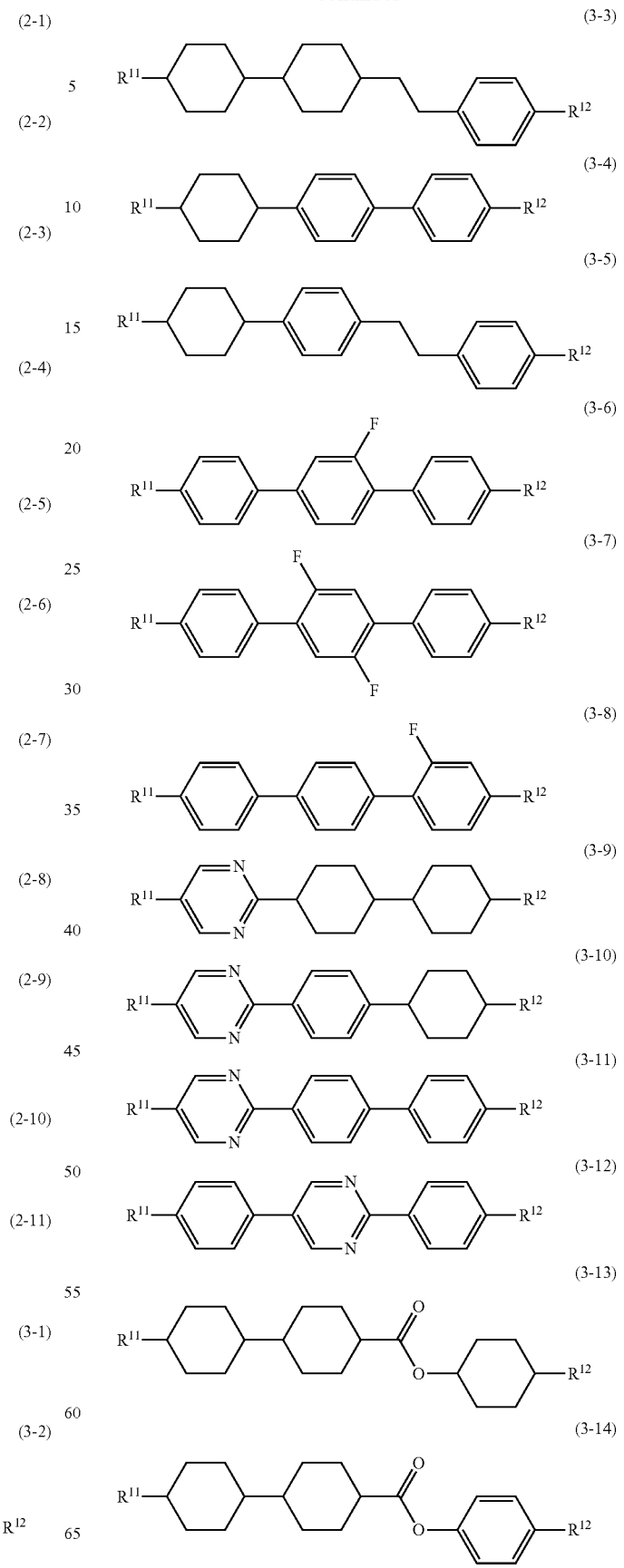

(3-15)
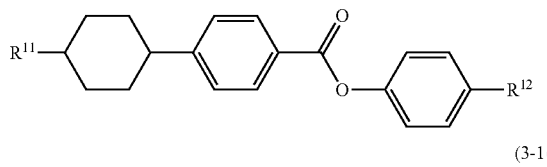

(3-16)
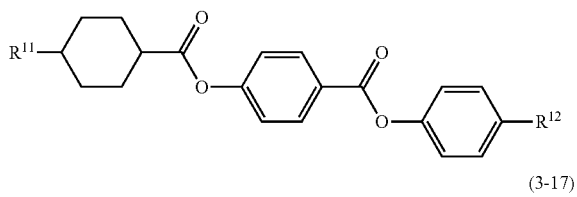

(3-17)
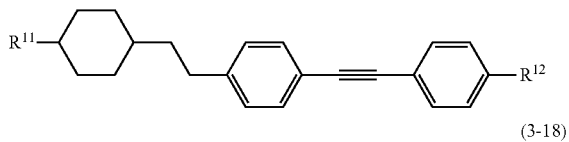

(3-18)
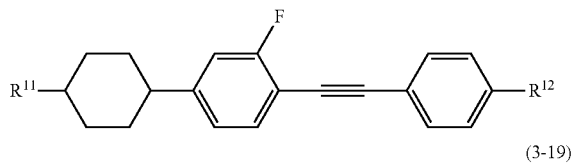

(3-19)
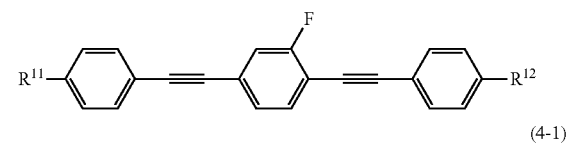

(4-1)
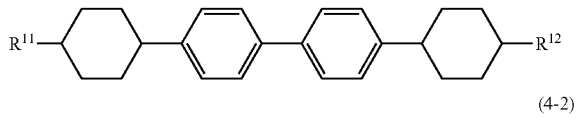

(4-2)
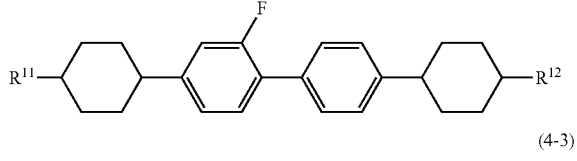

(4-3)
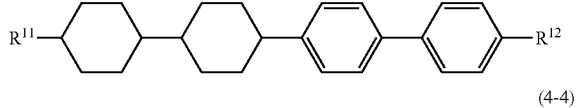

(4-4)
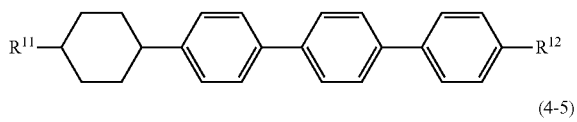

(4-5)
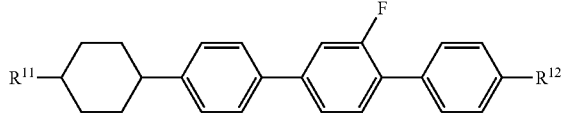

(4-6)
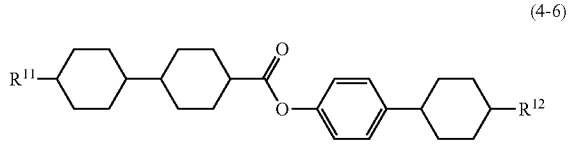

(4-7)
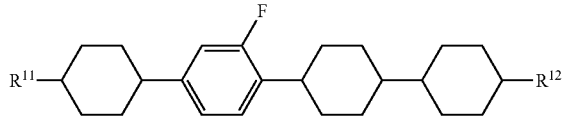

Component B has a small dielectric anisotropy. Component B is close to neutrality. Compound (2) is effective in decreasing the viscosity or adjusting the optical anisotropy. Compounds (3) and (4) are effective in extending the temperature range of the nematic phase by increasing the maximum temperature, or in adjusting the optical anisotropy.

As a content of component B is increased, the viscosity of the composition is decreased, and the dielectric anisotropy is decreased. Thus, as long as a desired value of threshold voltage of the device is met, the content is preferably as large as possible. When a composition for the IPS mode, the VA mode or the like is prepared, the content of component B is preferably approximately 30% by weight or more, and further preferably approximately 40% by weight or more, based on the weight of the liquid crystal composition.

Component C is a compound having a halogen-containing group or a fluorine-containing group at a right terminal. Preferred examples of component C include compounds (5-1) to (5-16), compounds (6-1) to (6-113) and compounds (7-1) to (7-57). In the compounds, $R^{13}$ is alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine; $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$.

(5-1)
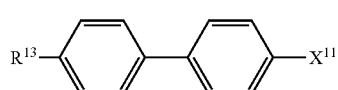

(5-2)
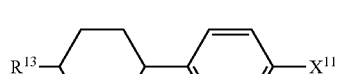

(5-3)

(5-4)

(5-5)
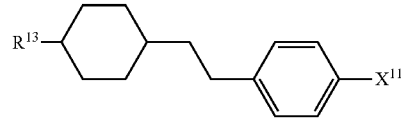

(5-6) 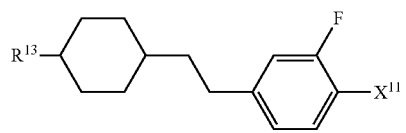
(5-7) 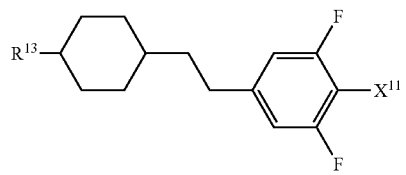
(5-8) 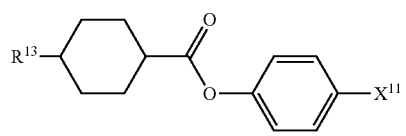
(5-9) 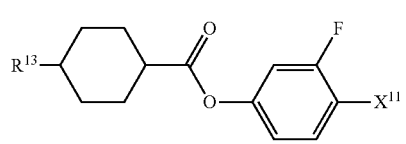
(5-10) 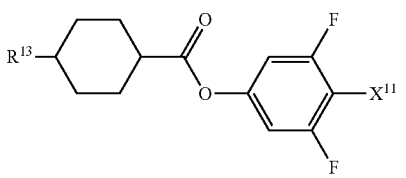
(5-11) 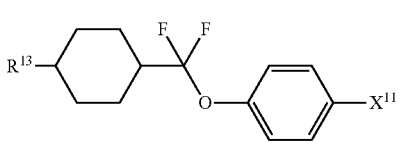
(5-12) 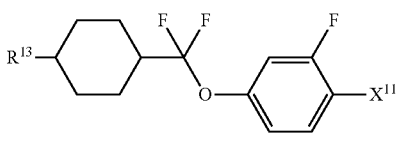
(5-13) 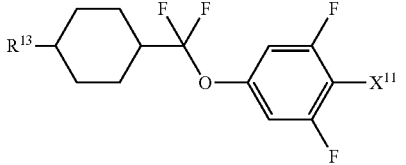
(5-14) 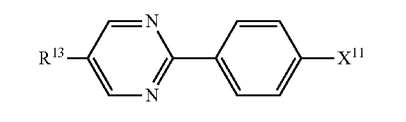
(5-15) 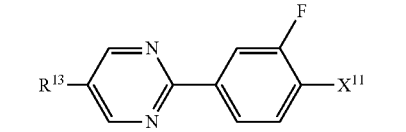
(5-16) 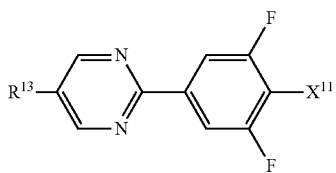
(6-1) 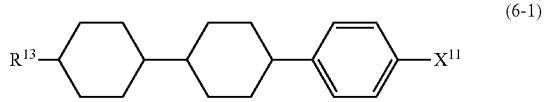
(6-2) 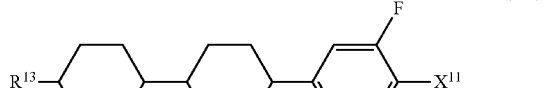
(6-3) 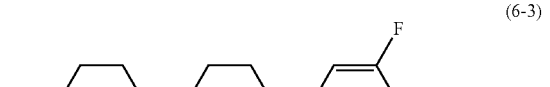
(6-4) 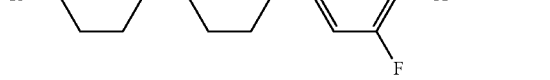
(6-5) 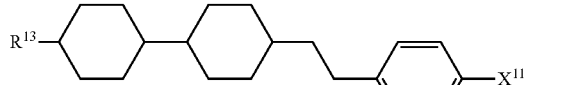
(6-6) 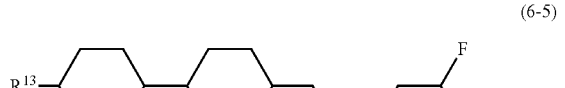
(6-7) 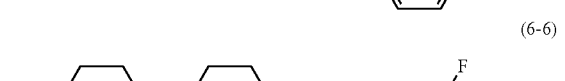
(6-8) 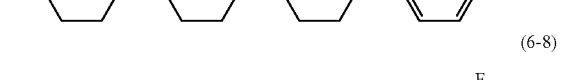
(6-9) 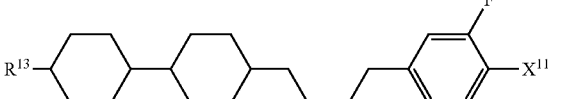

(6-10) 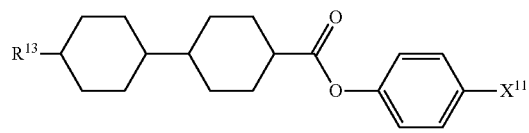
(6-11) 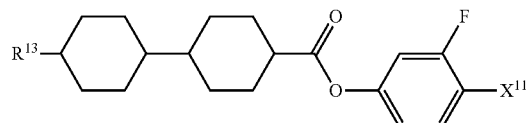
(6-12) 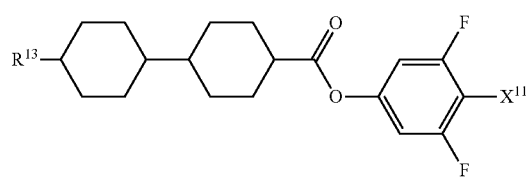
(6-13) 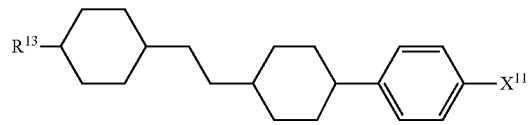
(6-14) 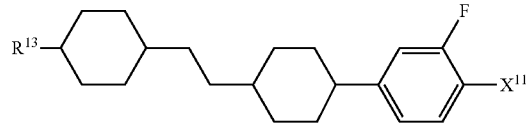
(6-15) 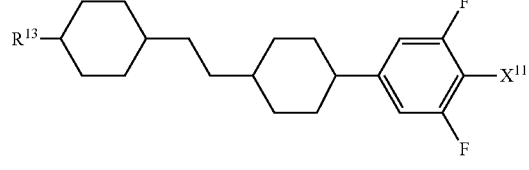
(6-16) 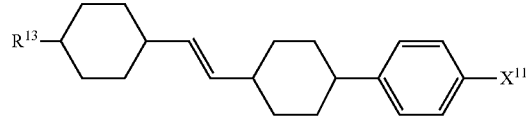
(6-17) 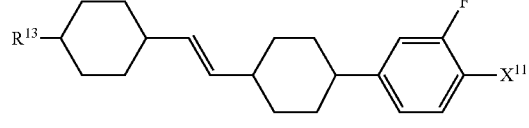
(6-18) 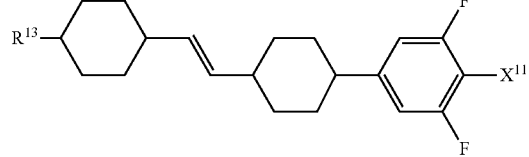
(6-19) 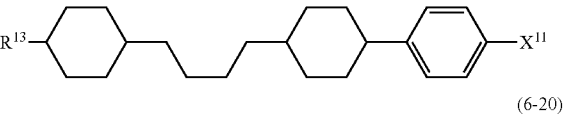
(6-20) 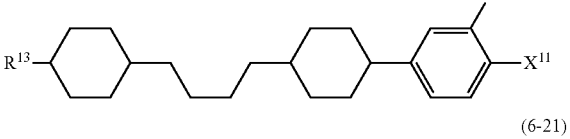
(6-21) 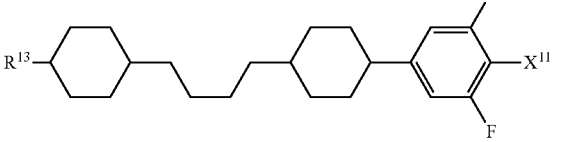
(6-22) 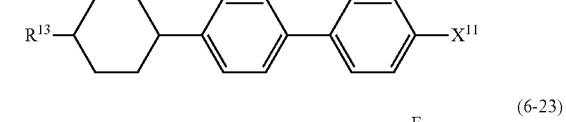
(6-23) 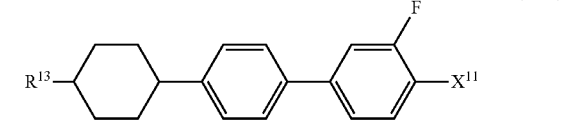
(6-24) 
(6-25) 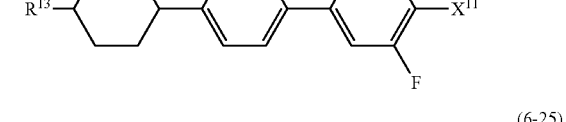
(6-26) 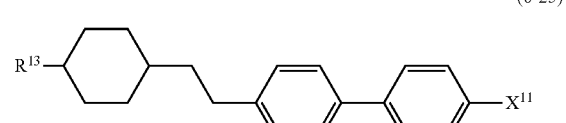
(6-27) 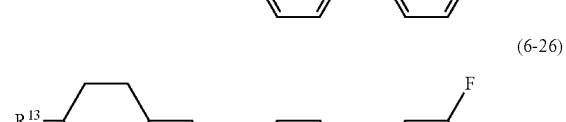
(6-28) 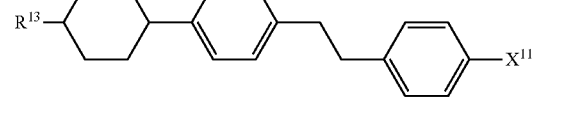

(6-29)
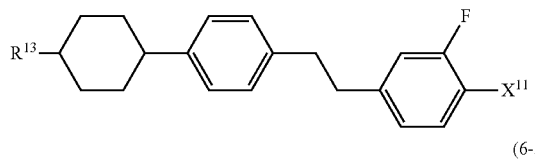
(6-30)
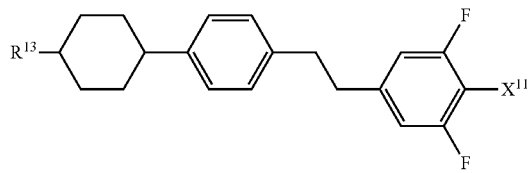
(6-31)
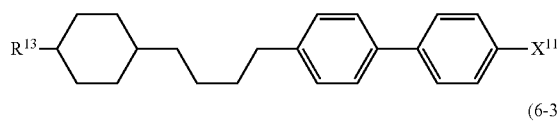
(6-32)
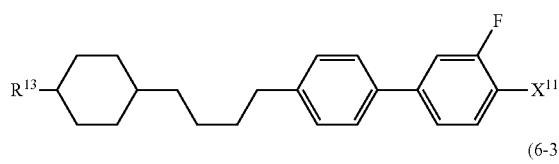
(6-33)
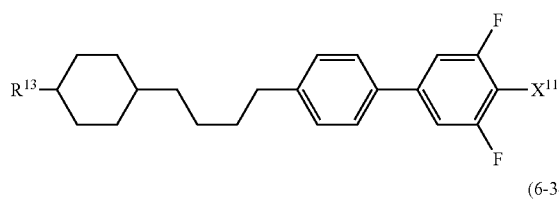
(6-34)
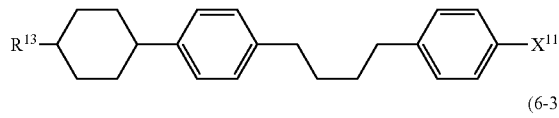
(6-35)
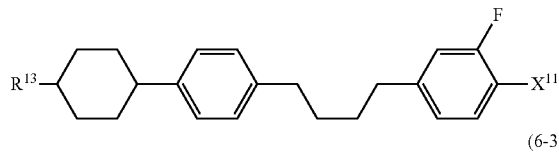
(6-36)
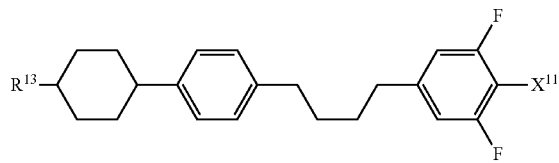
(6-37)
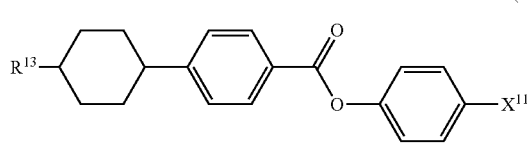
(6-38)
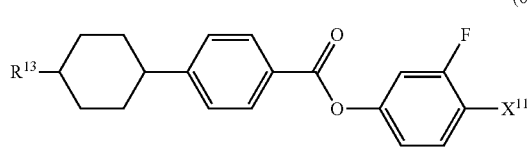
(6-39)
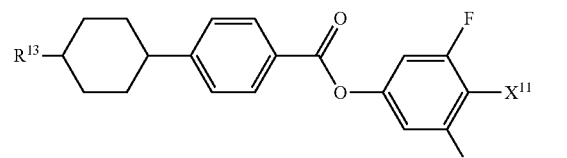
(6-40)
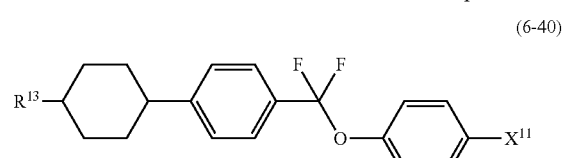
(6-41)
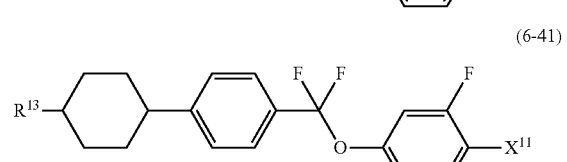
(6-42)
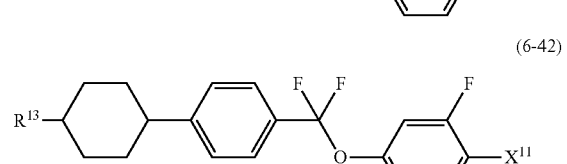
(6-43)
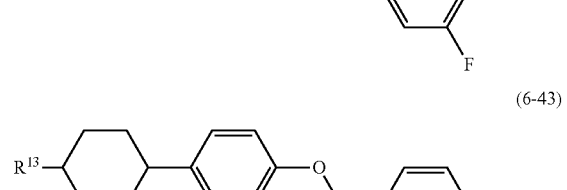
(6-44)
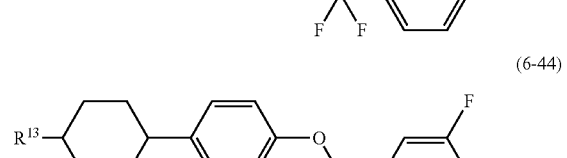
(6-45)
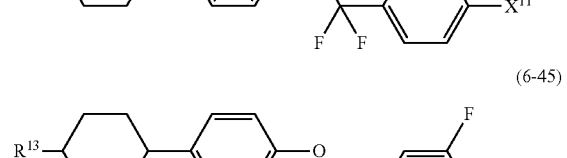
(6-46)
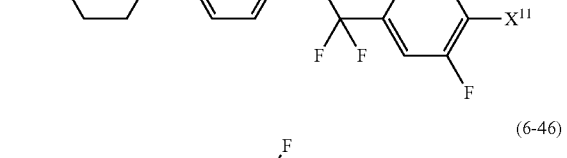
(6-47)
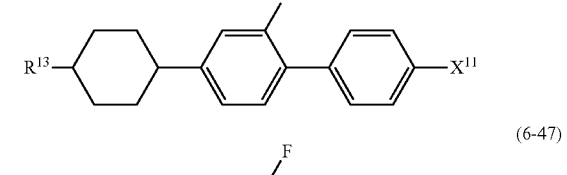

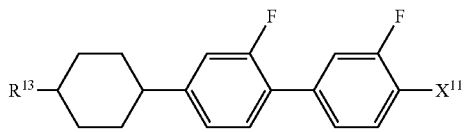
(6-48)
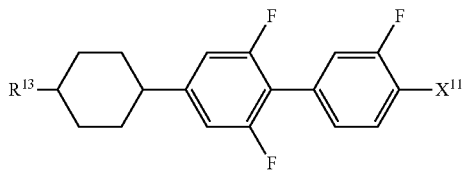
(6-49)
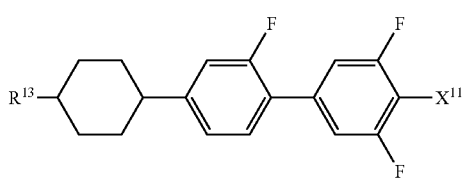
(6-50)
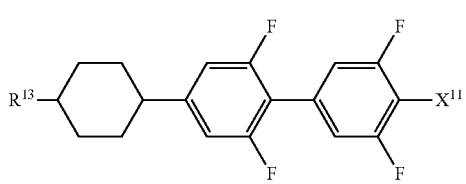
(6-51)
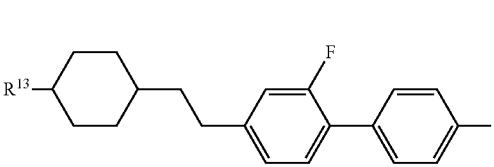
(6-52)
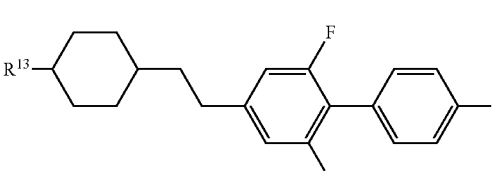
(6-53)
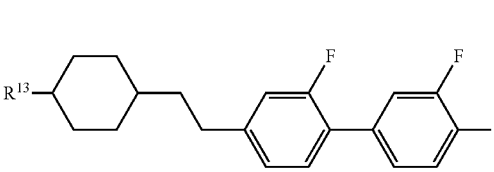
(6-54)
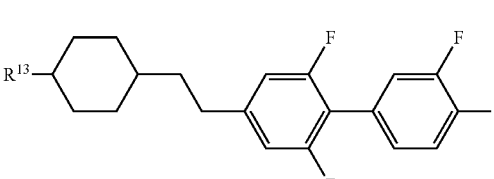
(6-55)
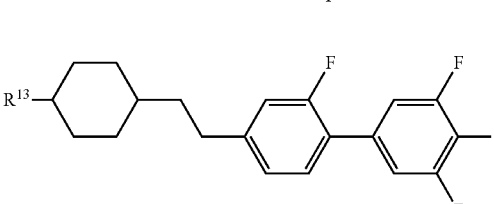
(6-56)
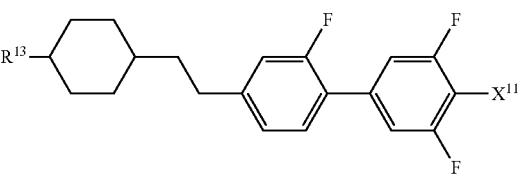
(6-57)
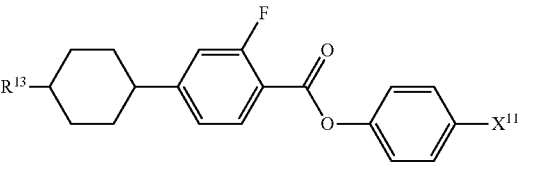
(6-58)
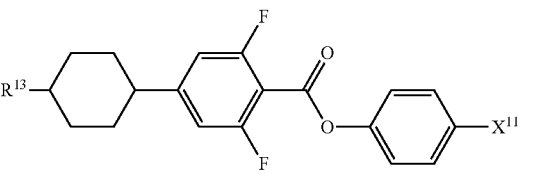
(6-59)
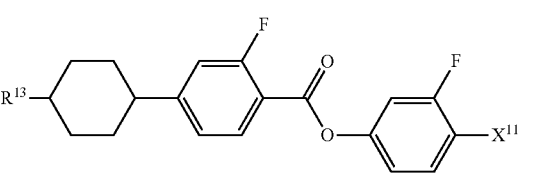
(6-60)
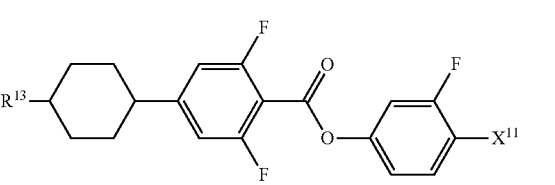
(6-61)
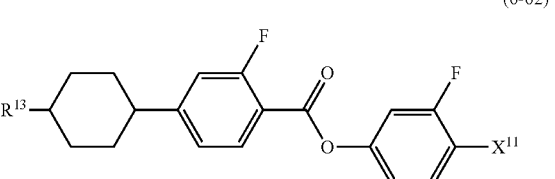
(6-62)
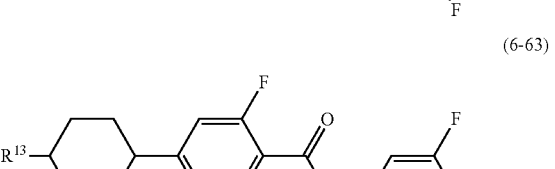
(6-63)
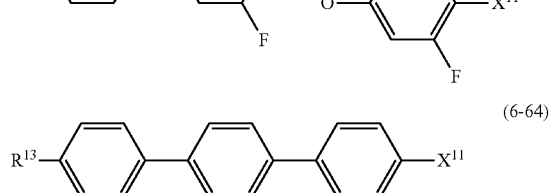
(6-64)

(6-65)
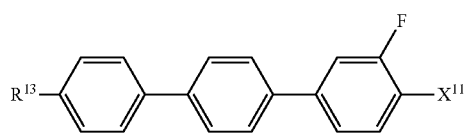
(6-66)
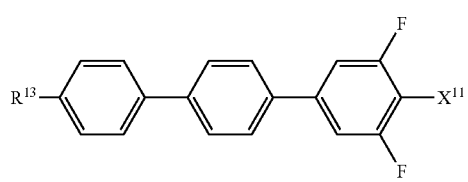
(6-67)
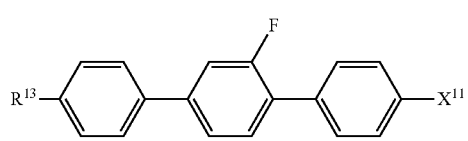
(6-68)
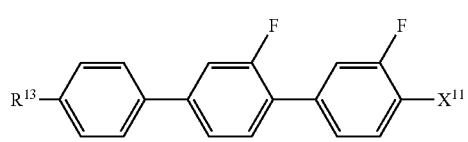
(6-69)
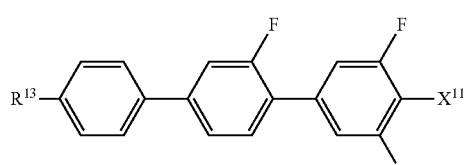
(6-70)
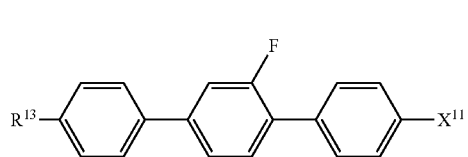
(6-71)
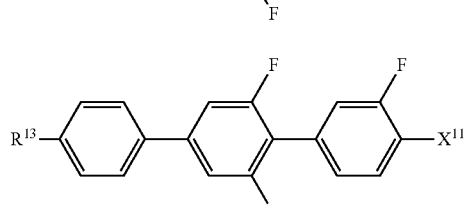
(6-72)
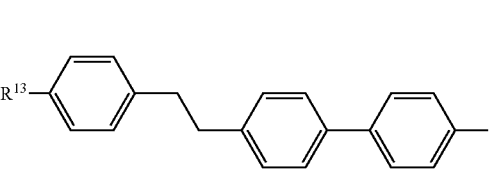
(6-73)
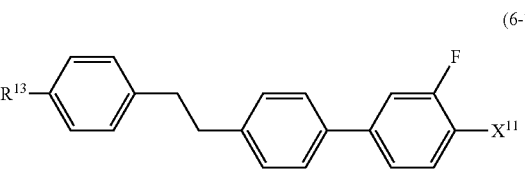
(6-74)
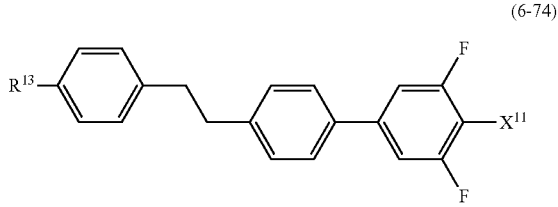
(6-75)
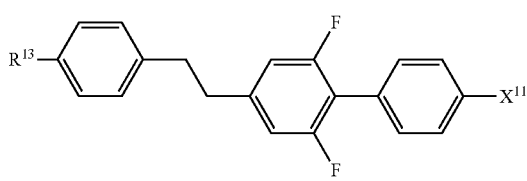
(6-76)
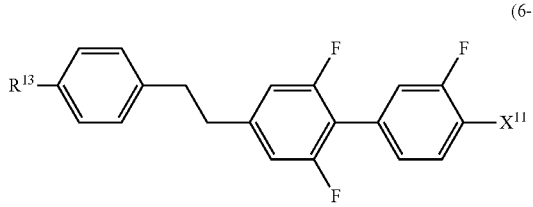
(6-77)
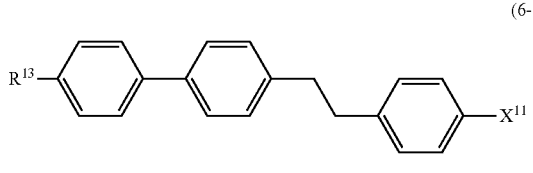
(6-78)
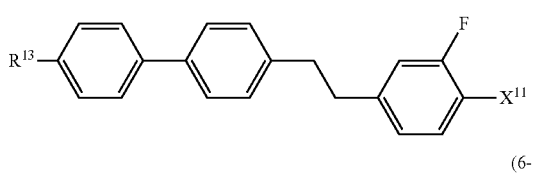
(6-79)
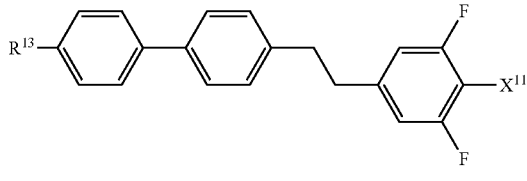
(6-80)
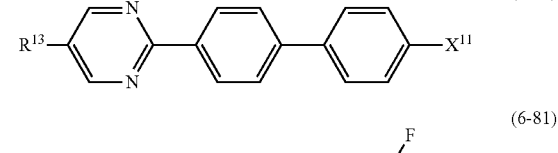
(6-81)
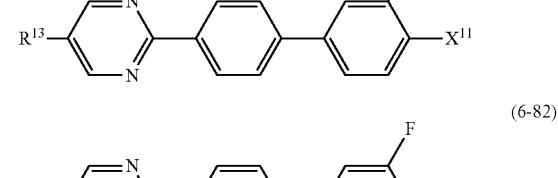
(6-82)
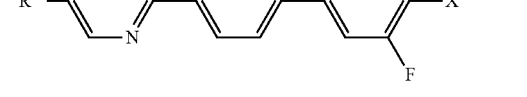

(6-83)
(6-84)
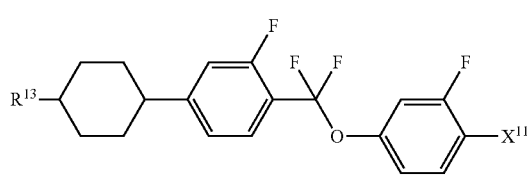
(6-85)
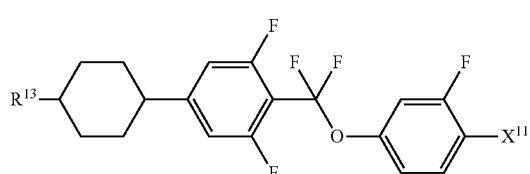
(6-86)
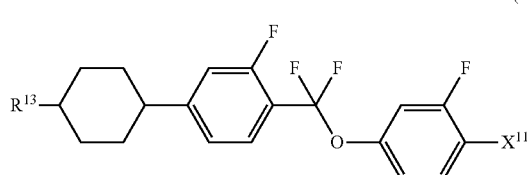
(6-87)
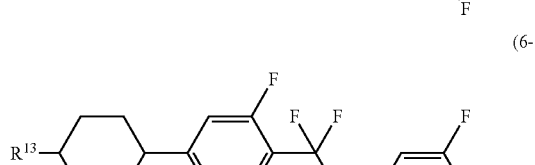
(6-88)
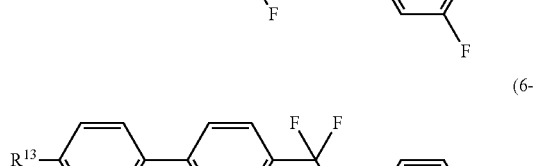
(6-89)
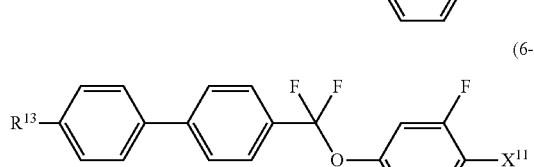
(6-90)
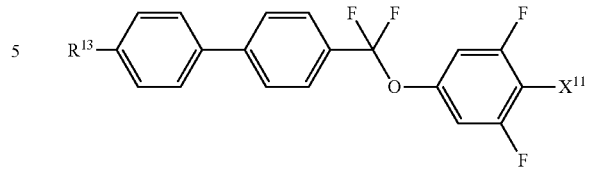
(6-91)
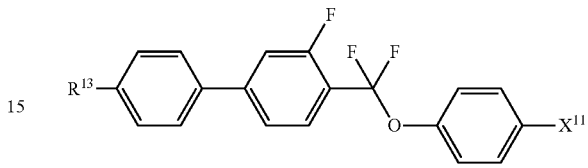
(6-92)
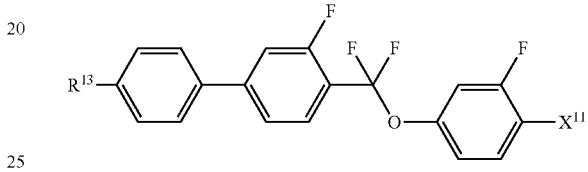
(6-93)
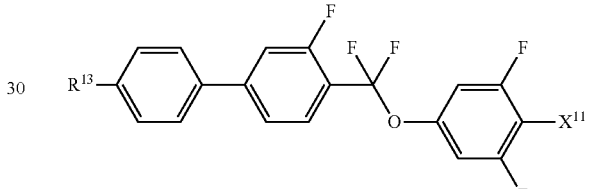
(6-94)
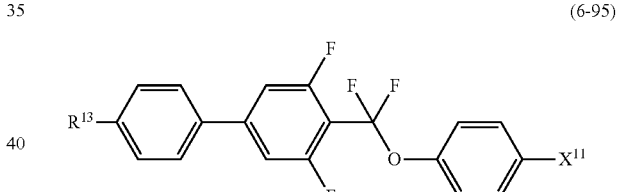
(6-95)
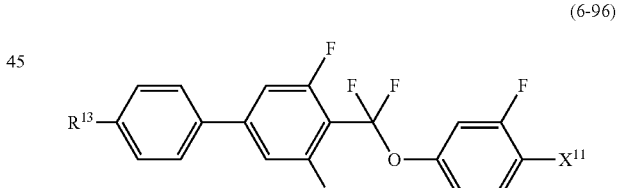
(6-96)
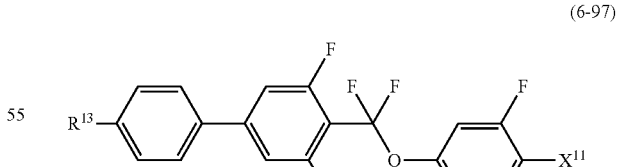
(6-97)
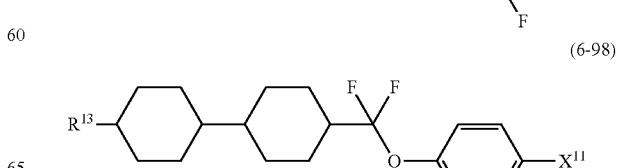
(6-98)

(6-99) 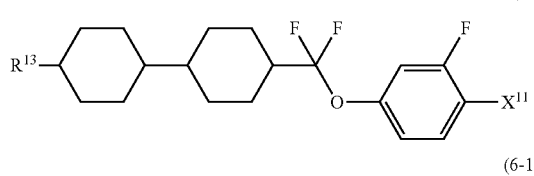
(6-100) 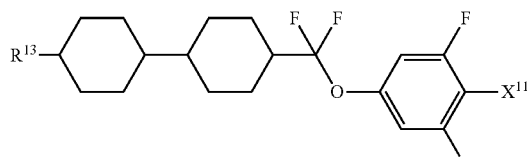
(6-101) 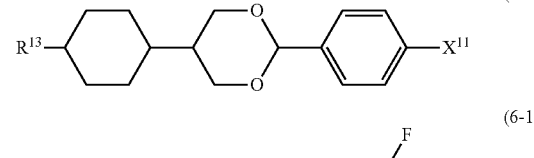
(6-102) 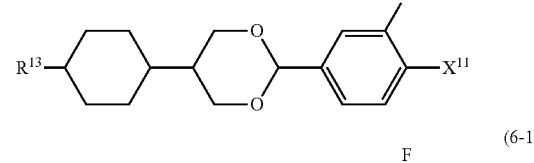
(6-103) 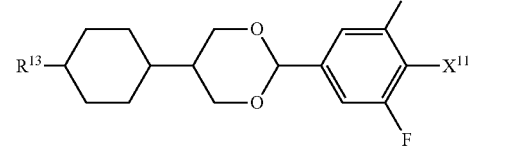
(6-104) 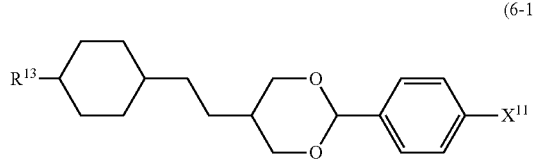
(6-105) 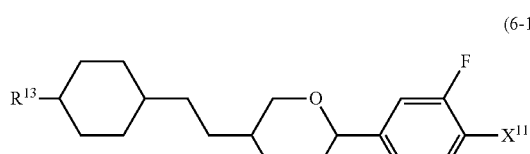
(6-106) 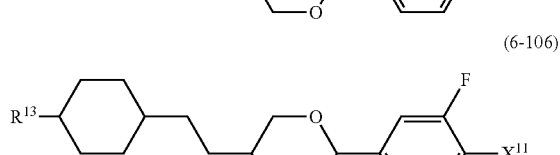
(6-107) 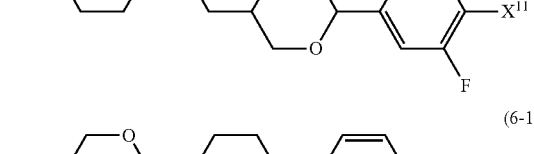
(6-108) 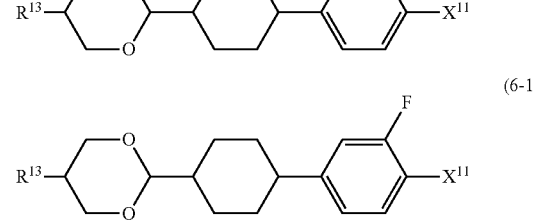
(6-109) 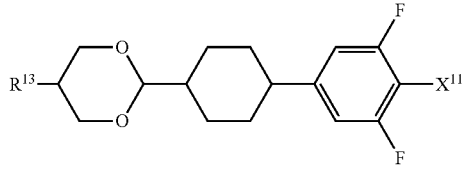
(6-110) 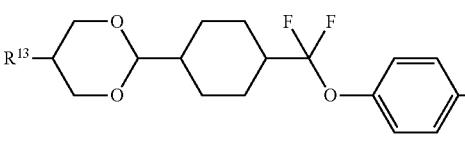
(6-111) 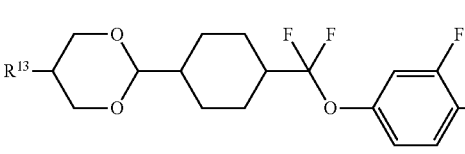
(6-112) 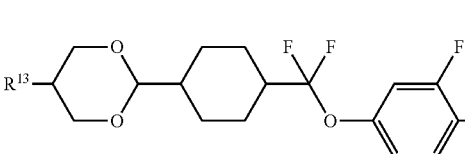
(6-113) 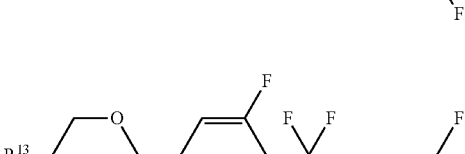
(7-1) 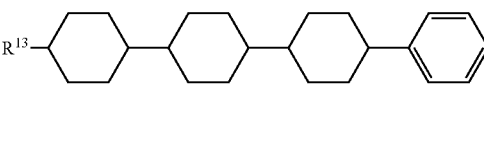
(7-2) 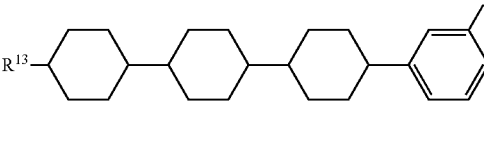
(7-3) 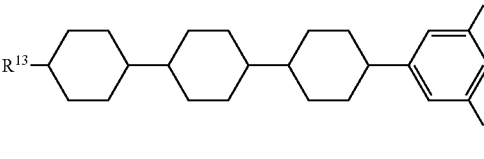
(7-4) 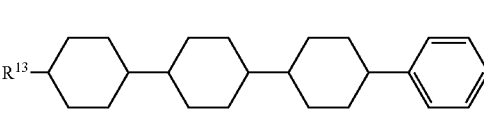

(7-5) 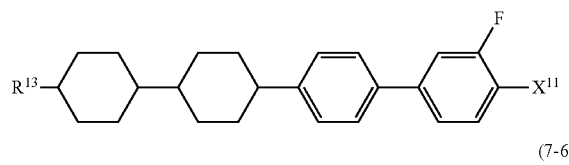
(7-6) 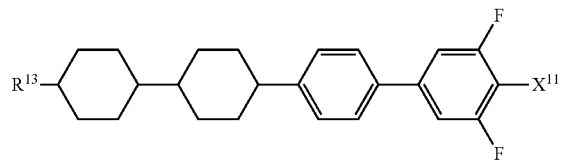
(7-7) 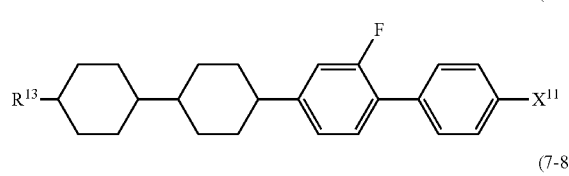
(7-8) 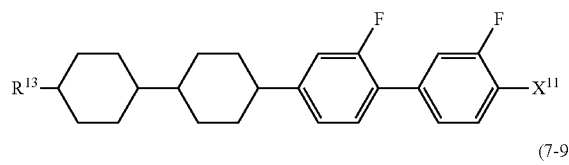
(7-9) 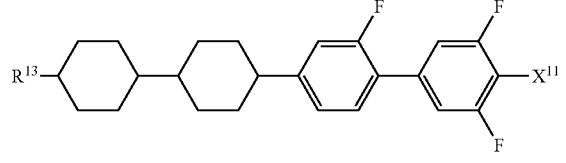
(7-10) 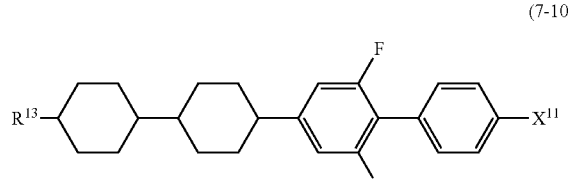
(7-11) 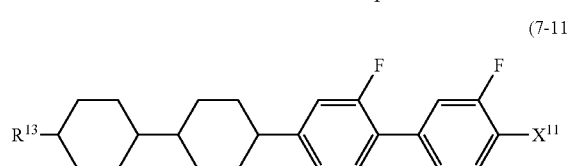
(7-12) 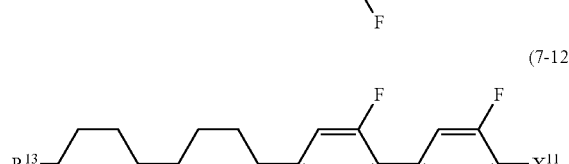
(7-13) 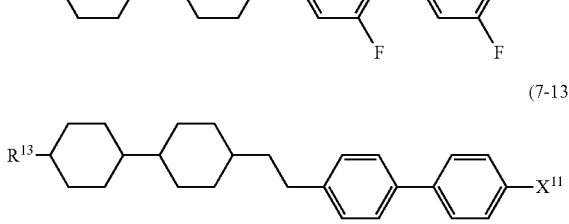
(7-14) 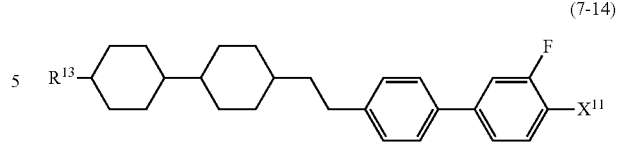
(7-15) 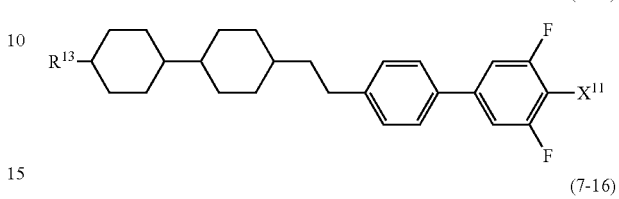
(7-16) 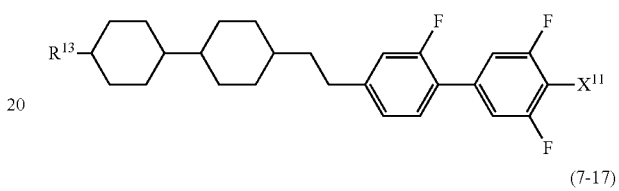
(7-17) 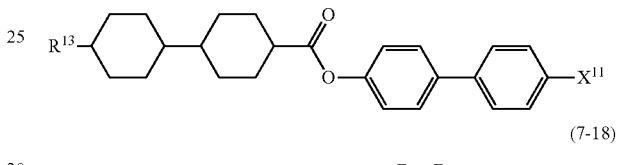
(7-18) 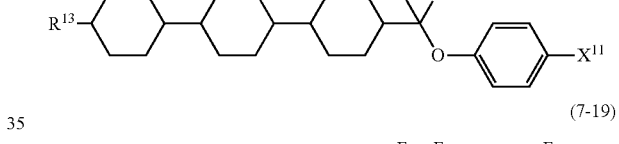
(7-19) 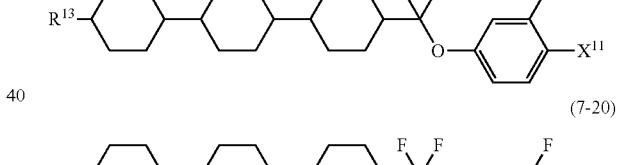
(7-20) 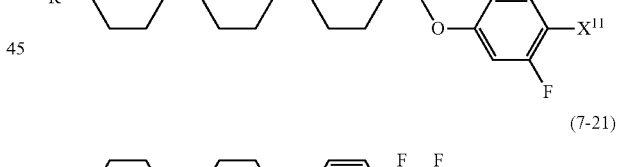
(7-21) 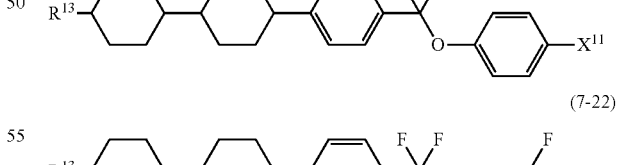
(7-22) 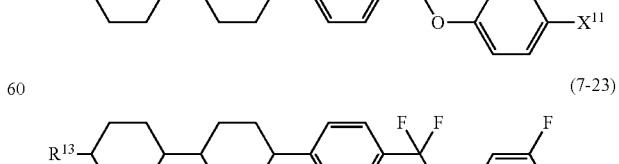
(7-23) 

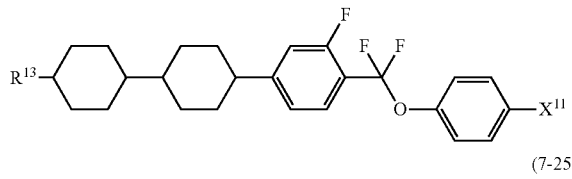
(7-24)
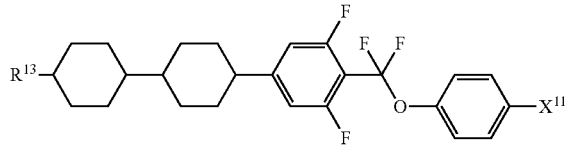
(7-25)
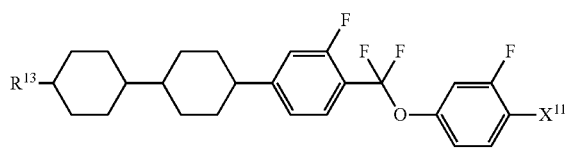
(7-26)
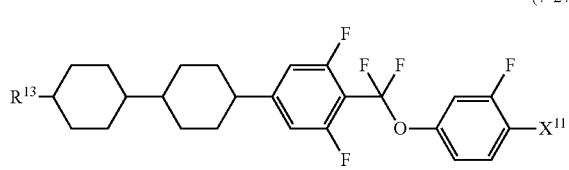
(7-27)
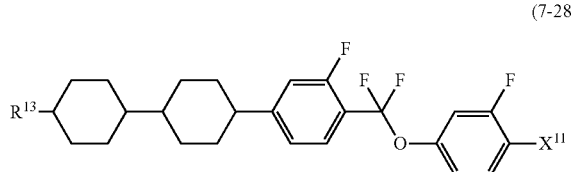
(7-28)
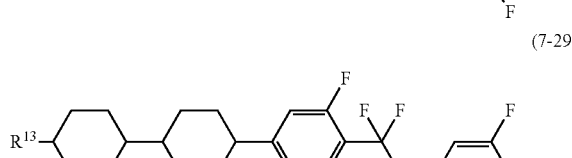
(7-29)
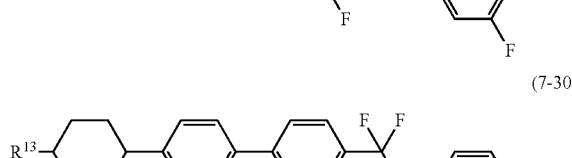
(7-30)
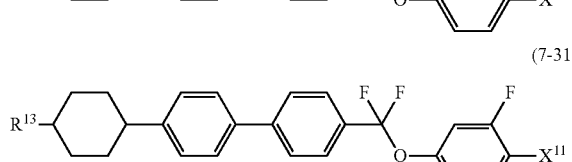
(7-31)
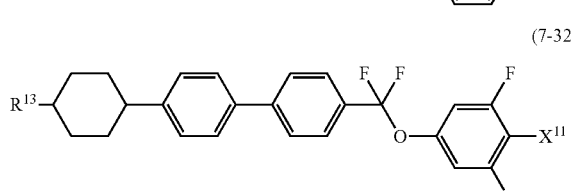
(7-32)
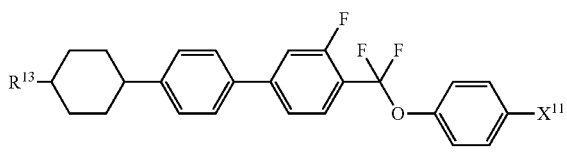
(7-33)
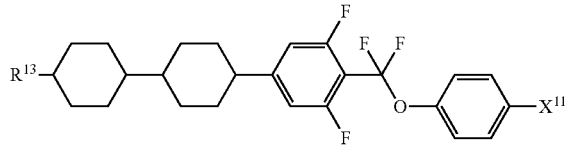
(7-34)
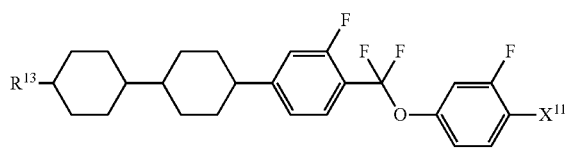
(7-35)
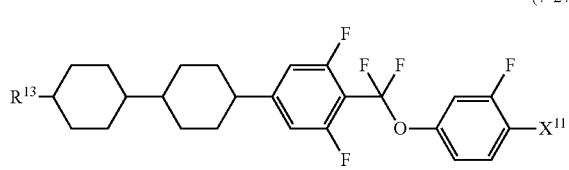
(7-36)
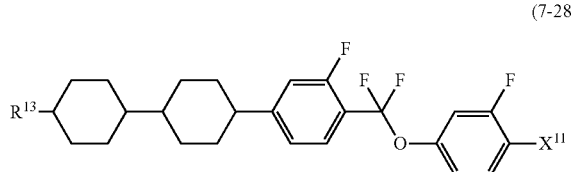
(7-37)
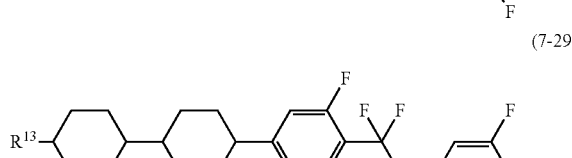
(7-38)
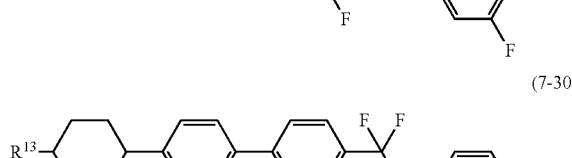
(7-39)
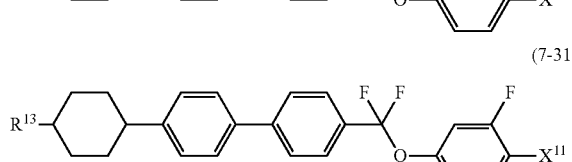
(7-40)

(7-41)
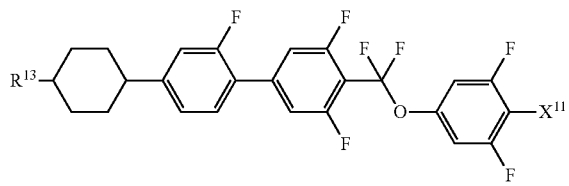
(7-42)
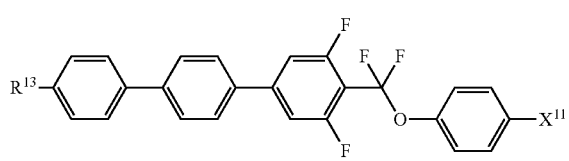
(7-43)
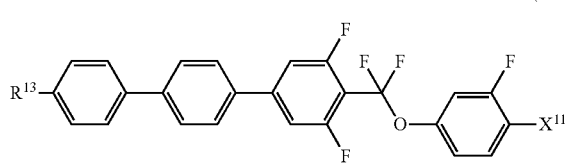
(7-44)
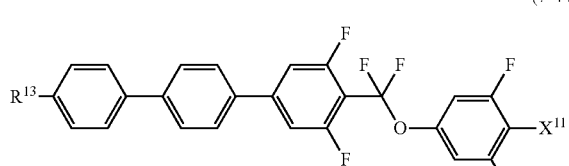
(7-45)
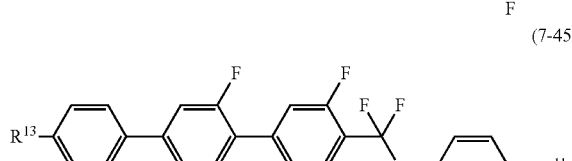
(7-46)
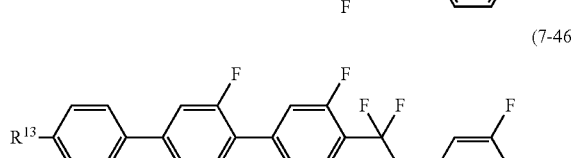
(7-47)
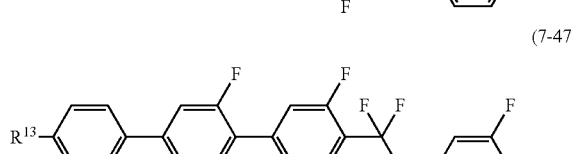
(7-48)
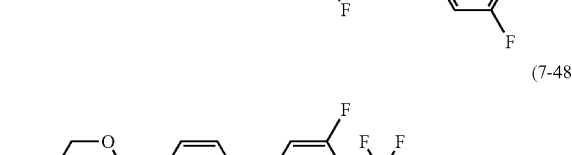
(7-49)
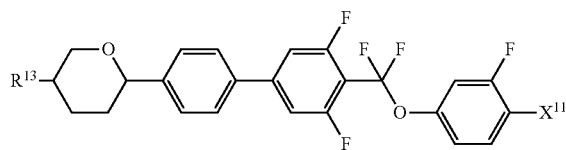
(7-50)
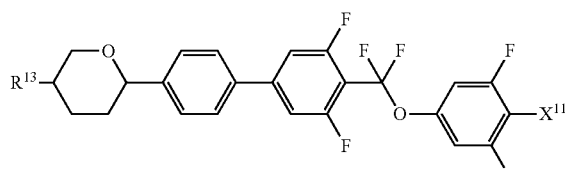
(7-51)
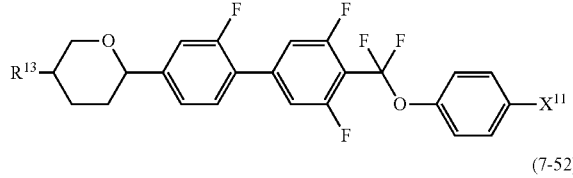
(7-52)
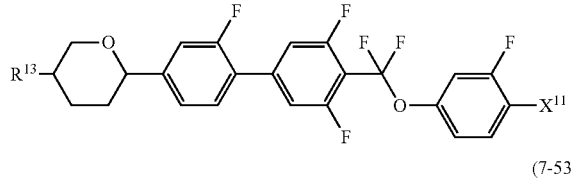
(7-53)
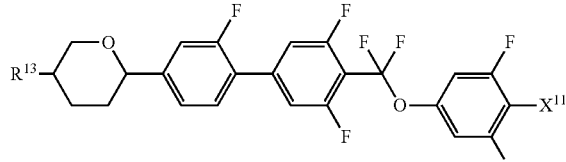
(7-54)
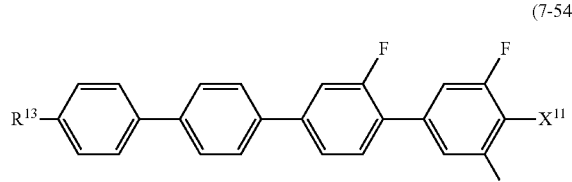
(7-55)
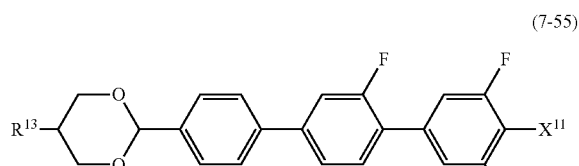
(7-56)
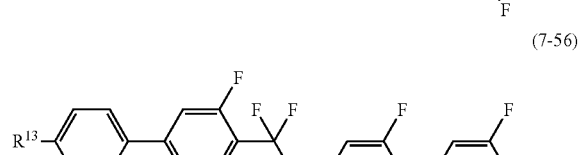

Component C has the positive dielectric anisotropy, and superb stability to heat and light, and therefore is used when a composition for the IPS mode, the FFS mode, the OCB mode or the like is prepared. A content of component C is suitably in the range of approximately 1 to approximately 99% by weight, preferably in the range of approximately 10 to approximately 97% by weight, and further preferably in the range of approximately 40 to approximately 95% by weight, based on the weight of the liquid crystal composition. When component C is added to a composition having the negative dielectric anisotropy, the content of component C is preferably approximately 30% by weight or less. Addition of component C allows adjustment of the elastic constant of the composition and adjustment of a voltage-transmittance curve of the device.

Component D is compound (8) in which a right-terminal group is —C≡N or —C≡C—C≡N. Preferred examples of component D include compounds (8-1) to (8-64). In the compounds, $R^{14}$ is alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine; and $X^{12}$ is —C≡N or —C≡C—C≡N.

(8-17) — (8-36)

(8-37) 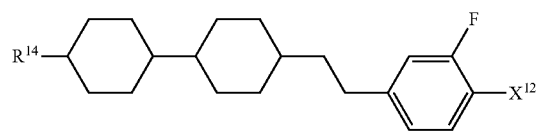
(8-38) 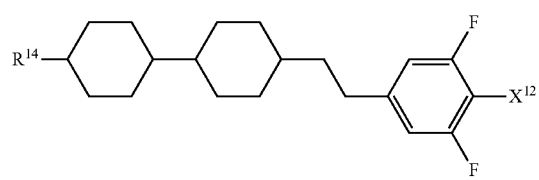
(8-39) 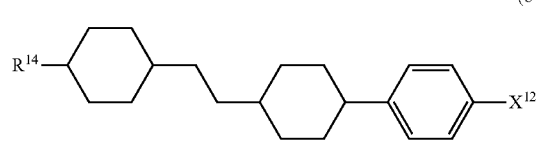
(8-40) 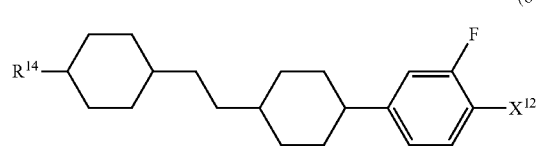
(8-41) 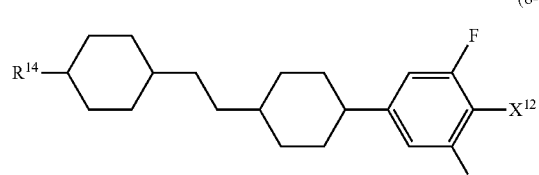
(8-42) 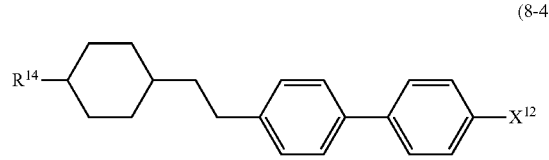
(8-43) 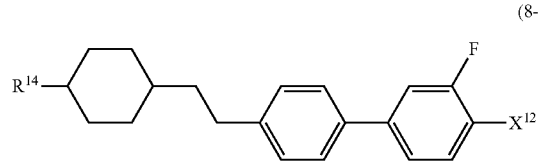
(8-44) 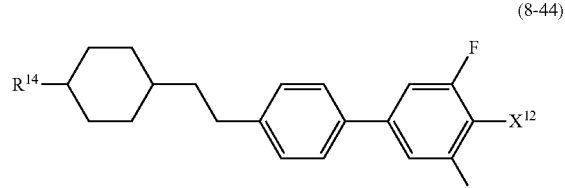
(8-45) 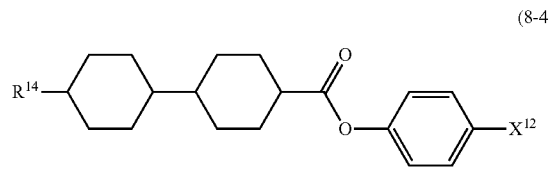
(8-46) 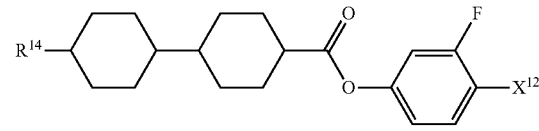
(8-47) 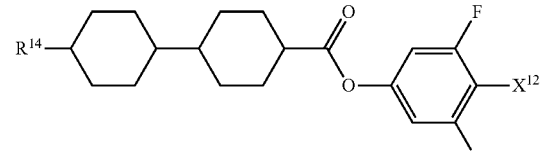
(8-48) 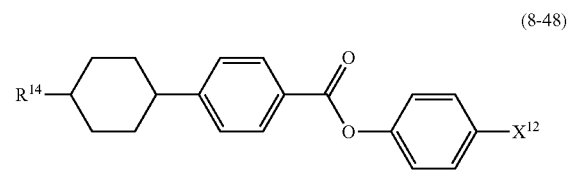
(8-49) 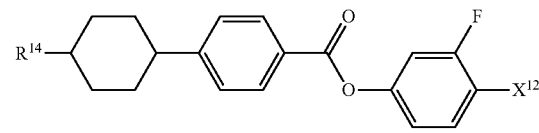
(8-50) 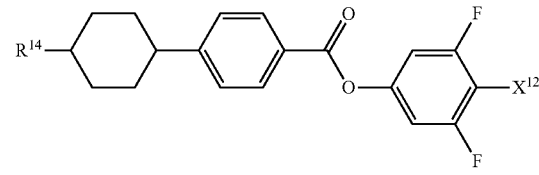
(8-51) 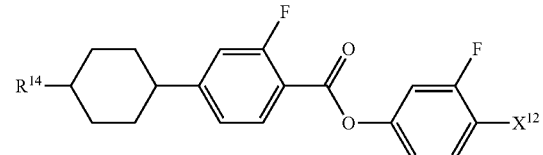
(8-52) 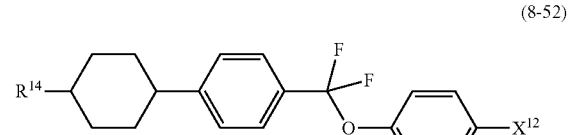
(8-53) 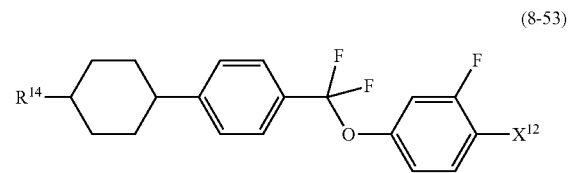
(8-54) 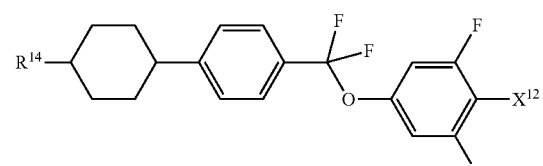

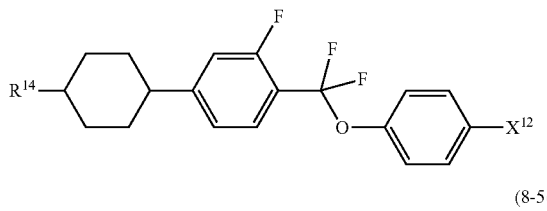
(8-55)

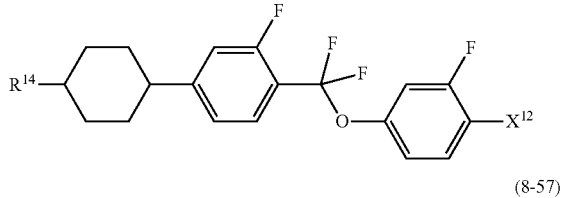
(8-56)

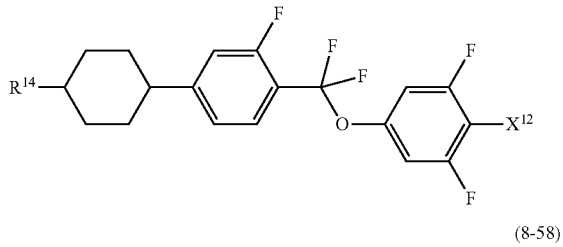
(8-57)

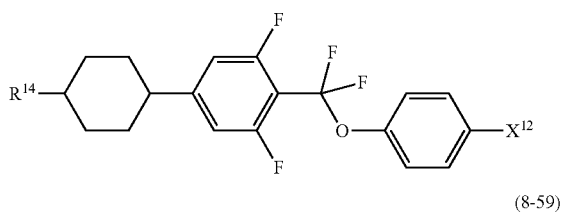
(8-58)

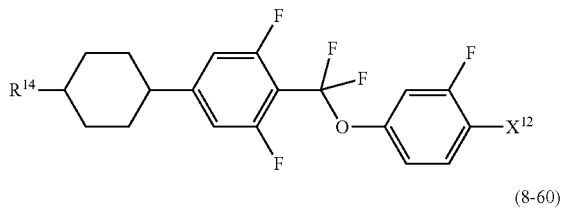
(8-59)

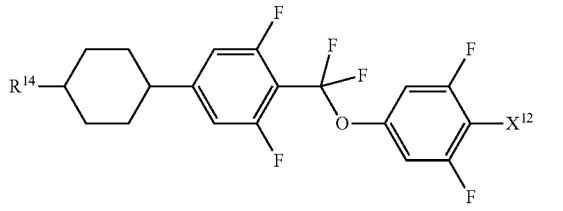
(8-60)

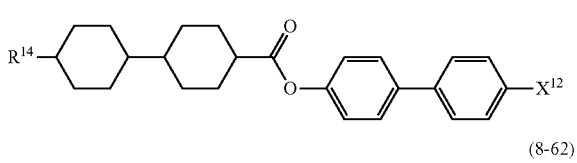
(8-61)

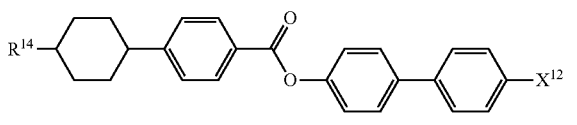
(8-62)

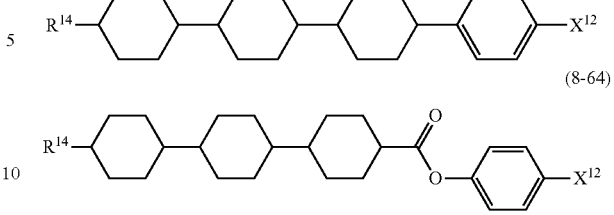
(8-63)

(8-64)

Component D has the positive dielectric anisotropy and a value thereof is large, and therefore is used when a composition for the TN mode or the like is prepared. Addition of component D can increase the dielectric anisotropy of the composition. Component D is effective in extending the temperature range of the liquid crystal phase, adjusting the viscosity or adjusting the optical anisotropy. Component D is also useful for adjustment of the voltage-transmittance curve of the device.

When a composition for the TN mode or the like is prepared, a content of component D is suitably in the range of approximately 1 to approximately 99% by weight, preferably in the range of approximately 10 to approximately 97% by weight, and further preferably in the range of approximately 40 to approximately 95% by weight, based on the weight of the liquid crystal composition. When component D is added to a composition having the negative dielectric anisotropy, the content of component D is preferably approximately 30% by weight or less. Addition of component D allows adjustment of the elastic constant of the composition and adjustment of the voltage-transmittance curve of the device.

Component E includes compounds (9) to (15). The compounds have phenylene in which hydrogen in lateral positions are replaced by two pieces of halogen, such as 2,3-difluoro-1,4-phenylene. Preferred examples of component E include compounds (9-1) to (9-8), compounds (10-1) to (10-17), compound (11-1), compounds (12-1) to (12-3), compounds (13-1) to (13-11), compounds (14-1) to (14-3) and compounds (15-1) to (15-3). In the compounds, $R^{15}$ and $R^{16}$ are independently alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine; and $R^{17}$ is hydrogen, fluorine, alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine.

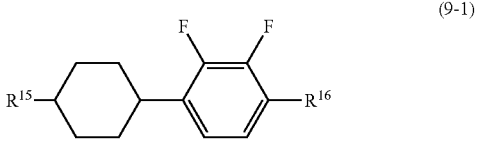
(9-1)

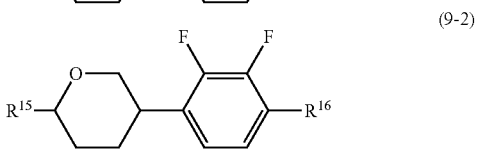
(9-2)

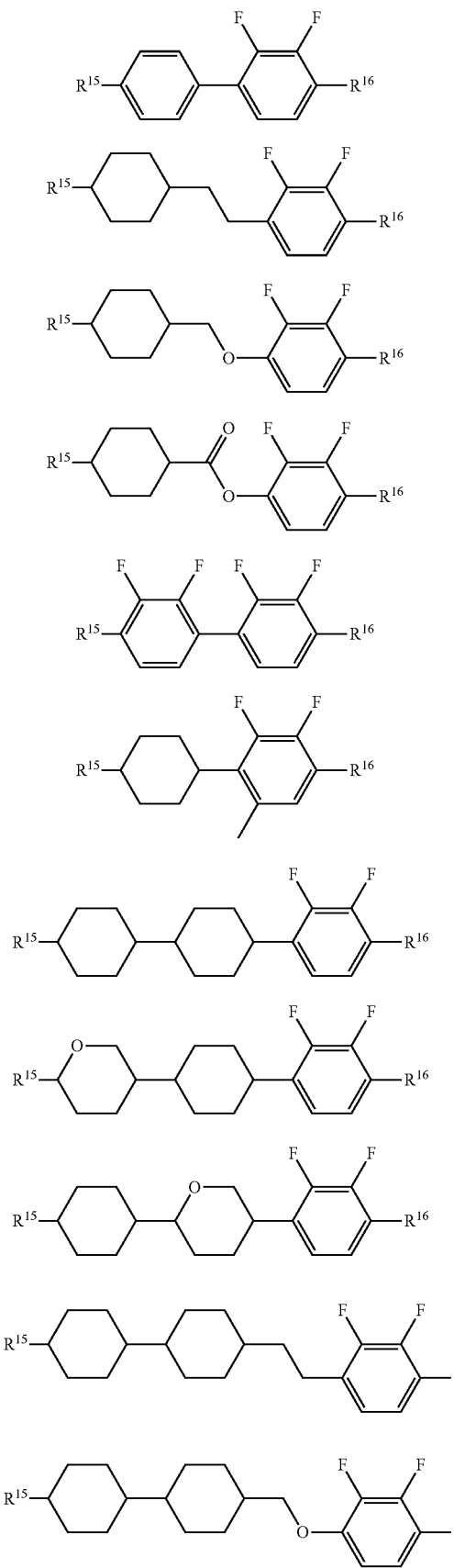
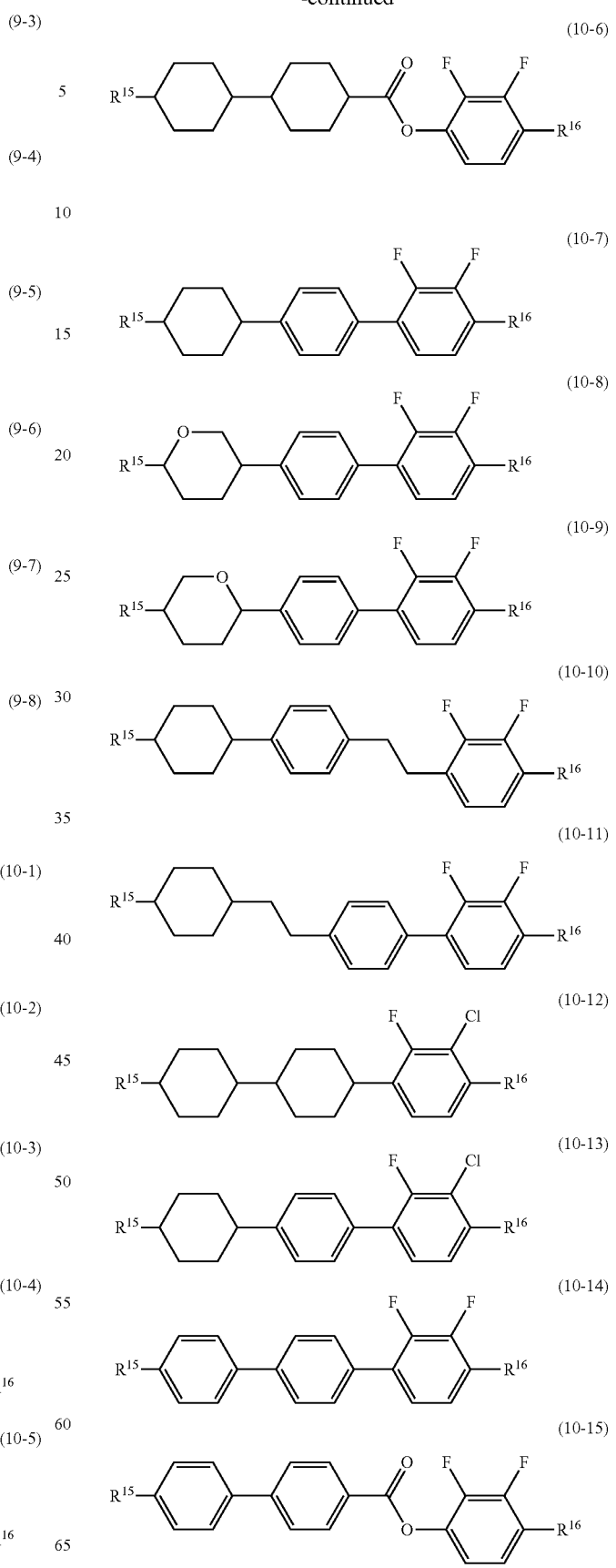

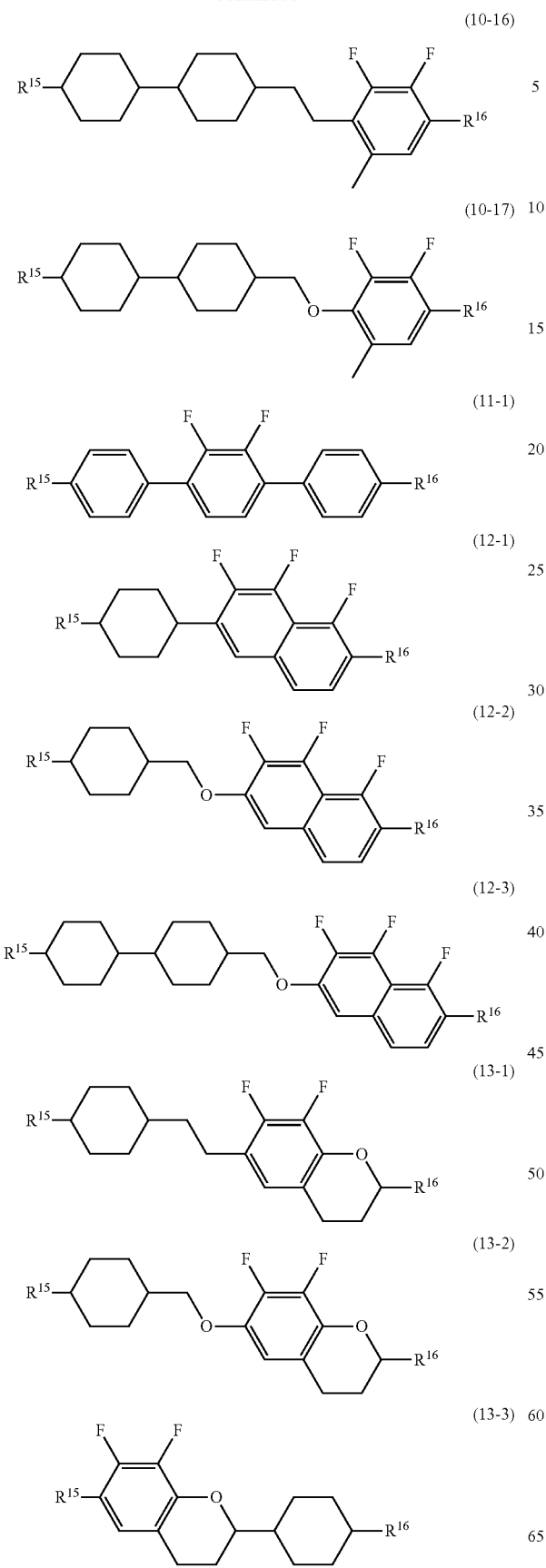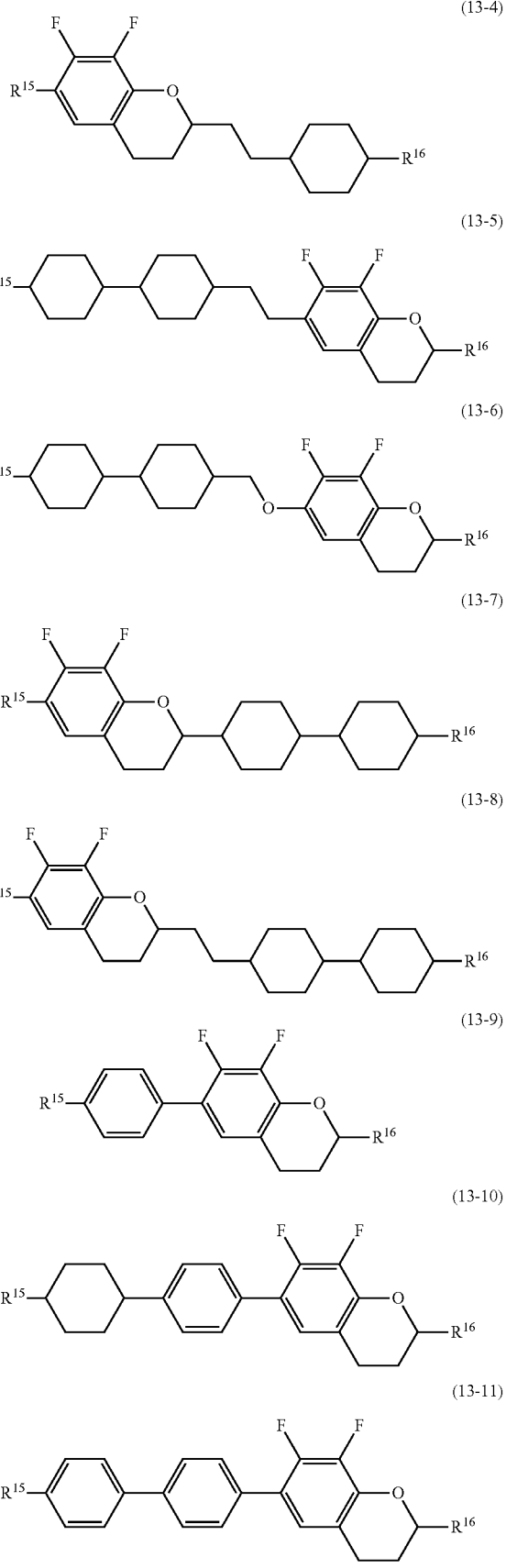

-continued

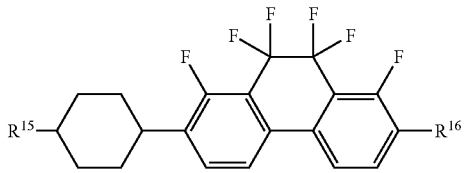
(14-1)

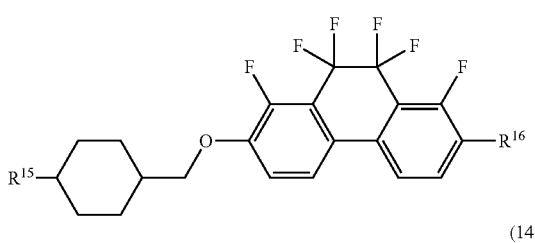
(14-2)

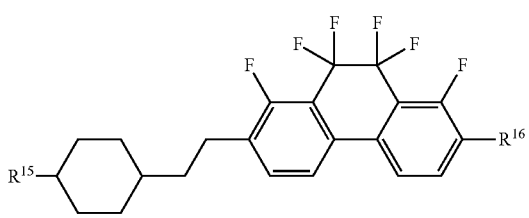
(14-3)

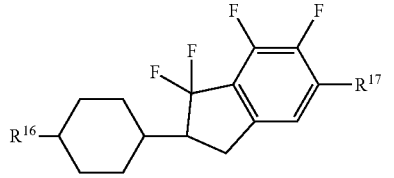
(15-1)

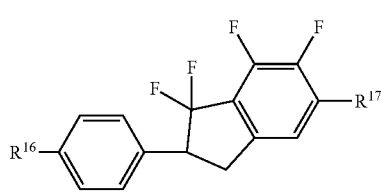
(15-2)

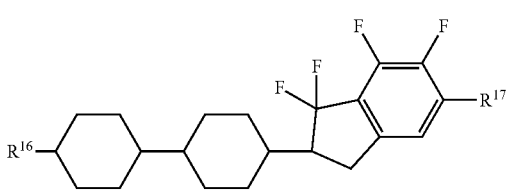
(15-3)

Component E has a negatively large dielectric anisotropy. Component E is used when a composition for the IPS mode, the VA mode, the PSA mode or the like is prepared. As a content of component E is increased, the dielectric anisotropy of the composition is negatively increased, but the viscosity is increased. Thus, as long as a desired value of threshold voltage of the device is met, the content is preferably as small as possible. When the dielectric anisotropy of about −5 is taken into consideration, the content is preferably approximately 40% by weight or more in order to allow a sufficient voltage driving.

Among types of component E, compound (9) is a bicyclic compound, and therefore is effective in decreasing the viscosity, adjusting the optical anisotropy or increasing the dielectric anisotropy. Compounds (10) and (11) are a tricyclic compound, and therefore are effective in increasing the maximum temperature, the optical anisotropy or the dielectric anisotropy. Compounds (12) to (15) are effective in increasing the dielectric anisotropy.

When a composition for the IPS mode, the VA mode or the PSA mode is prepared, the content of component E is preferably approximately 40% by weight or more, and further preferably in the range of approximately 50 to approximately 95% by weight, based on the weight of the liquid crystal composition. When component E is added to a composition having the positive dielectric anisotropy, the content of component E is preferably approximately 30% by weight or less. Addition of component E allows adjustment of the elastic constant of the composition and adjustment of the voltage-transmittance curve of the device.

The liquid crystal composition satisfying at least one of physical properties such as the high stability to heat and light, the high maximum temperature, the low minimum temperature, the small viscosity, the suitable optical anisotropy, the large dielectric anisotropy, the large specific resistance and the suitable elastic constant can be prepared by suitably combining components B, C, D and E described above. A liquid crystal compound different from components B, C, D and E may be added, when necessary.

3-2. Additive

A liquid crystal composition is prepared according to a known method. For example, the component compounds are mixed and dissolved in each other by heating. According to an application, an additive may be added to the composition. Specific examples of the additive include the polymerizable compound, the polymerization initiator, the polymerization inhibitor, the optically active compound, the antioxidant, the ultraviolet light absorber, the light stabilizer, the heat stabilizer, the dye and the antifoaming agent. Such additives are well known to those skilled in the art, and described in literature.

In a liquid crystal display device having the polymer sustained alignment (PSA) mode, the composition contains a polymer. The polymerizable compound is added for the purpose of forming the polymer in the composition. The polymerizable compound is polymerized by irradiation with ultraviolet light while voltage is applied between electrodes, and thus the polymer is formed in the composition. A suitable pretilt is achieved by the method, and therefore the device in which response time is shortened and image persistence is improved is prepared.

Preferred examples of the polymerizable compound include an acrylate, a methacrylate, a vinyl compound, a vinyloxy compound, a propenyl ether, an epoxy compound (oxirane, oxetane) and a vinyl ketone. Further preferred examples include a compound having at least one acryloyloxy, and a compound having at least one methacryloyloxy. The further preferred examples also include a compound having both acryloyloxy and methacryloyloxy.

Still further preferred examples include compounds (M-1) to (M-17). In the compounds, $R^{25}$ to $R^{31}$ are independently hydrogen or methyl; s, v and x are independently 0 or 1; and t and u are independently an integer from 1 to 10. $L^{21}$ to $L^{26}$ are independently hydrogen or fluorine; $L^{27}$ and $L^{28}$ are independently hydrogen, fluorine or methyl.

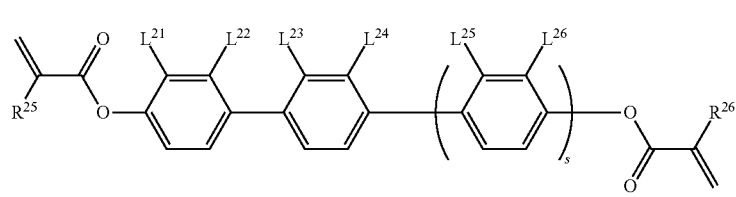
(M-1)
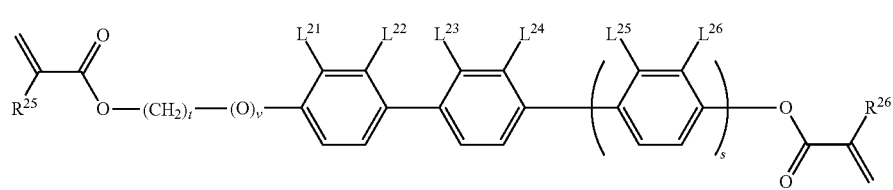
(M-2)
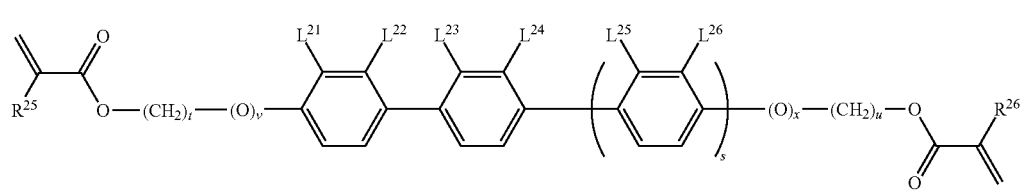
(M-3)
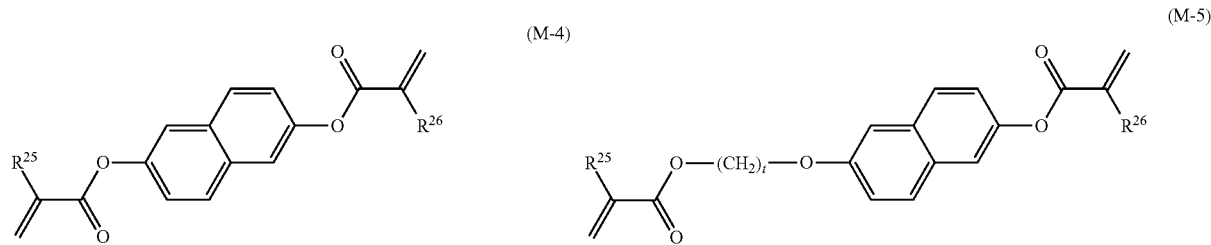
(M-4) (M-5)
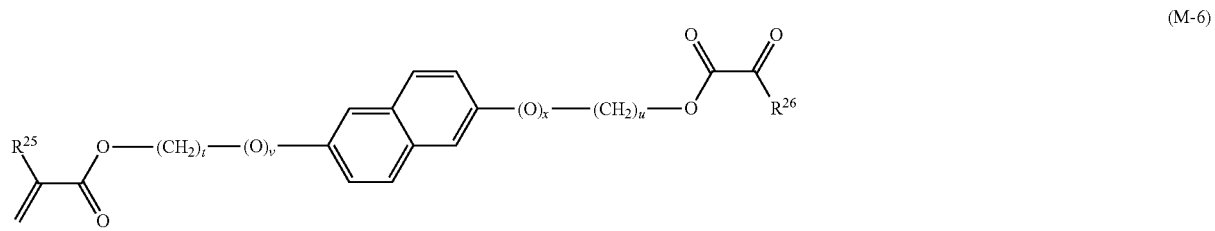
(M-6)
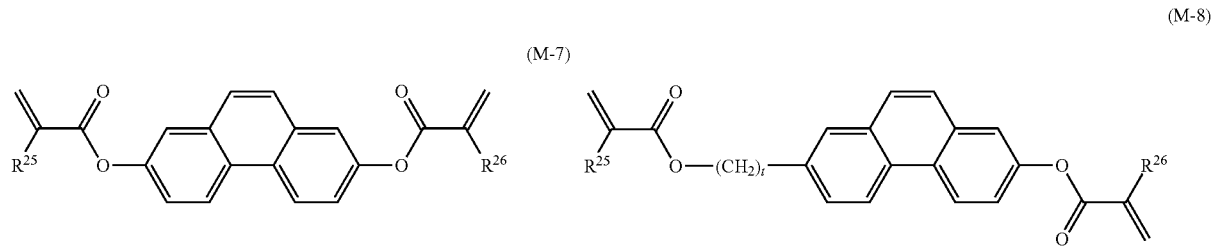
(M-7) (M-8)
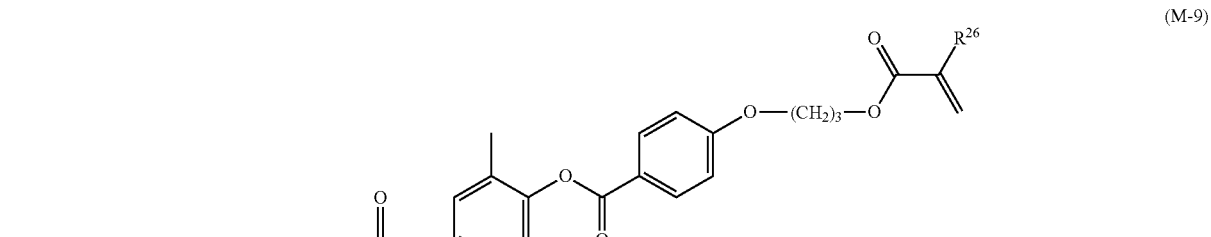
(M-9)

-continued
(M-10)
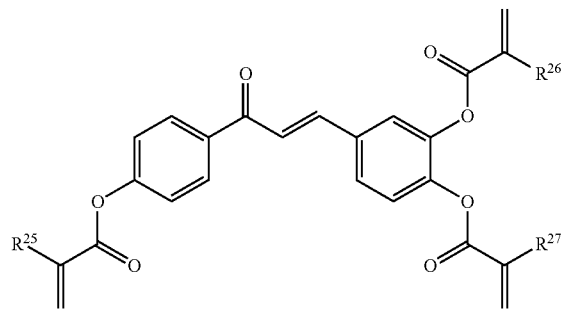
(M-11)
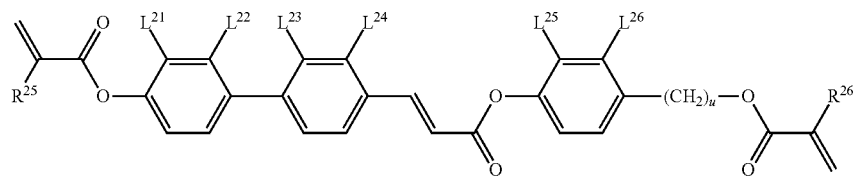
(M-12)
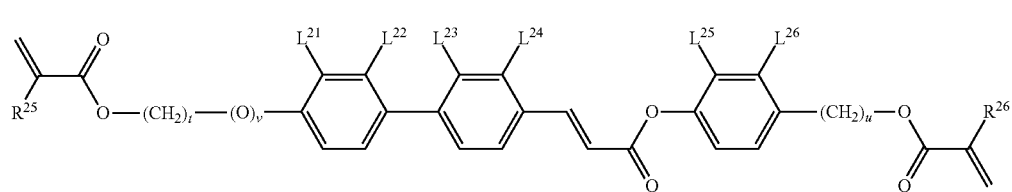
(M-13)
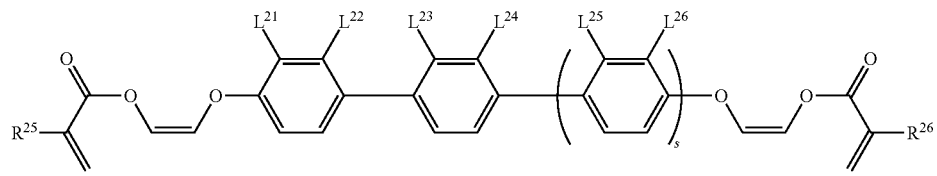
(M-14)
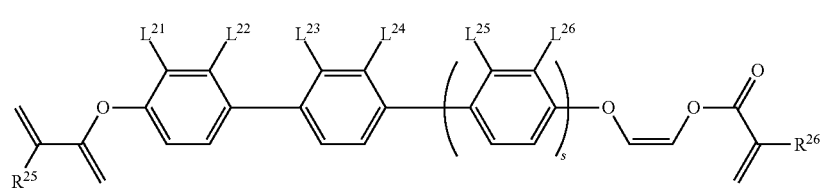
(M-15)
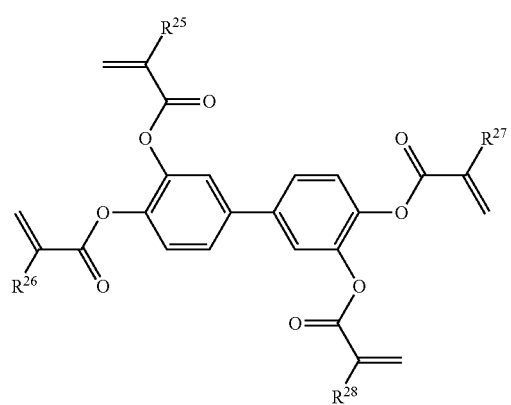
(M-16)
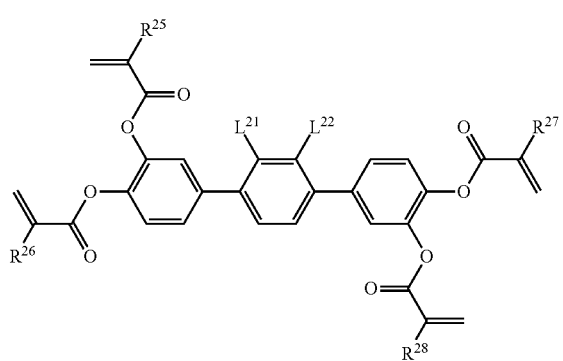

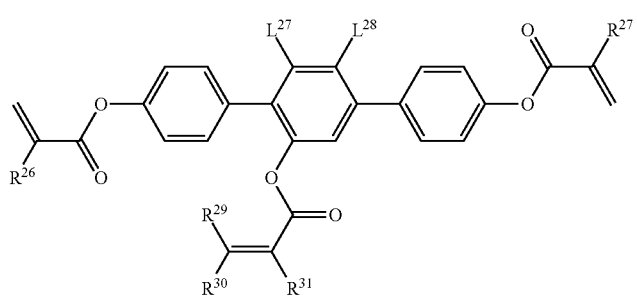

(M-17)

The polymerizable compound can be rapidly polymerized by adding the polymerization initiator. An amount of a remaining polymerizable compound can be decreased by optimizing reaction temperature. Specific examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone/Michler's ketone mixture, a hexaarylbiimidazole/mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a mixture of 2, 4-diethylxanthone and methyl p-dimethylaminobenzoate and a mixture of benzophenone and methyltriethanolamine.

After the photoradical polymerization initiator is added to the liquid crystal composition, polymerization can be performed by irradiation with ultraviolet light while an electric field is applied. However, an unreacted polymerization initiator or a decomposition product of the polymerization initiator may cause a poor display such as the image persistence in the device. In order to prevent such an event, photopolymerization may be performed without addition of the polymerization initiator. A preferred wavelength of irradiation light is in the range of approximately 150 to approximately 500 nanometers. A further preferred wavelength is in the range of approximately 250 to approximately 450 nanometers, and a most preferred wavelength is in the range of approximately 300 to approximately 400 nanometers.

Upon storing the polymerizable compound, the polymerization inhibitor may be added thereto in order to prevent polymerization. The polymerizable compound is ordinarily added to the composition without removing the polymerization inhibitor. Examples of the polymerization inhibitor include hydroquinone, a hydroquinone derivative such as methylhydroquinone, 4-t-butylcatechol, 4-methoxyphenol and phenothiazine.

The optically active compound is effective in inducing a helical structure in liquid crystal molecules to give a required twist angle, and thereby preventing a reverse twist. A helical pitch can be adjusted by adding the optically active compound thereto. Two or more optically active compounds may be added for the purpose of adjusting temperature dependence of the helical pitch. Preferred examples of the optically active compound include compounds (Op-1) to (Op-18) described below. In compound (Op-18), ring J is 1,4-cyclohexylene or 1,4-phenylene, and $R^{28}$ is alkyl having 1 to 10 carbons.

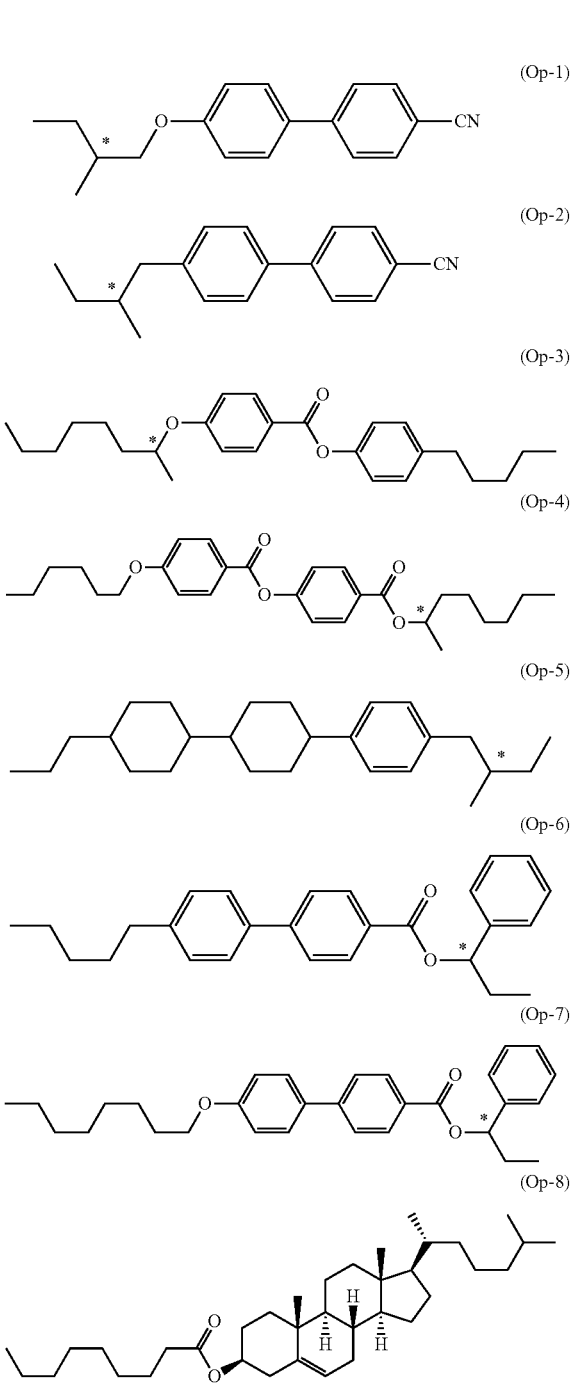

(Op-9)
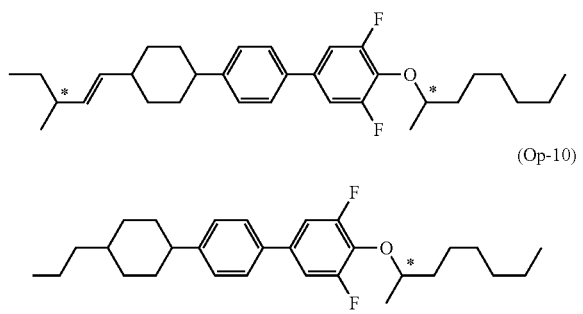
(Op-10)

(Op-11)

(Op-12)

(Op-13)
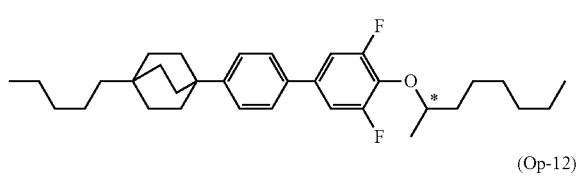
(Op-14)

(Op-15)
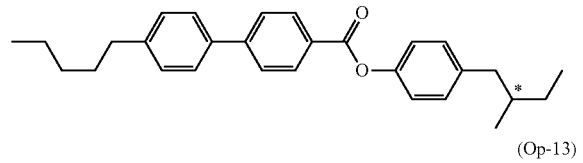
(Op-16)

(Op-17)
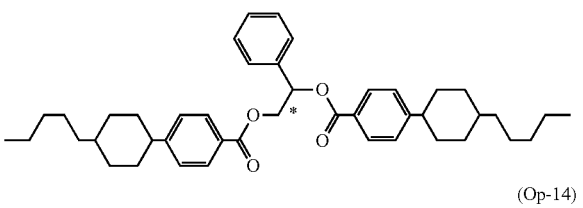

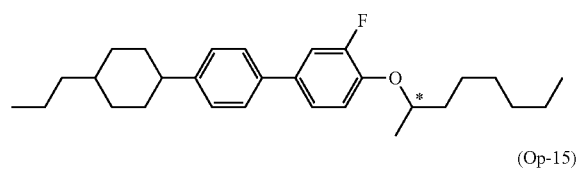

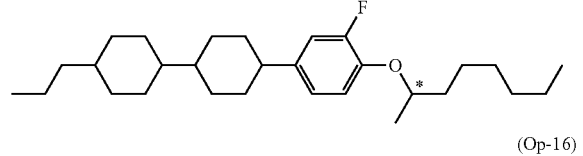

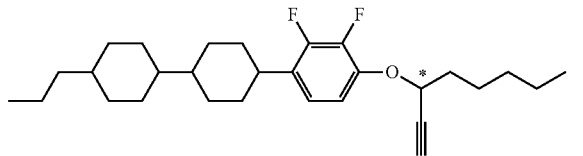

(Op-18)
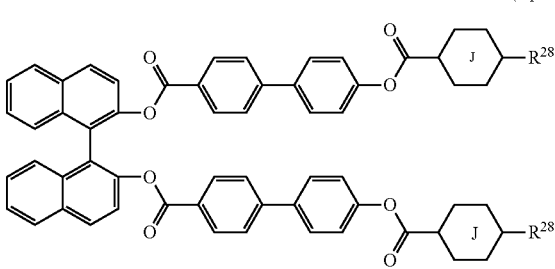

The antioxidant is effective for maintaining a large voltage holding ratio. Preferred examples of the antioxidant include compounds (AO-1) and (AO-2) described below; and Irganox 415, Irganox 565, Irganox 1010, Irganox 1035, Irganox 3114 and Irganox 1098 (trade names: BASF SE). The ultraviolet light absorber is effective in preventing a decrease of the maximum temperature. Preferred examples of the ultraviolet light absorber include a benzophenone derivative, a benzoate derivative and a triazole derivative. Specific examples include compounds (AO-3) and (AO-4) described below; TINUVIN 329, TINUVIN P, TINUVIN 326, TINUVIN 234, TINUVIN 213, TINUVIN 400, TINUVIN 328 and TINUVIN 99-2 (trade names: BASF SE); and 1,4-diazabicyclo[2.2.2]octane (DABCO).

The light stabilizer such as an amine having steric hindrance is preferred for maintaining the large voltage holding ratio. Preferred examples of the light stabilizer include compounds (AO-5) and (AO-6) described below; and TINUVIN 144, TINUVIN 765 and TINUVIN 770DF (trade names: BASF SE). The heat stabilizer is also effective for maintaining the large voltage holding ratio, and preferred examples include IRGAFOS 168 (trade name: BASF SE). A dichroic dye such as an azo dye or an anthraquinone dye is added to the composition to be adapted for a device having a guest host (GH) mode. The antifoaming agent is effective in preventing foam formation. Preferred examples of the antifoaming agent include dimethyl silicone oil and methylphenyl silicone oil.

(AO-1)
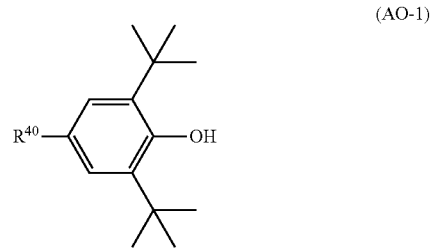

(AO-2)
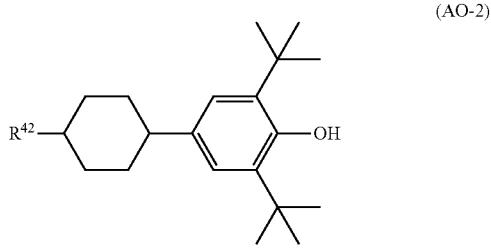

-continued

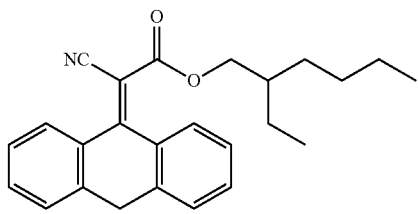
(AO-3)

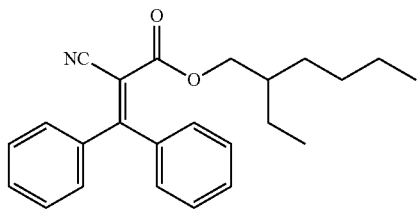
(AO-4)

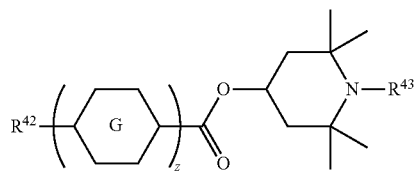
(AO-5)

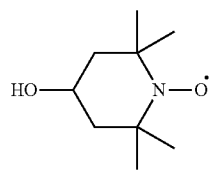
(AO-6)

In compound (AO-1), $R^{40}$ is alkyl having 1 to 20 carbons, alkoxy having 1 to 20 carbons, —COOR$^{41}$ or —CH$_2$CH$_2$COOR$^{41}$, in which $R^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl or O. (oxygen radical); ring G is 1,4-cyclohexylene or 1,4-phenylene; and z is 1, 2 or 3.

4. Liquid Crystal Display Device

The liquid crystal composition can be used in the liquid crystal display device having an operating mode such as the PC mode, the TN mode, the STN mode, the OCB mode and the PSA mode, and driven by an active matrix. The composition can also be used in the liquid crystal display device having the operating mode such as the PC mode, the TN mode, the STN mode, the OCB mode, the VA mode and the IPS mode, and driven by a passive matrix mode. The devices can be applied to any of a reflective type, a transmissive type and a transflective type.

The composition is also suitable for a nematic curvilinear aligned phase (NCAP) device, and the composition is microencapsulated herein. The composition can also be used in a polymer dispersed liquid crystal display device (PDLCD) and a polymer network liquid crystal display device (PN-LCD). In the compositions, a lot of polymerizable compounds are added. On the other hand, when an amount of adding the polymerizable compound is approximately 10% by weight or less based on the weight of the liquid crystal composition, the liquid crystal display device having the PSA mode can be prepared. A preferred proportion is in the range of approximately 0.1 to approximately 2% by weight. A further preferred proportion is in the range of approximately 0.2 to approximately 1.0% by weight. The device having the PSA mode can be driven by the driving mode such as an active matrix mode and a passive matrix mode. Such devices can be applied to any of the reflective type, the transmissive type and the transflective type.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in more detail by way of Examples (including Synthesis Examples and Composition Examples). The invention is not limited by the Examples. The invention includes a mixture of a composition in Composition Example 1 and a composition in Composition Example 2. The invention also includes a composition prepared by mixing at least two compositions in Composition Examples.

1. Example of Compound (1)

Compound (1) was prepared according to procedures described below. A compound prepared was identified by a method such as an NMR analysis. Physical properties of the compound and the composition and characteristics of a device were measured by methods described below.

NMR analysis: For measurement, DRX-500 made by Bruker BioSpin Corporation was used. In $^1$H-NMR measurement, a sample was dissolved in a deuterated solvent such as CDCl$_3$, and measurement was carried out under conditions of room temperature, 500 MHz and 16 times of accumulation. Tetramethylsilane was used as an internal standard. In $^{19}$F-NMR measurement, CFCl$_3$ was used as an internal standard, and measurement was carried out under conditions of 24 times of accumulation. In the explanation of a nuclear magnetic resonance spectrum, s, d, t, q, quin, sex, m and br stand for a singlet, a doublet, a triplet, a quartet, a quintet, a sextet, a multiplet and being broad, respectively.

Gas chromatographic analysis: For measurement, GC-2010 Gas Chromatograph made by Shimadzu Corporation was used for measurement. As a column, a capillary column DB-1 (length 60 m, bore 0.25 mm, film thickness 0.25 μm) made by Agilent Technologies, Inc. was used. As a carrier gas, helium (1 mL/minute) was used. A temperature of a sample vaporizing chamber and a detector (FID) part were set to 300° C. and 300° C., respectively. A sample was dissolved in acetone and prepared to be a 1 weight % solution, and then 1 microliter of the solution obtained was injected into the sample vaporizing chamber. As a recorder, GC Solution System made by Shimadzu Corporation or the like was used.

HPLC analysis: For measurement, Prominence (LC-20AD; SPD-20A) made by Shimadzu Corporation was used. As a column, YMC-Pack ODS-A (length 150 mm, bore 4.6 mm, particle diameter 5 μm) made by YMC Co., Ltd. was used. As an eluate, acetonitrile and water were appropriately mixed and used. As a detector, a UV detector, an RI detector, a CORONA detector or the like was appropriately used. When the UV detector was used, a detection wavelength was set at 254 nanometers. A sample was dissolved in acetonitrile to prepare a 0.1 wt % solution, and 1 microliter of the solution obtained was introduced into a sample chamber. As a recorder, C-R7Aplus made by Shimadzu Corporation was used.

Ultraviolet-Visible spectrophotometry: For measurement, PharmaSpec UV-1700 made by Shimadzu Corporation was used. A detection wavelength was adjusted in the range of 190 nanometers to 700 nanometers. A sample was dissolved in acetonitrile and prepared to be a solution of 0.01 millimole per liter, and measurement was carried out by putting the solution in a quartz cell (optical path length 1 cm).

Sample for measurement: When phase structure and transition temperature (a clearing point, a melting point, a polymerization starting temperature or the like) were measured, a compound per se was used as a sample. When physical properties such as a maximum temperature of a nematic phase, viscosity, optical anisotropy, and dielectric anisotropy were measured, a mixture of a compound and a base liquid crystal was used as a sample.

When the sample prepared by mixing the compound with the base liquid crystal was used, an extrapolated value was calculated according to the following formula: [extrapolated value]=(100×[measured value of a sample]−[% by weight of a base liquid crystal]×[measured value of the base liquid crystal])/[% by weight of a compound], and the calculated value was described.

Base liquid crystal (A): When the dielectric anisotropy of the compound was zero or positive, base liquid crystal (A) described below was used. A proportion of each component was expressed in terms of % by weight.

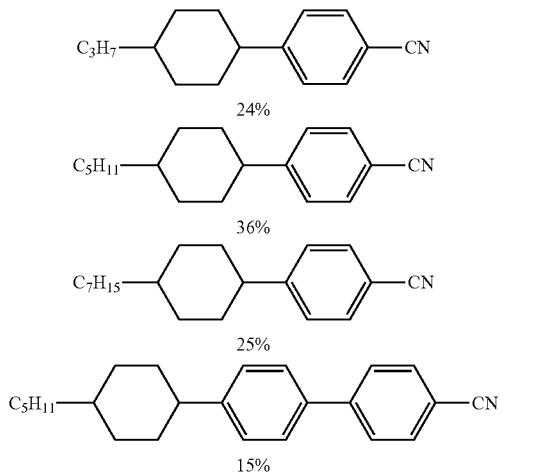

A ratio of the compound to base liquid crystal (A) was adjusted to (15% by weight:85% by weight). When crystals (or a smectic phase) precipitated at 25° C. at the ratio, a ratio of the compound to base liquid crystal (A) was changed in the order of (10% by weight:90% by weight), (5% by weight:95% by weight) and (1% by weight:99% by weight), and the sample was measured at a ratio at which no crystal (or no smectic phase) precipitated at 25° C. In addition, unless otherwise noted, the ratio of the compound to base liquid crystal (A) was (15% by weight:85% by weight).

Base liquid crystal (B): In Comparative Example 2, base liquid crystal (B) having a fluorine-based compound described below was also used as a component. A proportion of a component of base liquid crystal (B) was expressed in terms of % by weight.

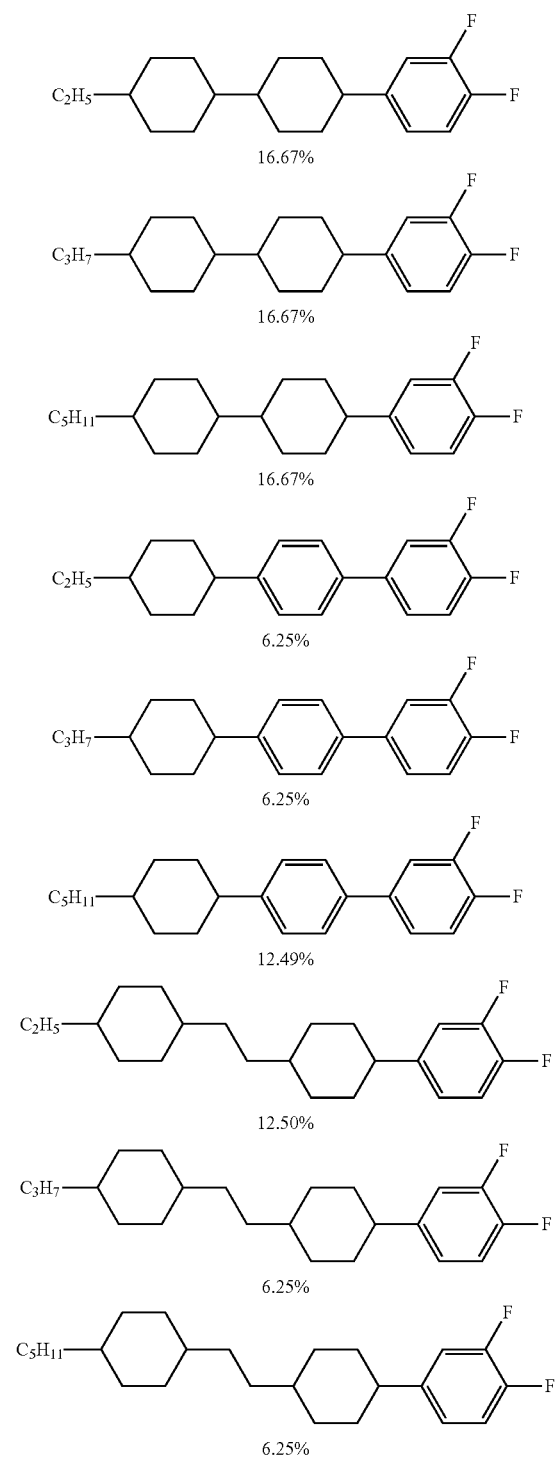

A ratio of the compound to base liquid crystal (B) was adjusted to (20% by weight:80% by weight). When crystals (or a smectic phase) precipitated at 25° C. at the ratio, a ratio of the compound to base liquid crystal (B) was changed in the order of (15% by weight:85% by weight), (10% by weight:90% by weight), (5% by weight:95% by weight) and (1% by weight:99% by weight), and physical properties of the sample were measured at a ratio at which no crystal (or no smectic phase) precipitated at 25° C. In addition, unless otherwise noted, the ratio of the compound to base liquid crystal (B) was (20% by weight:80% by weight).

Measuring method: Physical properties were measured according to methods described below. Most of the methods are described in the Standard of Japan Electronics and Information Technology Industries Association (hereinafter, abbreviated as JEITA) discussed and established in JEITA (JEITA ED-2521B). A modified method was also applied. No thin film transistor (TFT) was attached to a TN device used for measurement.

(1) Phase structure: A sample was placed on a hot plate of a melting point apparatus (FP-52 Hot Stage made by Mettler-Toledo International Inc.) equipped with a polarizing microscope. A state of phase and a change thereof were observed with the polarizing microscope while the sample was heated at a rate of 3° C. per minute, and a kind of the phase was specified.

(2) Transition temperature (° C.): For measurement, a scanning calorimeter, Diamond DSC System, made by PerkinElmer, Inc., or a high-sensitivity differential scanning calorimeter, X-DSC7000, made by SII NanoTechnology Inc. was used. A sample was heated and then cooled at a rate of 3° C. per minute, and a starting point of an endothermic peak or an exothermic peak as caused by a phase change of the sample was determined by extrapolation, and thus a transition temperature was determined. A polymerization starting temperature and a melting point of a compound were also measured using the apparatus. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to liquid may be occasionally abbreviated as "clearing point."

A crystal was expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Compatibility at low temperature: Samples in which the base liquid crystal and the compound were mixed for proportions of the compounds to be 20% by weight, 15% by weight, 10% by weight, 5% by weight, 3% by weight and 1% by weight were prepared, and placed in glass vials. After the glass vials were kept in freezers at −10° C. or −20° C. for a predetermined period of time, whether or not crystals or a smectic phase precipitated was observed.

(4) Maximum temperature of nematic phase ($T_{NI}$ or NI; ° C.): A sample was placed on a hot plate of a melting point apparatus equipped with a polarizing microscope, and was heated at a rate of 1° C. per minute. Temperature when part of the sample began to change from a nematic phase to an isotropic liquid was measured. When the sample was a mixture of compound (1) and the base liquid crystal, the maximum temperature was expressed as a symbol $T_{NI}$. When the sample was a mixture of compound (1) and a compound such as component B, C and D, the maximum temperature was expressed as a symbol NI. A higher limit of a temperature range of the nematic phase may be occasionally abbreviated as "maximum temperature."

(5) Minimum temperature of nematic phase ($T_C$; ° C.): Samples each having a nematic phase were put in glass vials and kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_C$ was expressed as $T_C$<−20° C. A lower limit of the temperature range of the nematic phase may be occasionally abbreviated as "minimum temperature."

(6) Viscosity (bulk viscosity; η; measured at 20° C.; mPa·s): A cone-plate (E type) rotational viscometer made by Tokyo Keiki Inc. was used for measurement.

(7) Viscosity (rotational viscosity; γ1; measured at 25° C.; mPa·s): Measurement was carried out according to the method described in M. Imai et al., Molecular Crystals and Liquid Crystals, Vol. 259, 37 (1995). A sample was put in a TN device in which a twist angle was 0 degrees and a distance between two glass substrates (cell gap) was 5 micrometers. Voltage was applied stepwise to the device in the range of 16 V to 19.5 V at an increment of 0.5 V. After 0.2 second without voltage application, voltage was applied repeatedly under conditions of only one rectangular wave (rectangular pulse; 0.2 second) and no voltage application (2 seconds). A peak current and a peak time of a transient current generated by the applied voltage were measured. A value of rotational viscosity was obtained from the measured values according to calculating equation (8) on page 40 of the paper presented by M. Imai et al. A value of a dielectric anisotropy required for the calculation was determined using the device in which the rotational viscosity was measured and by a method described below.

(8) Optical anisotropy (refractive index anisotropy; measured at 25° C.; Δn): Measurement was carried out by an Abbe refractometer having a polarizing plate mounted on an ocular, using light at a wavelength of 589 nanometers. A surface of a main prism was rubbed in one direction, and then a sample was added dropwise onto the main prism. A refractive index (n∥) was measured when a direction of polarized light was parallel to a direction of rubbing. A refractive index (n⊥) was measured when a direction of polarized light was perpendicular to a direction of rubbing. A value of optical anisotropy was calculated from an equation: Δn=n∥−n⊥.

(9) Dielectric anisotropy (Δ∈; measured at 25° C.): A sample was put in a TN device in which a distance between two glass substrates (cell gap) was 9 micrometers and a twist angle was 80 degrees. Sine waves (10 V, 1 kHz) were applied to the device, and after 2 seconds, a dielectric constant (∈∥) of liquid crystal molecules in a major axis direction was measured. Sine waves (0.5 V, 1 kHz) were applied to the device, and after 2 seconds, a dielectric constant (∈⊥) of the liquid crystal molecules in a minor axis direction was measured. A value of dielectric anisotropy was calculated from an equation: Δ∈=∈∥−∈⊥.

(10) Elastic constant (K; measured at 25° C.; pN): For measurement, HP4284A LCR Meter made by Yokogawa-Hewlett-Packard Co. was used. A sample was put in a horizontal alignment device in which a distance between two glass substrates (cell gap) was 20 micrometers. An electric charge of 0 V to 20 V was applied to the device, and electrostatic capacity and applied voltage were measured. Measured values of electrostatic capacity (C) and applied voltage (V) were fitted to equation (2.98) and equation (2.101) on page 75 of "Liquid Crystal Device Handbook"

(Ekisho Debaisu Handobukku in Japanese; The Nikkan Kogyo Shimbun, Ltd.) and values of $K_{11}$ and $K_{33}$ were obtained from equation (2.99). Next, $K_{22}$ was calculated using the previously determined values of $K_{11}$ and $K_{33}$ in formula (3.18) on page 171. Elastic constant K was expressed using a mean value of the thus determined $K_{11}$, $K_{22}$ and $K_{33}$.

(11) Threshold voltage (Vth; measured at 25° C.; V): For measurement, An LCD-5100 luminance meter made by Otsuka Electronics Co., Ltd. was used. A light source was a halogen lamp. A sample was put in a normally white mode TN device in which a distance between two glass substrates (cell gap) was 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage was expressed in terms of voltage at 90% transmittance.

(12) Voltage holding ratio (VHR-1; measured at 25° C.; %): A TN device used for measurement had a polyimide alignment film and a distance between two glass substrates (cell gap) was 5 micrometers. A sample was put in the device, and then the device was sealed with an ultraviolet-curable adhesive. The device was charged by applying a pulse voltage (60 microseconds at 5 V) at 25° C. A decaying voltage was measured for 16.7 milliseconds with a high-speed voltmeter, and area A between a voltage curve and a horizontal axis in a unit cycle was determined. Area B was an area without decay. A voltage holding ratio was expressed in terms of a percentage of area A to area B.

(13) Voltage holding ratio (VHR-2; measured at 80° C.; %): A voltage holding ratio was measured by a method described above except that the voltage holding ratio was measured at 80° C. in place of 25° C. The results obtained were expressed in terms of a symbol VHR-2.

(14) Specific resistance (p; measured at 25° C.; Ωcm): Into a vessel equipped with electrodes, 1.0 milliliter of a sample was injected. A DC voltage (10 V) was applied to the vessel, and a DC current after 10 seconds was measured. A specific resistance was calculated from the following equation: (specific resistance)={(voltage)×(electric capacity of a vessel)}/{(direct current)×(dielectric constant of vacuum)}.

(15) Response time (τ; measured at 25° C.; ms): For measurement, An LCD-5100 luminance meter made by Otsuka Electronics Co., Ltd. was used. A light source was a halogen lamp. A low-pass filter was set to 5 kHz. A sample was put in a normally white mode TN device in which a distance between two glass substrates (cell gap) was 5.0 micrometers and a twist angle was 80 degrees. Rectangular waves (60 Hz, 5 V, 0.5 second) were applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A rise time (τr: rise time; millisecond) was a period of time required for a change in transmittance from 90% to 10%. A fall time (τf: fall time; millisecond) was a period of time required for a change in transmittance from 10% to 90%. A response time was expressed by a sum of the rise time and the fall time thus obtained.

Raw material: Solmix (registered trade name) A-11 is a mixture of ethanol (85.5%), methanol (13.4%) and isopropanol (1.1%), and was purchased from Japan Alcohol Trading Co., Ltd.

Synthesis Example 1

Synthesis of Compound (No. 99)

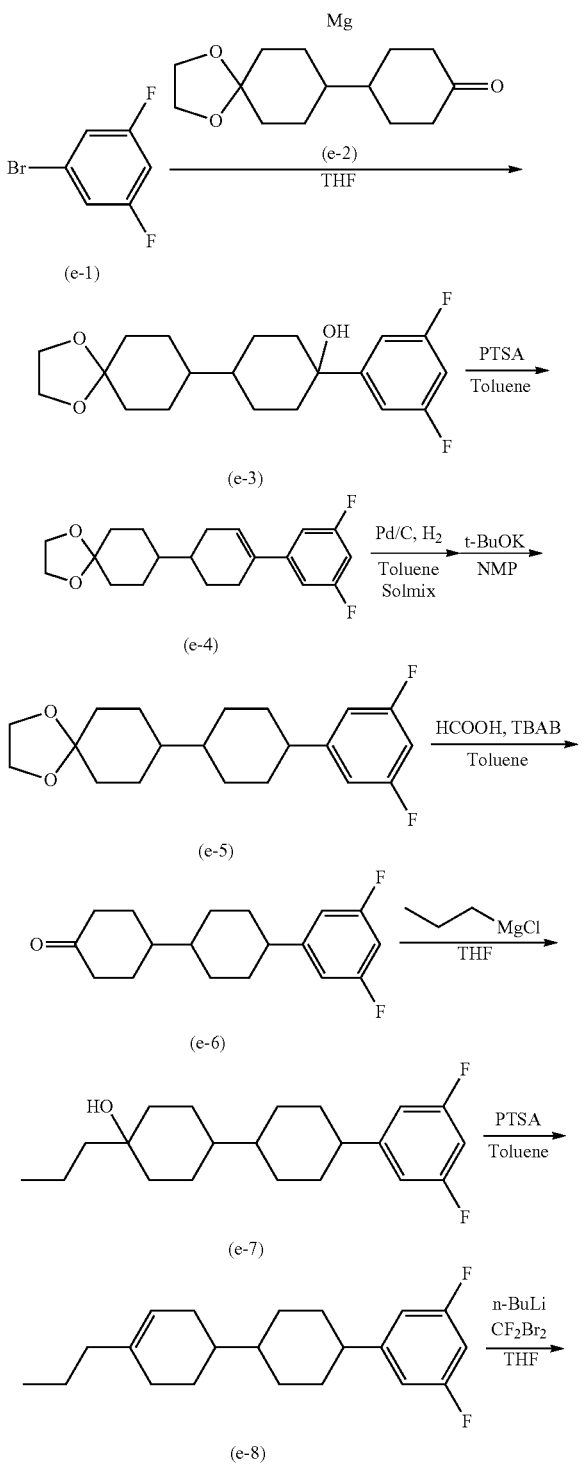

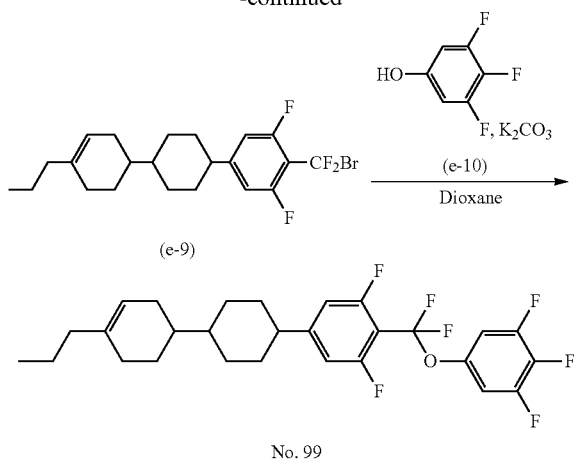

First Step

To a THF suspension (10 mL) of magnesium (4.5 g, 186.5 mmol), a THF solution (90 mL) of compound (e-1) (30.0 g, 155.5 mmol) was slowly added dropwise while liquid temperature was kept at 50° C. or less. To a Grignard reagent cooled in a water bath, a THF solution (80 mL) of compound (e-2) (40.8 g, 171.0 mmol) was slowly added dropwise while liquid temperature was kept at 50° C. or less. The resulting reaction mixture was stirred at room temperature for 1 hour and then quenched by an ammonium chloride solution, and the resulting mixture was subjected to extraction with ethyl acetate (400 mL). Combined organic layers were washed with water and saturated brine, and dried over anhydrous magnesium sulfate, and then a solvent was distilled off to obtain compound (e-3) (48.4 g, 137.4 mmol).

Second Step

Under a nitrogen atmosphere, compound (e-3) (48.4 g, 137.4 mmol) and p-toluenesulfonic acid monohydrate (PTSA) (0.6 g, 3.2 mmol) were added to toluene (180 mL), and the resulting mixture was heated and refluxed for 17 hours. The resulting reaction mixture was returned to 25° C. and poured into water (200 mL). The resulting mixture was subjected to extraction with toluene (100 mL). The resulting extract was washed with saturated brine, and dried over anhydrous magnesium sulfate. The resulting solution was concentrated under reduced pressure, and the residue was purified by silica gel chromatography (toluene:ethyl acetate=20:1 in a volume ratio) to obtain compound (e-4) (35.3 g, 104.9 mmol).

Third Step

In a mixed solvent of toluene (100 mL) and Solmix A-11 (100 mL), compound (e-4) (35.3 g, 104.9 mmol) was dissolved, Pd/C (1.8 g) was further added thereto, and the resulting mixture was stirred at room temperature under a hydrogen atmosphere. After no absorption of hydrogen was caused, Pd/C was eliminated, the solvent was further distilled off. The residue was purified by silica gel chromatography (toluene:ethyl acetate=20:1 in a volume ratio). The resulting compound was dissolved in N-methylpyrrolidone (NMP; 100 mL), and t-BuOK (13.8 g, 123.2 mmol) was added thereto, and the resulting mixture was stirred at room temperature for 24 hours. The resulting reaction mixture was poured into water (200 mL), and the resulting mixture was subjected to extraction with toluene (200 mL). The resulting extract was washed with saturated brine, and dried over anhydrous magnesium sulfate. The resulting solution was concentrated under reduced pressure, and the residue was purified by silica gel chromatography (toluene:ethyl acetate=20:1 in a volume ratio). The residue was further purified by recrystallization (2-propanol) to obtain compound (e-5) (19.5 g, 58.0 mmol).

Fourth Step

Under a nitrogen atmosphere, compound (e-5) (19.5 g, 58.0 mmol) and tetrabutylammonium bromide (TBAB) (3.7 g, 11.6 mmol) were added to a mixed solvent of formic acid (100 mL) and toluene (100 mL), and the resulting mixture was stirred at room temperature for 24 hours. Water (100 mL) was added thereto and the resulting mixture was neutralized with sodium hydrogen carbonate. The resulting reaction mixture was subjected to extraction with toluene (100 mL). The resulting extract was washed with saturated brine, and dried over anhydrous magnesium sulfate. The resulting solution was concentrated under reduced pressure, and the residue was purified by silica gel chromatography (toluene:ethyl acetate=10:1 in a volume ratio). The residue was further purified by recrystallization (heptane:toluene=1:1 in a volume ratio) to obtain compound (e-6) (15.7 g, 53.6 mmol).

Fifth Step

Under a nitrogen atmosphere, a THF solution (2.0 mol/L, 29.5 mL) of propylmagnesium chloride was cooled to 0° C. in an ice bath. A THF (30 mL) solution of compound (e-6) (15.7 g, 53.6 mmol) was added dropwise thereto. The resulting mixture was returned to room temperature, and then further stirred for 15 hours. The resulting mixture was quenched by a 1 N HCl aqueous solution and then subjected to extraction with ethyl acetate (150 mL). The resulting extract was washed with saturated brine, and dried over anhydrous magnesium sulfate. The resulting solution was concentrated under reduced pressure, and the residue was purified by silica gel chromatography (toluene:ethyl acetate=20:1 in a volume ratio) to obtain compound (e-7) (17.4 g, 51.7 mmol).

Sixth Step

Under a nitrogen atmosphere, a mixture of compound (e-7) (17.4 g, 51.7 mmol), PTSA (0.1 g, 0.6 mmol) and toluene (60 mL) was heated and refluxed for 17 hours. The resulting reaction mixture was returned to 25° C. and poured into water (100 mL), and the resulting mixture was subjected to extraction with toluene (50 mL). The resulting extract was washed with saturated brine, and dried over anhydrous magnesium sulfate. The resulting solution was concentrated under reduced pressure, and the residue was purified by silica gel chromatography (heptane) to obtain compound (e-8) (12.6 g, 39.7 mmol).

Seventh Step

Under a nitrogen atmosphere, compound (e-8) (12.6 g, 39.7 mmol) and THF (100 mL) were put in a reaction vessel, and the resulting mixture was cooled to −74° C. Thereto, n-butyllithium (1.60 M; n-hexane solution; 29.7 mL) was added dropwise in the temperature range of −74° C. to −70° C., and the resulting mixture was further stirred for 60 minutes. Subsequently, a THF (10.0 mL) solution of dibromodifluoromethane (9.9 g, 47.4 mmol) was added dropwise thereto in the temperature range of −75° C. to −70° C., and the resulting mixture was stirred for 1 hour. The resulting reaction mixture was returned to 25° C. and quenched with an ammonium chloride solution, and the aqueous layer was subjected to extraction with toluene (200 mL). Combined organic layers were washed with brine, and dried over anhydrous magnesium sulfate. The resulting solution was concentrated under reduced pressure, and the residue was purified by silica gel chromatography (heptane) to obtain compound (e-9) (14.4 g, 32.1 mmol).

Eighth Step

Under a nitrogen atmosphere, compound (e-10) (3.6 g, 24.1 mmol), potassium carbonate (13.3 g, 96.4 mmol) and dioxane (50 mL) were put in a reaction vessel, and the resulting mixture was heated to 90° C. and stirred for 0.5 hour. Subsequently, a dioxane solution (50 mL) of compound (e-9) (14.4 g, 32.1 mmol) was added dropwise thereto, and the resulting mixture was further stirred at 100° C. for 7 hours. The resulting reaction mixture was cooled to 25° C. and then poured into water, and the resulting aqueous layer was subjected to extraction with toluene. Then, combined organic layers were washed with water, and dried over anhydrous magnesium sulfate. The resulting solution was concentrated under reduced pressure, and the resulting residue was purified by silica gel chromatography (heptane). The residue was further purified by recrystallization (heptane:Solmix A-11=1:1 in a volume ratio) to obtain compound (No. 99) (7.8 g, 15.1 mmol).

$^1$H-NMR (δ ppm; CDCl$_3$): 6.96 (dd, 2H), 6.83 (d, 2H), 5.41-5.36 (m, 1H), 2.50-2.46 (m, 1H), 2.08-1.76 (m, 7H), 1.46-1.09 (m, 13H), 0.88 (t, 3H).

Physical properties of compound (No. 99) were as described below. Transition temperature: C 71.7 C 76.1 N 111.5 I. $T_{NI}$=79.0° C.; η=60.5 mPa·s; Δn=0.097; Δε=25.4.

Synthesis Example 2

Synthesis of Compound (No. 147)

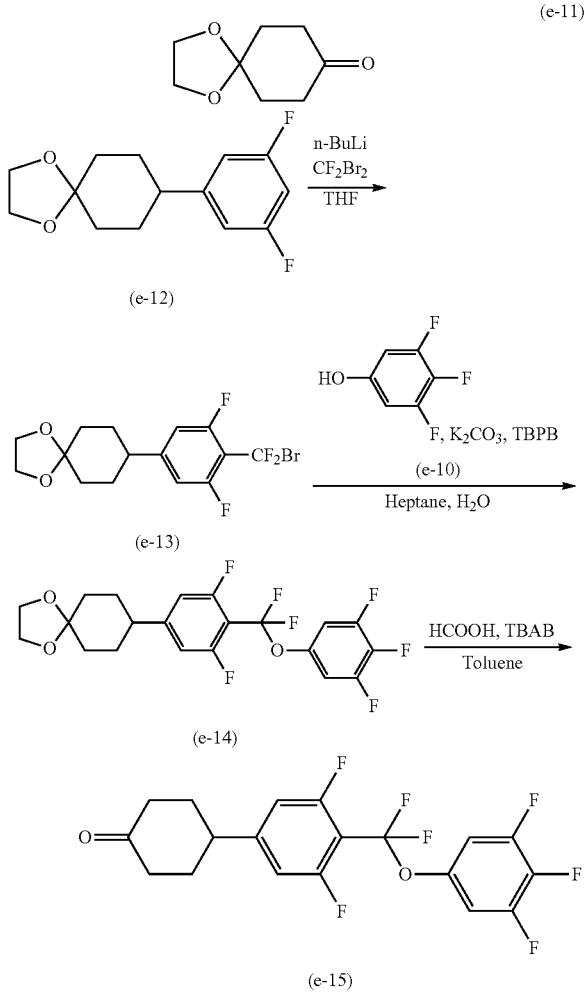

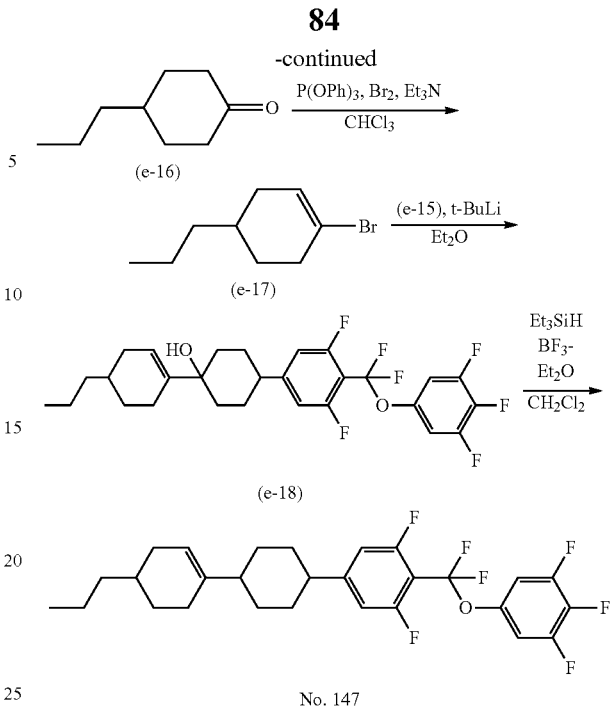

No. 147

First Step

Compound (e-12) was obtained by performing synthesis up to the third step in a manner similar to the operations in Synthesis Example 1 by using compound (e-11) in place of compound (e-2) in the first step in Synthesis Example 1. Under a nitrogen atmosphere, compound (e-12) (26.8 g, 105.4 mmol) and THF (270 mL) were put in a reaction vessel, and the resulting mixture was cooled to −74° C. Thereto, n-butyllithium (1.65 M; n-hexane solution; 83.0 mL) was added dropwise in the temperature range of −74° C. to −70° C., and the resulting mixture was further stirred for 60 minutes. Subsequently, a THF (30.0 mL) solution of dibromodifluoromethane (31.0 g, 147.6 mmol) was added dropwise thereto in the temperature range of −75° C. to −70° C., and the resulting mixture was stirred for 1 hour. The resulting reaction mixture was returned to 25° C. and quenched by an ammonium chloride solution, and the resulting aqueous layer was subjected to extraction with toluene (600 mL). Combined organic layers were washed with brine, and dried over anhydrous magnesium sulfate. The resulting solution was concentrated under reduced pressure, and the residue was purified by silica gel chromatography (toluene: ethyl acetate=10:1 in a volume ratio) to obtain compound (e-13) (34.2 g, 89.3 mmol).

Second Step

Under a nitrogen atmosphere, compound (e-13) (34.2 g, 89.3 mmol), compound (e-10) (15.9 g, 107.1 mmol), potassium carbonate (14.8 g, 107.1 mmol), tetrabutyl phosphonium bromide (TBPB) (18.2 g, 53.6 mmol), heptane (35 mL) and water (310 mL) were put in a reaction vessel, and the resulting mixture was heated and refluxed until compound (e-13) disappeared. The resulting reaction mixture was cooled to 25° C. and then poured into water, and the resulting aqueous layer was subjected to extraction with toluene. Combined organic layers were washed with water, and dried over anhydrous magnesium sulfate. The resulting solution was concentrated under reduced pressure, and the residue was purified by silica gel chromatography (toluene: ethyl acetate=10:1 in a volume ratio) to obtain compound (e-14) (24.3 g, 54.0 mmol).

Third Step

Under a nitrogen atmosphere, compound (e-14) (24.3 g, 54.0 mmol) and tetrabutylammonium bromide (TBAB) (3.5 g, 10.8 mmol) were added to a mixed solvent of formic acid (73 mL) and toluene (240 mL), and the resulting mixture was stirred at room temperature for 24 hours. Water (100 mL) was added thereto and the resulting mixture was neutralized with sodium hydrogen carbonate. The resulting reaction mixture was subjected to extraction with toluene (100 mL). The resulting extract was washed with saturated brine, and dried over anhydrous magnesium sulfate. The resulting solution was concentrated under reduced pressure, and the residue was purified by recrystallization (heptane:toluene=1:1 in a volume ratio) to obtain compound (e-15) (14.9 g, 36.7 mmol).

Fourth Step

Under a nitrogen atmosphere, triphenyl phosphite (48.9 g, 156.9 mmol) and chloroform (100 mL) were put into a reaction vessel, and the resulting mixture was cooled to −74° C. Thereto, bromine (27.4 g, 171.2 mmol) was added dropwise in the temperature range of −74° C. to −70° C., and the resulting mixture was further stirred for 60 minutes. Subsequently, triethylamine (18.8 g, 185.4 mmol) was added dropwise thereto in the temperature range of −74° C. to −70° C., and the resulting mixture was stirred for 1 hour. Further, compound (e-16) (20.0 g, 142.6 mmol) was added dropwise thereto in the temperature range of −74° C. to −70° C., and the resulting mixture was stirred for 1 hour. The resulting reaction mixture was returned to 25° C., and heated and refluxed for 2 hours. The resulting reaction mixture was returned to 25° C., water (100 mL) was added thereto, and the resulting aqueous layer was subjected to extraction with chloroform (100 mL). Combined organic layers were washed with brine, and dried over anhydrous magnesium sulfate. The resulting solution was concentrated under reduced pressure, the residue was purified by silica gel chromatography (heptane) to obtain compound (e-17) (25.0 g, 123.1 mmol).

Fifth Step

Under a nitrogen atmosphere, compound (e-17) (3.0 g, 14.8 mmol) and diethyl ether (40 mL) were put in a reaction vessel, and the resulting mixture was cooled to −20° C. Thereto, t-butyllithium (1.90 M; n-hexane solution; 18.1 mL) was added dropwise in the temperature range of −22° C. to −20° C. The resulting reaction mixture was stirred at 0° C. for 2 hours. Subsequently, a diethyl ether (10.0 mL) solution of compound (e-15) (4.0 g, 9.9 mmol) was added dropwise thereto in the temperature range of −5° C. to 5° C., and the resulting mixture was stirred for 1 hour. The resulting reaction mixture was returned to 25° C. and quenched with an ammonium chloride solution, and the resulting aqueous layer was subjected to extraction with toluene (300 mL). Combined organic layers were washed with brine, and dried over anhydrous magnesium sulfate. The resulting solution was concentrated under reduced pressure, and the residue was purified by silica gel chromatography (toluene:ethyl acetate=10:1 in a volume ratio) to obtain compound (e-18) (4.8 g, 9.1 mmol).

Sixth Step

Under a nitrogen atmosphere, compound (e-18) (4.8 g, 9.1 mmol), triethylsilane (1.6 g, 13.6 mmol) and dichloromethane (50 mL) were put in a reaction vessel, and the resulting mixture was cooled to −60° C. Thereto, a boron trifluoride-diethylether complex (1.9 g, 13.6 mmol) was added dropwise in the temperature range of −64° C. to −58° C., and the resulting mixture was further stirred for 60 minutes. The resulting reaction mixture was returned to 25° C., water (100 mL) was adder thereto, and the resulting aqueous layer was subjected to extraction with dichloromethane (50 mL). Combined organic layers were washed with brine, and dried over anhydrous magnesium sulfate. The resulting solution was concentrated under reduced pressure, and the residue was purified by silica gel chromatography (toluene:heptane=1:1 in a volume ratio). The residue was further purified by recrystallization (Solmix A-11) to obtain compound (No. 147) (0.8 g, 1.6 mmol).

$^1$H-NMR (δ ppm; CDCl$_3$): 6.96 (dd, 2H), 6.84 (d, 2H), 5.40 (s, 1H), 2.52-2.51 (m, 1H), 2.12-1.60 (m, 10H), 1.52-1.14 (m, 10H), 0.89 (t, 3H).

Physical properties of compound (No. 147) were as described below. Transition temperature: C 71.7 C 8.1 C 72.6 N 112.2 I. $T_{NI}$=77.0° C.; η=60.5 mPa·s; Δn=0.104; Δ∈=24.2.

Comparative Example 1

Comparison of Dielectric Anisotropy

For comparison, compound (I) was selected. The reason is that the compound is included in compound (3-2) described in JP H10-204436 A, and similar to the compound of the invention.

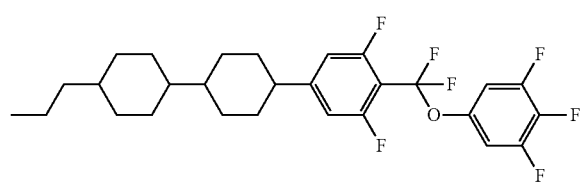

(I)

$^1$H-NMR (δ ppm; CDCl$_3$): 6.95 (dd, 2H), 6.83 (d, 2H), 2.48-2.43 (m, 1H), 1.92-1.85 (m, 4H), 1.78-1.71 (m, 4H), 1.38-1.25 (m, 4H), 1.16-0.95 (m, 9H), 0.89-0.86 (m, 5H).

Physical properties of comparative compound (I) were as described below. Transition temperature: C 84.3 N 165.5 I. $T_{NI}$=112.4° C.; η=62.4 mPa·s; Δn=0.112; Δ∈=21.2.

TABLE 1

Physical properties of compound (No. 99) and comparative compound (I)

| Compound | Compound (No. 99) | Comparative compound (I) |
|---|---|---|
| Maximum temperature ($T_{NI}$) | 79.0° C. | 112.4° C. |
| Dielectric anisotropy ($\Delta\epsilon$) | 25.4 | 21.2 |
| Optical anisotropy ($\Delta n$) | 0.097 | 0.112 |
| Viscosity ($\eta$) | 60.5 mPa·s | 62.4 mPa·s |

Physical properties of compound (No. 99) obtained in Synthesis Example 1 and comparative compound (I) are summarized in Table 1. Table 1 shows that compound (No. 99) is superior in view of a larger dielectric anisotropy.

Comparative Example 2

Comparison of Compatibility at Low Temperature

Composition (X-1) was prepared from 15% by weight of compound (No. 99) and 85% by weight of base liquid crystal (A). Composition (X-1) (0.5 mL) and a glass capillary were put in a 10 mL-vial, and the vial was capped under a nitrogen flow. A cap part was well-closed with a parafilm, and then the vial was stored in a freezer at −20° C. Next, composition (X-2) was prepared from 10% by weight of compound (No. 99) and 90% by weight of base liquid crystal (B). The composition was well-closed in a vial in a similar procedure as described above, and the vial was stored in the freezer at −20° C. When two compositions were observed after 30 days, the compositions maintained a nematic phase, and neither emergence of a smectic phase nor precipitation of crystals were confirmable.

Composition (X-3) was prepared from 15% by weight of comparative compound (S-1) and 85% by weight of base liquid crystal (A). Composition (X-4) was prepared from 10% by weight of comparative compound (S-1) and 90% by weight of base liquid crystal (B). When composition (X-3) and composition (X-4) were stored in the freezer at −20° C. in a similar procedure as described above, precipitation of crystals was confirmed after 8 days in composition (X-3). Moreover, precipitation of crystals was confirmed after 10 days in composition (X-4).

Results described above are summarized in Table 2. The liquid crystal composition containing compound (No. 99) of the invention can maintain the nematic phase even under a low temperature. The compound of the invention has excellent compatibility with other liquid crystal compounds, and therefore can be concluded to be significantly useful.

TABLE 2

Comparison of compatibility at low temperature

| Sample for measurement | Components of sample | | Conditions (−20° C., 30 days) |
|---|---|---|---|
| Composition (X-1) | 15% by weight of compound (No. 99) | 85% by weight of base liquid crystal (A) | Nematic phase was maintained. |
| Composition (X-2) | 10% by weight of compound (No. 99) | 90% by weight of base liquid crystal (B) | Nematic phase was maintained. |
| Composition (X-3) | 15% by weight of comparative compound (I) | 85% by weight of base liquid crystal (A) | Crystals precipitated after 8 days. |
| Composition (X-4) | 10% by weight of comparative compound (I) | 90% by weight of base liquid crystal (B) | Crystals precipitated after 10 days. |

Compounds (No. 1) to (No. 240) shown below can be prepared in a manner similar to the synthesis method described in Synthesis Example 1. Attached data shows values obtained according to the measurement methods described above. The transition temperature is a measured value of the compound per se, and the maximum temperature ($T_{NI}$), the dielectric anisotropy ($\Delta\epsilon$) and the optical anisotropy ($\Delta n$) are physical property values each obtained by converting, according to the extrapolation method as described above, a measured value of the sample in which the compound was mixed with base liquid crystal (A).

| No. | |
|---|---|
| 1 | 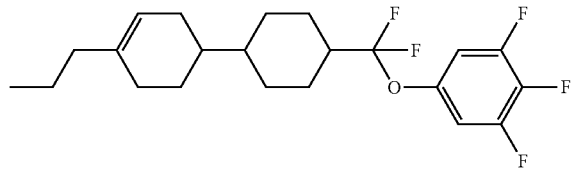 [SMILES: CCCC1=CCC(C2CCC(C(F)(F)Oc3cc(F)c(F)c(F)c3)CC2)CC1] |
| 2 | 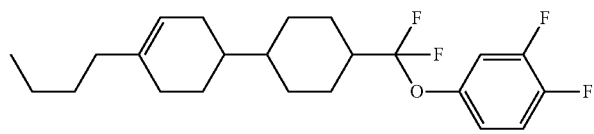 [SMILES: CCCCC1=CCC(C2CCC(C(F)(F)Oc3ccc(F)c(F)c3)CC2)CC1] |
| 3 | 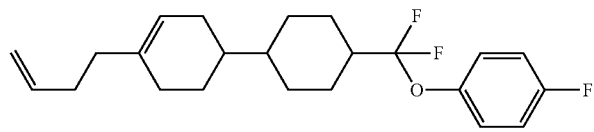 |
| 4 | 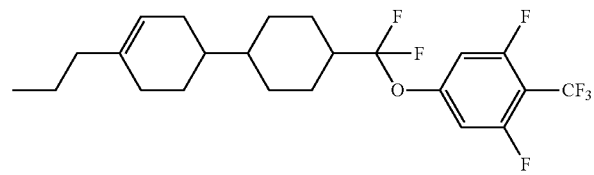 [SMILES: CCCC1=CCC(C2CCC(C(F)(F)Oc3cc(F)c(C(F)(F)F)c(F)c3)CC2)CC1] |
| 5 | 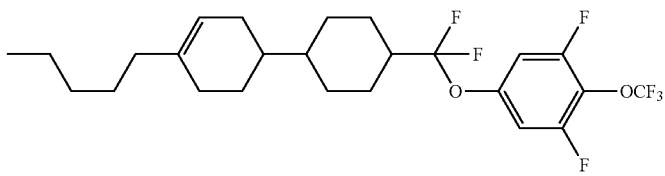 [SMILES: CCCCCC1=CCC(C2CCC(C(F)(F)Oc3cc(F)c(OC(F)(F)F)c(F)c3)CC2)CC1] |
| 6 | 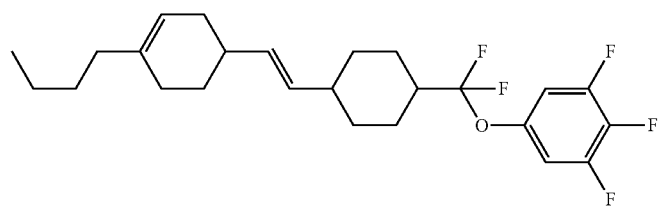 [SMILES: CCCCC1=CCC(/C=C/C2CCC(C(F)(F)Oc3cc(F)c(F)c(F)c3)CC2)CC1] |
| 7 | 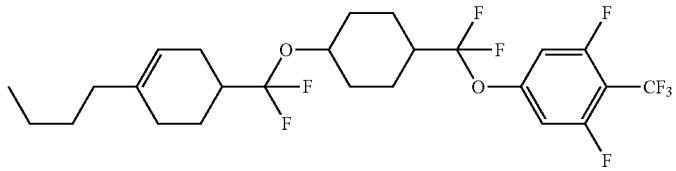 [SMILES: CCCCC1=CCC(C(F)(F)OC2CCC(C(F)(F)Oc3cc(F)c(C(F)(F)F)c(F)c3)CC2)CC1] |
| 8 | 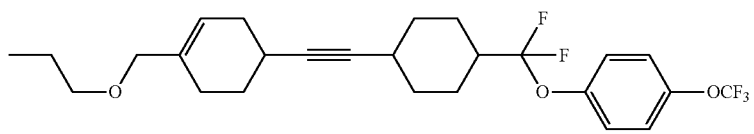 [SMILES: CCCOCC1=CCC(C#CC2CCC(C(F)(F)Oc3ccc(OC(F)(F)F)cc3)CC2)CC1] |
| 9 | 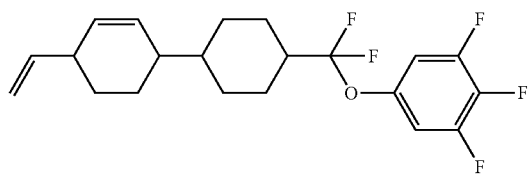 [SMILES: C=CC1C=CC(C2CCC(C(F)(F)Oc3cc(F)c(F)c(F)c3)CC2)CC1] |

-continued
| No. | |
|---|---|
| 10 | 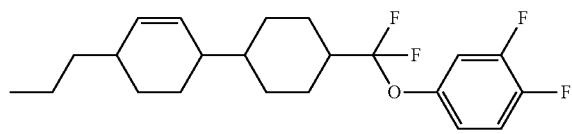 [SMILES: CCCC1C=CC(C2CCC(C(F)(F)Oc3ccc(F)c(F)c3)CC2)CC1] |
| 11 | 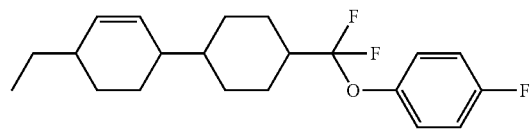 |
| 12 | 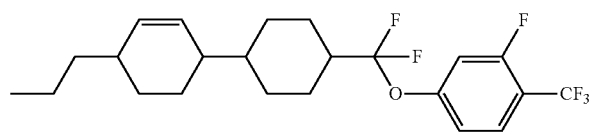 [SMILES: CCCC1C=CC(C2CCC(C(F)(F)Oc3ccc(C(F)(F)F)c(F)c3)CC2)CC1] |
| 13 | 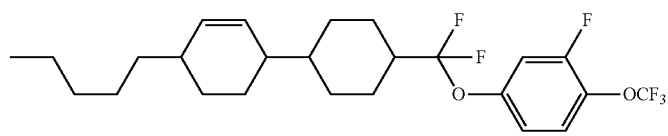 [SMILES: CCCCCC1C=CC(C2CCC(C(F)(F)Oc3ccc(OC(F)(F)F)c(F)c3)CC2)CC1] |
| 14 | 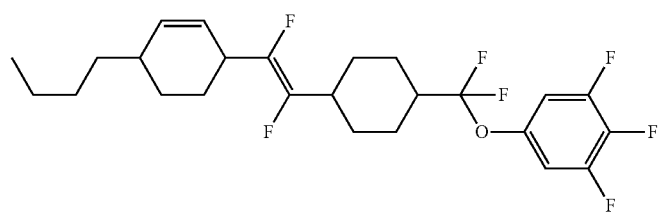 [SMILES: CCCCC1C=CC(/C(F)=C(\F)C2CCC(C(F)(F)Oc3cc(F)c(F)c(F)c3)CC2)CC1] |
| 15 | 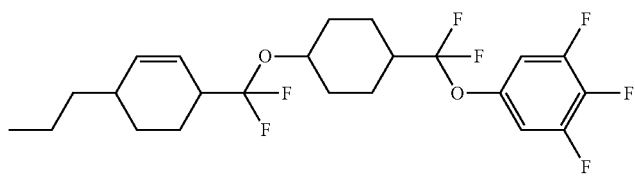 [SMILES: CCCC1C=CC(C(F)(F)OC2CCC(C(F)(F)Oc3cc(F)c(F)c(F)c3)CC2)CC1] |
| 16 | 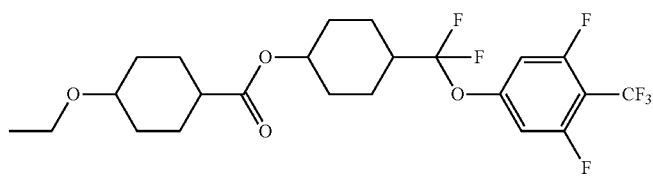 [SMILES: CCOC1CCC(C(=O)OC2CCC(C(F)(F)Oc3cc(F)c(C(F)(F)F)c(F)c3)CC2)CC1] |
| 17 | 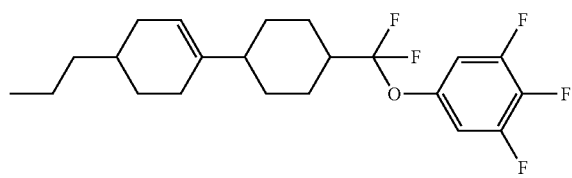 |
| 18 | 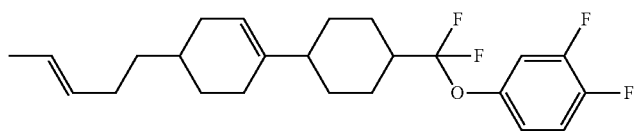 [SMILES: C/C=C/CCC1CC=C(C2CCC(C(F)(F)Oc3ccc(F)c(F)c3)CC2)CC1] |
| 19 | 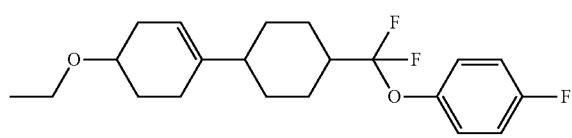 [SMILES: CCOC1CC=C(C2CCC(C(F)(F)Oc3ccc(F)cc3)CC2)CC1] |

| No. | |
|---|---|
| 20 | 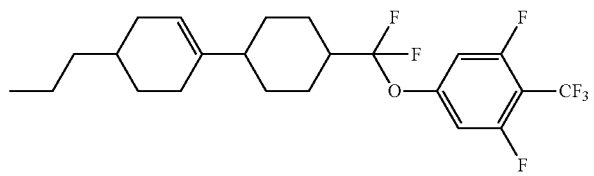 [SMILES: CCCC1CC=C(C2CCC(C(F)(F)Oc3cc(F)c(C(F)(F)F)c(F)c3)CC2)CC1] |
| 21 | 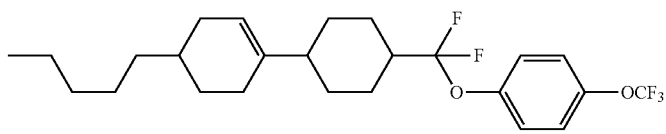 [SMILES: CCCCCC1CC=C(C2CCC(C(F)(F)Oc3ccc(OC(F)(F)F)cc3)CC2)CC1] |
| 22 | 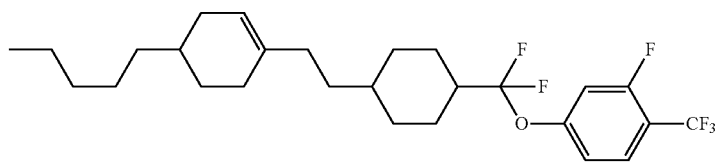 [SMILES: CCCCCC1CC=C(CCC2CCC(C(F)(F)Oc3ccc(C(F)(F)F)c(F)c3)CC2)CC1] |
| 23 | 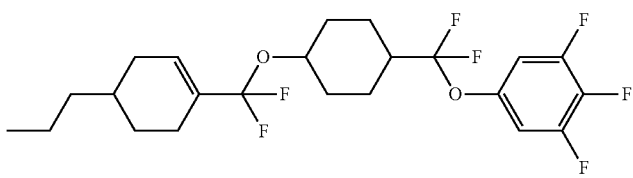 [SMILES: CCCC1CC=C(C(F)(F)OC2CCC(C(F)(F)Oc3cc(F)c(F)c(F)c3)CC2)CC1] |
| 24 | 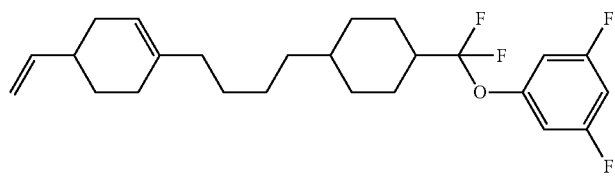 [SMILES: C=CC1CC=C(CCCCC2CCC(C(F)(F)Oc3cc(F)cc(F)c3)CC2)CC1] |
| 25 | 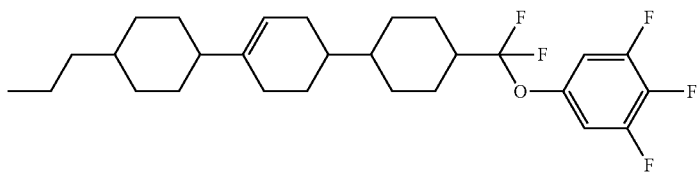 |
| 26 | 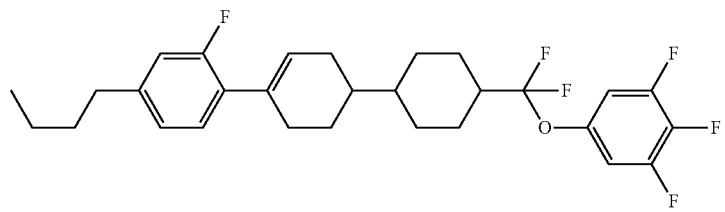 [SMILES: CCCCc1ccc(C2=CCC(C3CCC(C(F)(F)Oc4cc(F)c(F)c(F)c4)CC3)CC2)c(F)c1] |
| 27 | 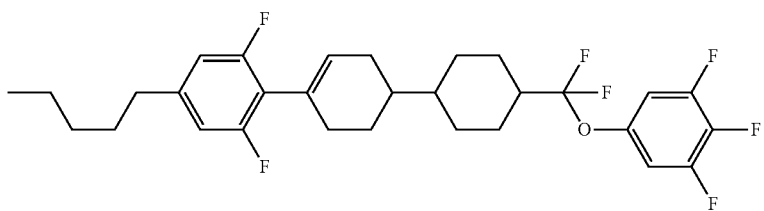 [SMILES: CCCCCc1cc(F)c(C2=CCC(C3CCC(C(F)(F)Oc4cc(F)c(F)c(F)c4)CC3)CC2)c(F)c1] |

| No. |
|---|
| 28 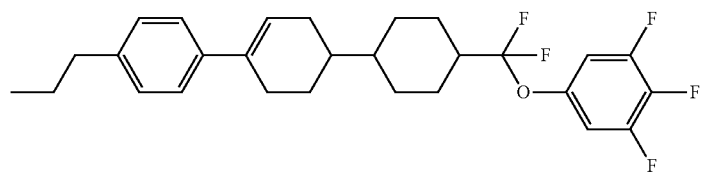 |
| 29 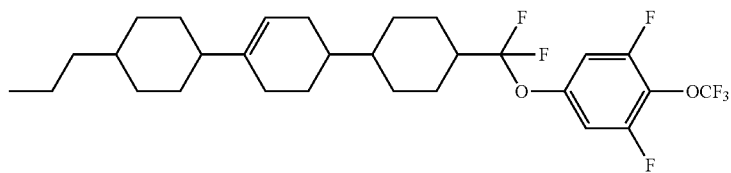 [SMILES: CCCC1CCC(C2=CCC(C3CCC(C(F)(F)Oc4cc(F)c(OC(F)(F)F)c(F)c4)CC3)CC2)CC1] |
| 30 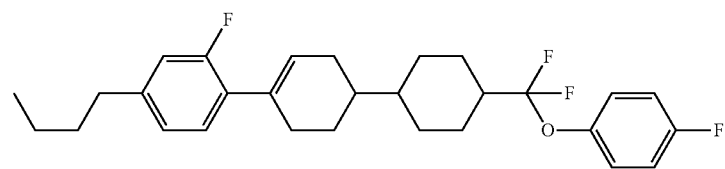 [SMILES: CCCCc1ccc(C2=CCC(C3CCC(C(F)(F)Oc4ccc(F)cc4)CC3)CC2)c(F)c1] |
| 31 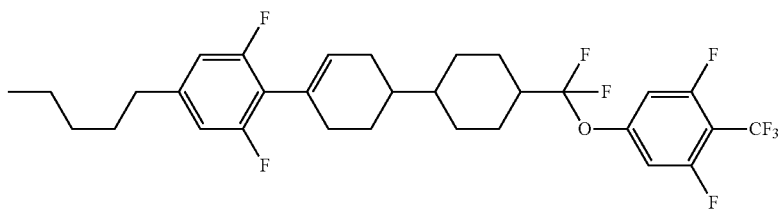 |
| 32 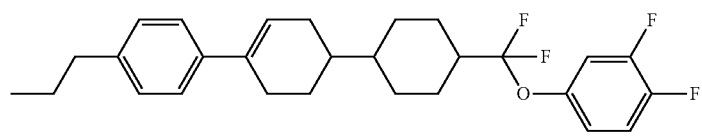 [SMILES: CCCc1ccc(C2=CCC(C3CCC(C(F)(F)Oc4ccc(F)c(F)c4)CC3)CC2)cc1] |
| 33 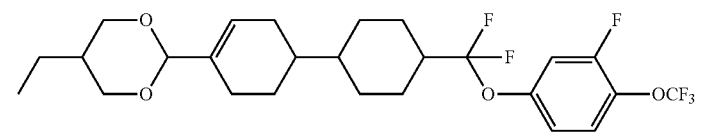 [SMILES: CCC1COC(C2=CCC(C3CCC(C(F)(F)Oc4ccc(OC(F)(F)F)c(F)c4)CC3)CC2)OC1] |
| 34 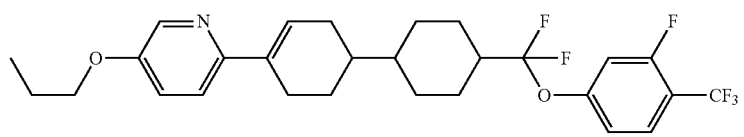 [SMILES: CCCOc1ccc(C2=CCC(C3CCC(C(F)(F)Oc4ccc(C(F)(F)F)c(F)c4)CC3)CC2)nc1] |
| 35 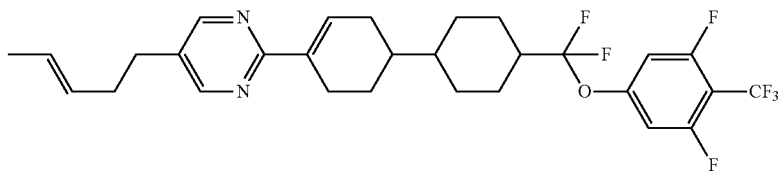 |
| 36 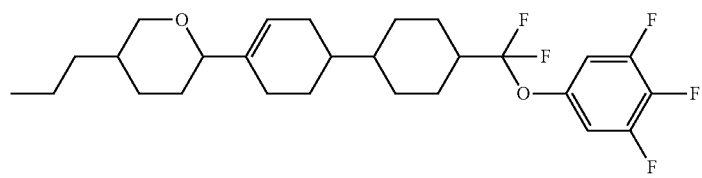 [SMILES: CCCC1CCC(C2=CCC(C3CCC(C(F)(F)Oc4cc(F)c(F)c(F)c4)CC3)CC2)OC1] |

| No. | |
|---|---|
| 37 | 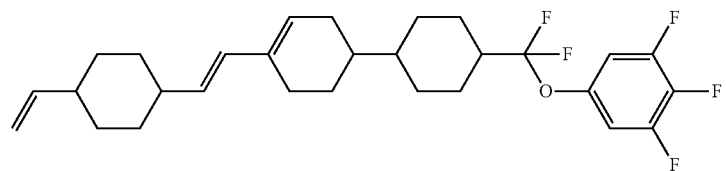 |
| 38 | 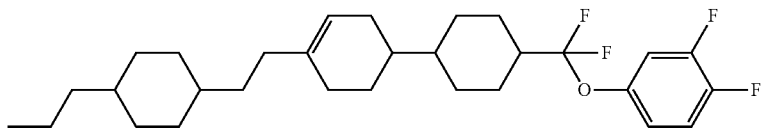 [SMILES: CCCC1CCC(CCC2=CCC(C3CCC(C(F)(F)Oc4ccc(F)c(F)c4)CC3)CC2)CC1] |
| 39 | 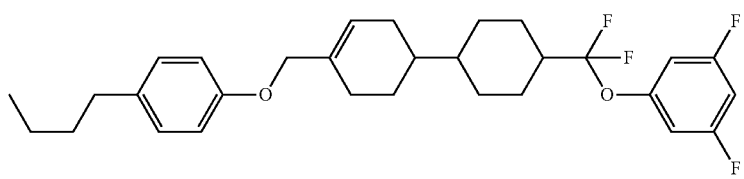 [SMILES: CCCCc1ccc(OCC2=CCC(C3CCC(C(F)(F)Oc4cc(F)cc(F)c4)CC3)CC2)cc1] |
| 40 | 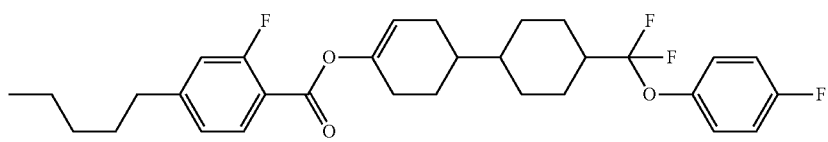 [SMILES: CCCCCc1ccc(C(=O)OC2=CCC(C3CCC(C(F)(F)Oc4ccc(F)cc4)CC3)CC2)c(F)c1] |
| 41 | 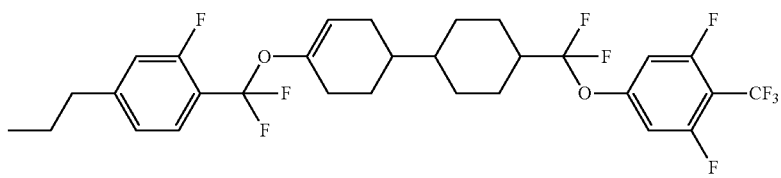 [SMILES: CCCc1ccc(C(F)(F)OC2=CCC(C3CCC(C(F)(F)Oc4cc(F)c(C(F)(F)F)c(F)c4)CC3)CC2)c(F)c1] |
| 42 | 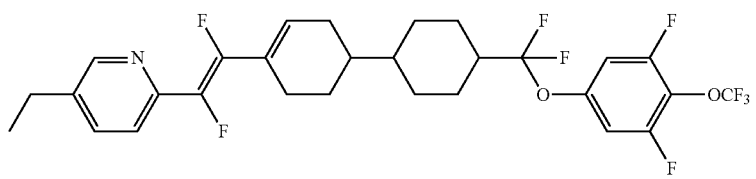 [SMILES: CCc1ccc(/C(F)=C(\F)C2=CCC(C3CCC(C(F)(F)Oc4cc(F)c(OC(F)(F)F)c(F)c4)CC3)CC2)nc1] |
| 43 | 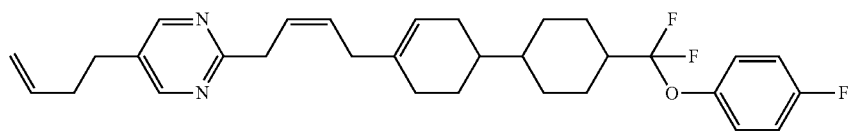 [SMILES: C=CCCc1cnc(C/C=C\CC2=CCC(C3CCC(C(F)(F)Oc4ccc(F)cc4)CC3)CC2)nc1] |
| 44 | 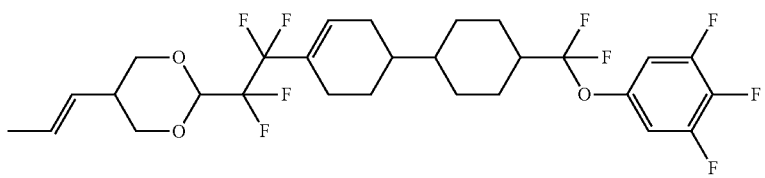 [SMILES: C/C=C/C1COC(C(F)(F)C(F)(F)C2=CCC(C3CCC(C(F)(F)Oc4cc(F)c(F)c(F)c4)CC3)CC2)OC1] |
| 45 | 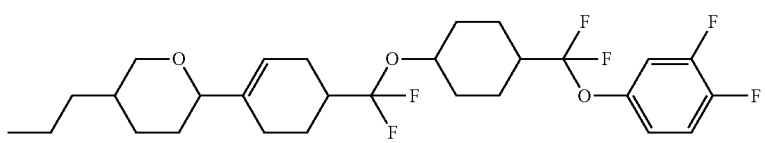 [SMILES: CCCC1CCC(C2=CCC(C(F)(F)OC3CCC(C(F)(F)Oc4ccc(F)c(F)c4)CC3)CC2)OC1] |

-continued
| No. | |
|---|---|
| 46 | 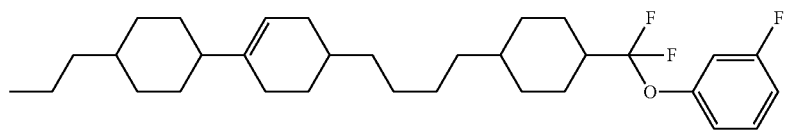 |
| 47 | 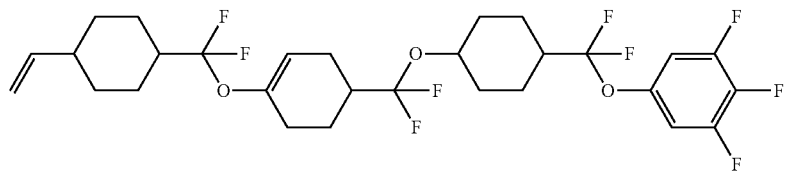 [SMILES: C=CC1CCC(C(F)(F)OC2=CCC(C(F)(F)OC3CCC(C(F)(F)Oc4cc(F)c(F)c(F)c4)CC3)CC2)CC1] |
| 48 | 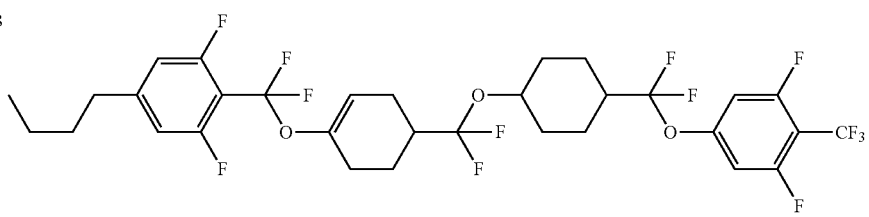 |
| 49 | 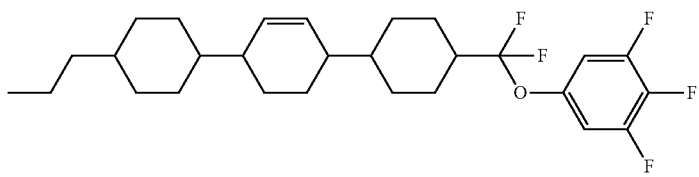 |
| 50 | 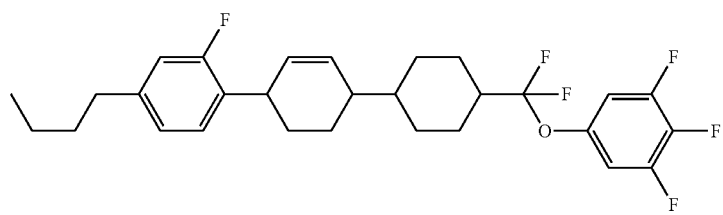 |
| 51 | 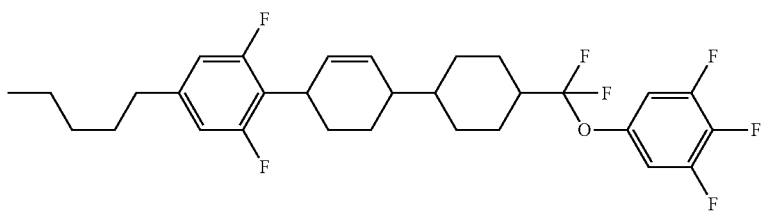 [SMILES: CCCCCc1cc(F)c(C2C=CC(C3CCC(C(F)(F)Oc4cc(F)c(F)c(F)c4)CC3)CC2)c(F)c1] |
| 52 | 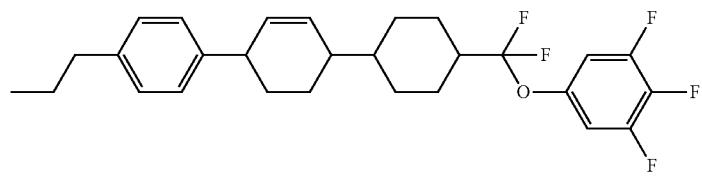 |
| 53 | 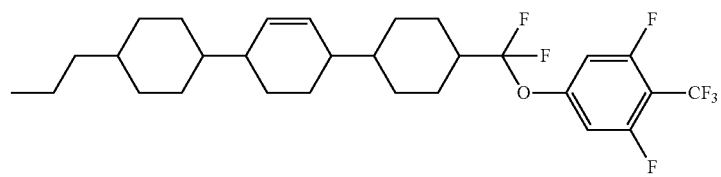 |

-continued
| No. | |
|---|---|
| 54 | 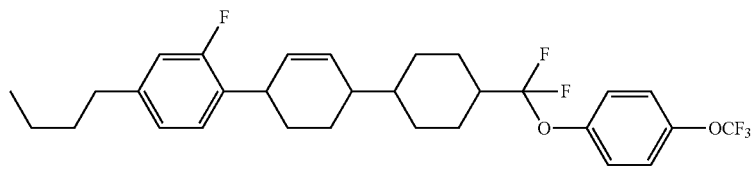 [SMILES: CCCCc1ccc(C2C=CC(C3CCC(C(F)(F)Oc4ccc(OC(F)(F)F)cc4)CC3)CC2)c(F)c1] |
| 55 | 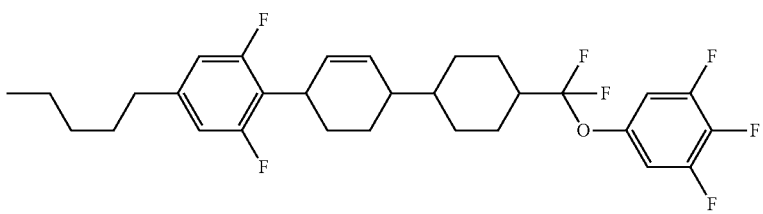 [SMILES: CCCCCc1cc(F)c(C2C=CC(C3CCC(C(F)(F)Oc4cc(F)c(F)c(F)c4)CC3)CC2)c(F)c1] |
| 56 | 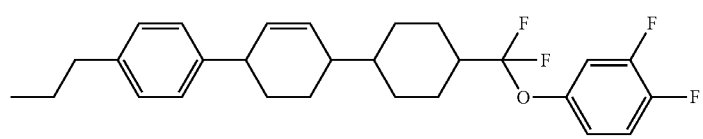 [SMILES: CCCc1ccc(C2C=CC(C3CCC(C(F)(F)Oc4ccc(F)c(F)c4)CC3)CC2)cc1] |
| 57 | 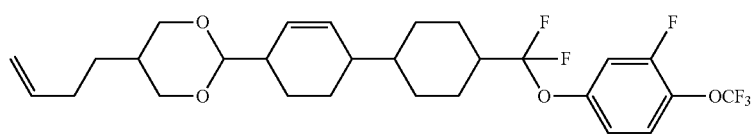 [SMILES: C=CCCC1COC(C2C=CC(C3CCC(C(F)(F)Oc4ccc(OC(F)(F)F)c(F)c4)CC3)CC2)OC1] |
| 58 | 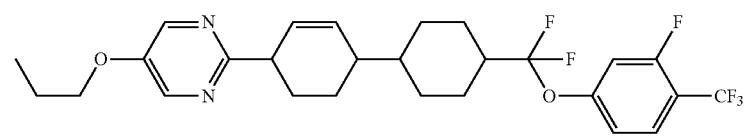 [SMILES: CCCOc1cnc(C2C=CC(C3CCC(C(F)(F)Oc4ccc(C(F)(F)F)c(F)c4)CC3)CC2)nc1] |
| 59 | 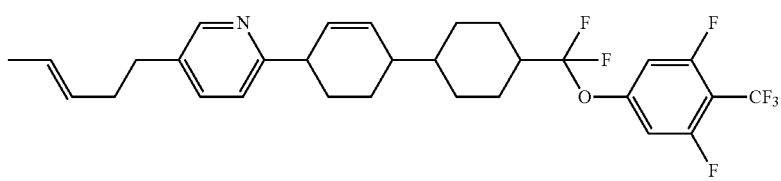 [SMILES: C/C=C/CCc1ccc(C2C=CC(C3CCC(C(F)(F)Oc4cc(F)c(C(F)(F)F)c(F)c4)CC3)CC2)nc1] |
| 60 | 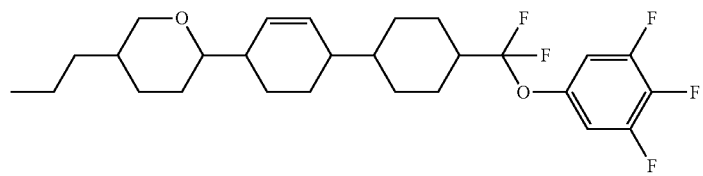 [SMILES: CCCC1CCC(C2C=CC(C3CCC(C(F)(F)Oc4cc(F)c(F)c(F)c4)CC3)CC2)OC1] |
| 61 | 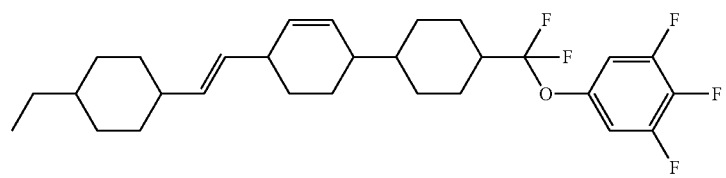 |
| 62 | 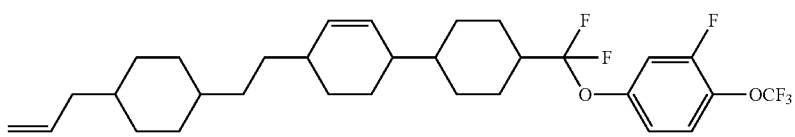 [SMILES: C=CCC1CCC(CCC2C=CC(C3CCC(C(F)(F)Oc4ccc(OC(F)(F)F)c(F)c4)CC3)CC2)CC1] |

-continued
| No. | |
|---|---|
| 63 | 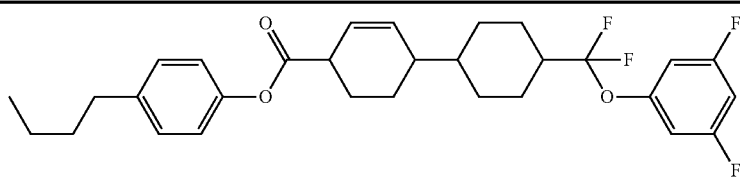 |
| 64 | 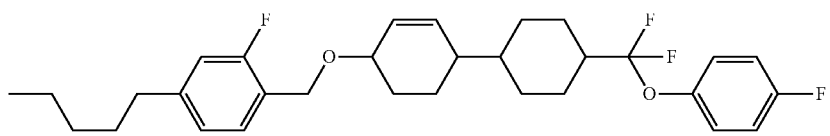 |
| 65 | 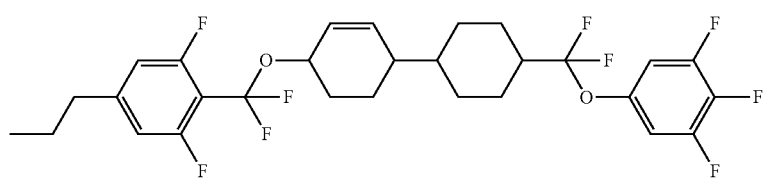 [SMILES: CCCc1cc(F)c(C(F)(F)OC2C=CC(C3CCC(C(F)(F)Oc4cc(F)c(F)c(F)c4)CC3)CC2)c(F)c1] |
| 66 | 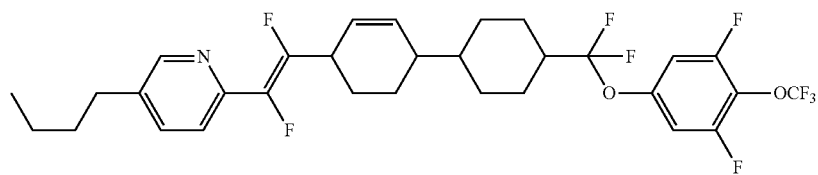 [SMILES: CCCCc1ccc(/C(F)=C(\F)C2C=CC(C3CCC(C(F)(F)Oc4cc(F)c(OC(F)(F)F)c(F)c4)CC3)CC2)nc1] |
| 67 | 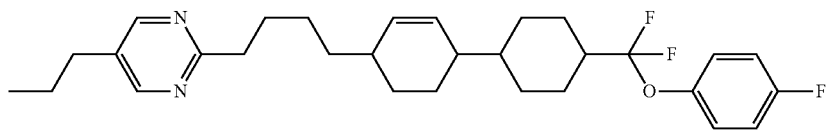 [SMILES: CCCc1cnc(CCCCC2C=CC(C3CCC(C(F)(F)Oc4ccc(F)cc4)CC3)CC2)nc1] |
| 68 | 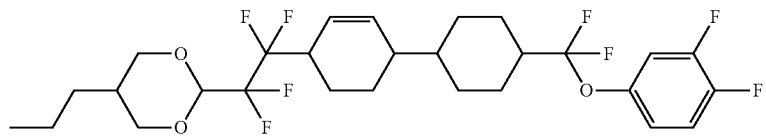 [SMILES: CCCC1COC(C(F)(F)C(F)(F)C2C=CC(C3CCC(C(F)(F)Oc4ccc(F)c(F)c4)CC3)CC2)OC1] |
| 69 | 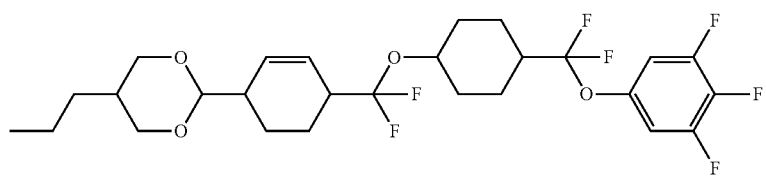 [SMILES: CCCC1COC(C2C=CC(C(F)(F)OC3CCC(C(F)(F)Oc4cc(F)c(F)c(F)c4)CC3)CC2)OC1] |
| 70 | 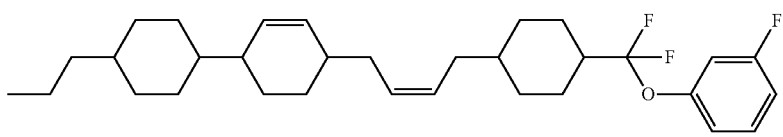 |
| 71 | 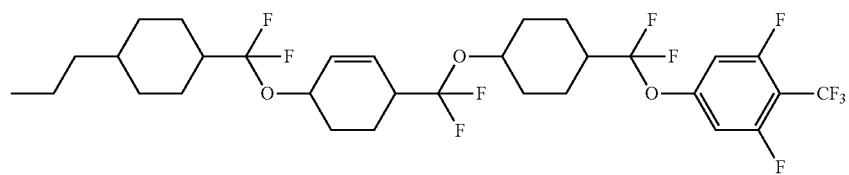 [SMILES: CCCC1CCC(C(F)(F)OC2C=CC(C(F)(F)OC3CCC(C(F)(F)Oc4cc(F)c(C(F)(F)F)c(F)c4)CC3)CC2)CC1] |

-continued
| No. |
|---|
| 72 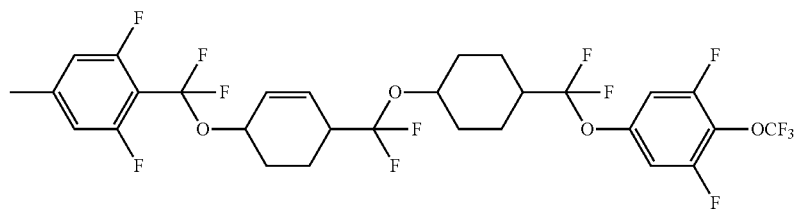 [SMILES: Cc1cc(F)c(C(F)(F)OC2C=CC(C(F)(F)OC3CCC(C(F)(F)Oc4cc(F)c(OC(F)(F)F)c(F)c4)CC3)CC2)c(F)c1] |
| 73 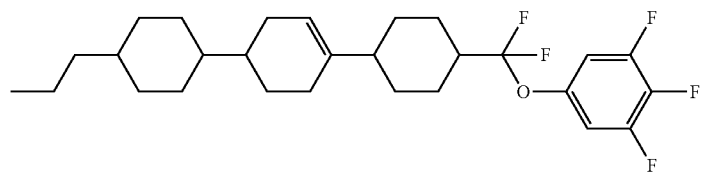 [SMILES: CCCC1CCC(C2CC=C(C3CCC(C(F)(F)Oc4cc(F)c(F)c(F)c4)CC3)CC2)CC1] |
| 74 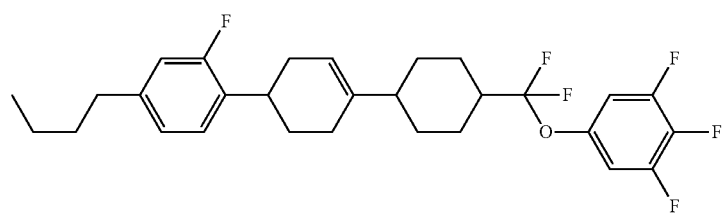 [SMILES: CCCCc1ccc(C2CC=C(C3CCC(C(F)(F)Oc4cc(F)c(F)c(F)c4)CC3)CC2)c(F)c1] |
| 75 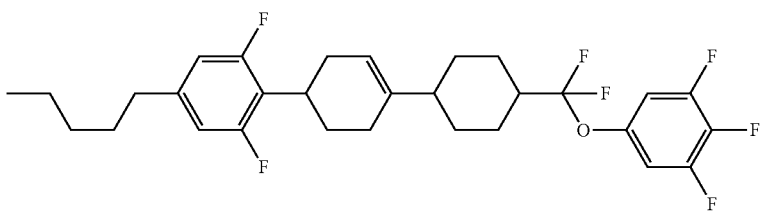 [SMILES: CCCCCc1cc(F)c(C2CC=C(C3CCC(C(F)(F)Oc4cc(F)c(F)c(F)c4)CC3)CC2)c(F)c1] |
| 76 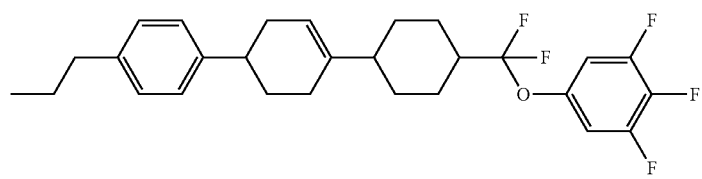 [SMILES: CCCc1ccc(C2CC=C(C3CCC(C(F)(F)Oc4cc(F)c(F)c(F)c4)CC3)CC2)cc1] |
| 77 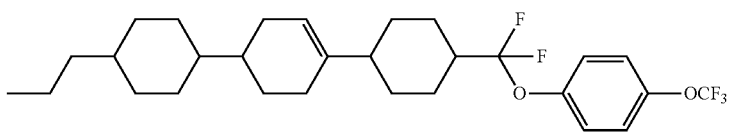 [SMILES: CCCC1CCC(C2CC=C(C3CCC(C(F)(F)Oc4ccc(OC(F)(F)F)cc4)CC3)CC2)CC1] |
| 78 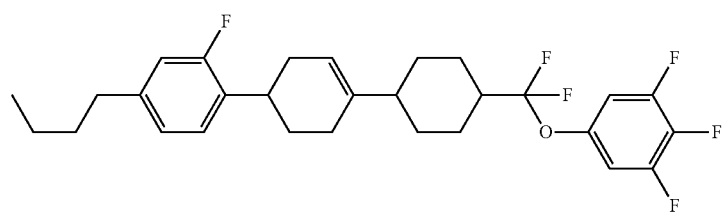 |
| 79 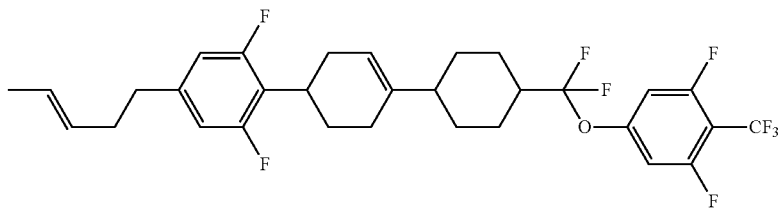 [SMILES: C/C=C/CCc1cc(F)c(C2CC=C(C3CCC(C(F)(F)Oc4cc(F)c(C(F)(F)F)c(F)c4)CC3)CC2)c(F)c1] |

-continued
| No. | |
|---|---|
| 80 | 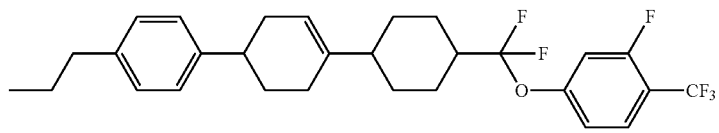 [SMILES: CCCc1ccc(C2CC=C(C3CCC(C(F)(F)Oc4ccc(C(F)(F)F)c(F)c4)CC3)CC2)cc1] |
| 81 | 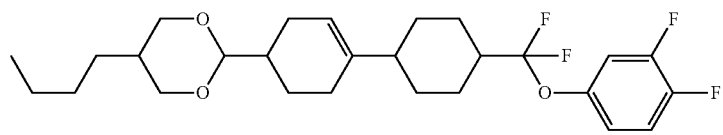 |
| 82 | 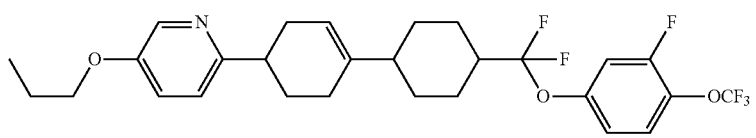 |
| 83 | 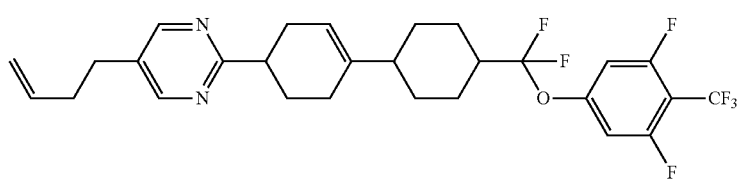 [SMILES: C=CCCc1cnc(C2CC=C(C3CCC(C(F)(F)Oc4cc(F)c(C(F)(F)F)c(F)c4)CC3)CC2)nc1] |
| 84 | 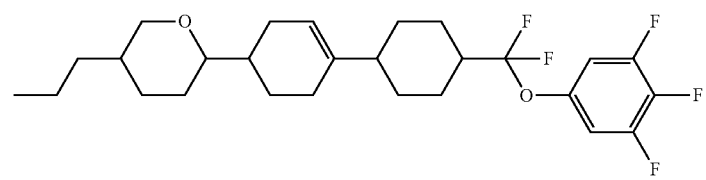 |
| 85 | 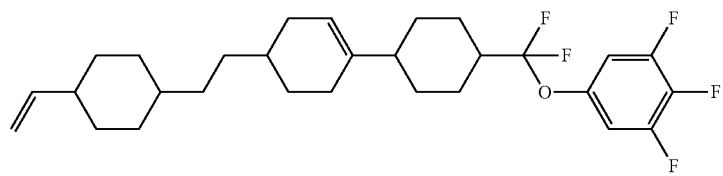 [SMILES: C=CC1CCC(CCC2CC=C(C3CCC(C(F)(F)Oc4cc(F)c(F)c(F)c4)CC3)CC2)CC1] |
| 86 | 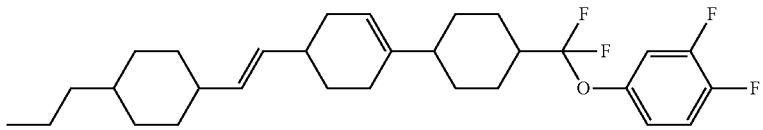 [SMILES: CCCC1CCC(/C=C/C2CC=C(C3CCC(C(F)(F)Oc4ccc(F)c(F)c4)CC3)CC2)CC1] |
| 87 | 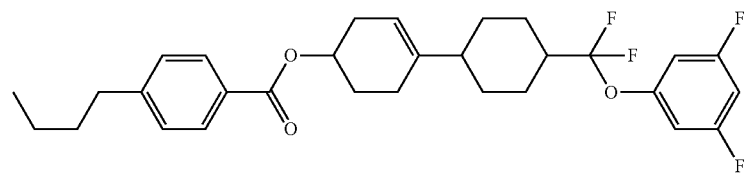 [SMILES: CCCCc1ccc(C(=O)OC2CC=C(C3CCC(C(F)(F)Oc4cc(F)cc(F)c4)CC3)CC2)cc1] |
| 88 | 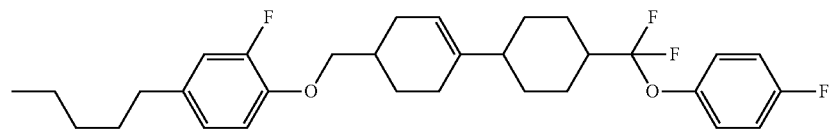 [SMILES: CCCCCc1ccc(OCC2CC=C(C3CCC(C(F)(F)Oc4ccc(F)cc4)CC3)CC2)c(F)c1] |
| 89 | 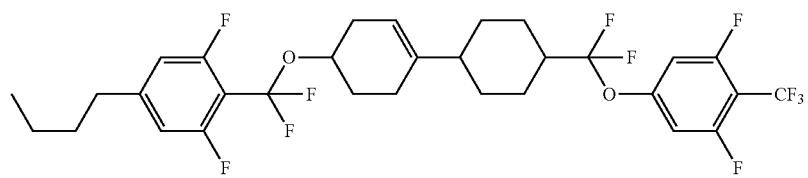 [SMILES: CCCCc1cc(F)c(C(F)(F)OC2CC=C(C3CCC(C(F)(F)Oc4cc(F)c(C(F)(F)F)c(F)c4)CC3)CC2)c(F)c1] |

| No. |
| --- |
| 90 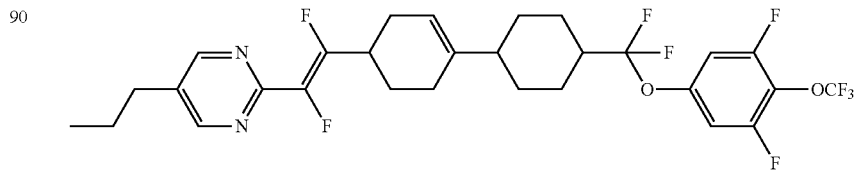 |
| 91 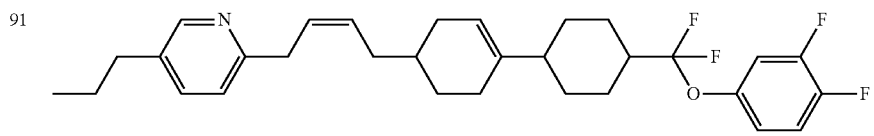 |
| 92 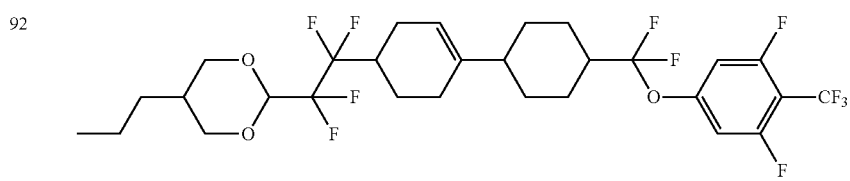 |
| 93 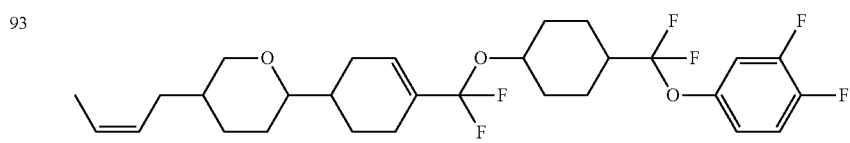 |
| 94 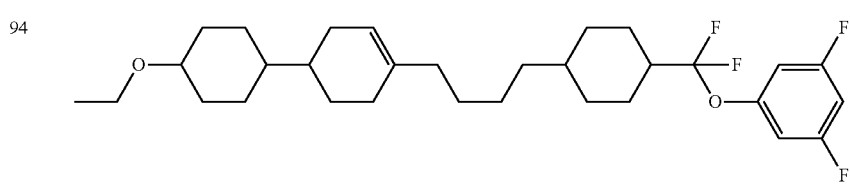 |
| 95 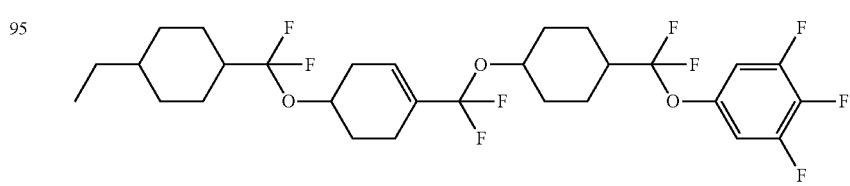 |
| 96 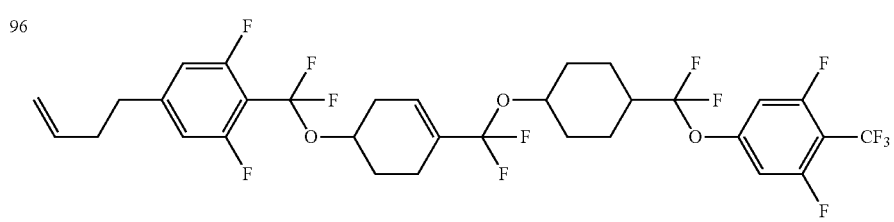 |
| 97 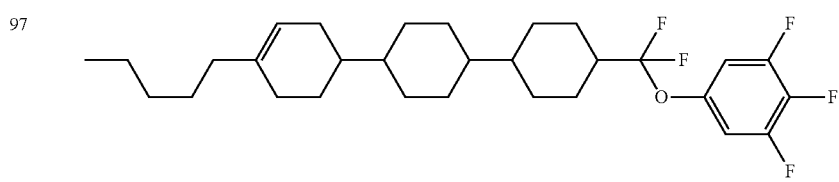 |
| 98 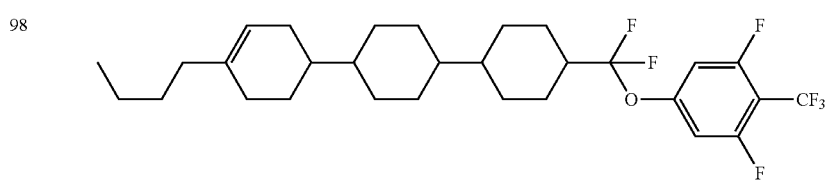 |

| No. | |
|---|---|
| 99 | 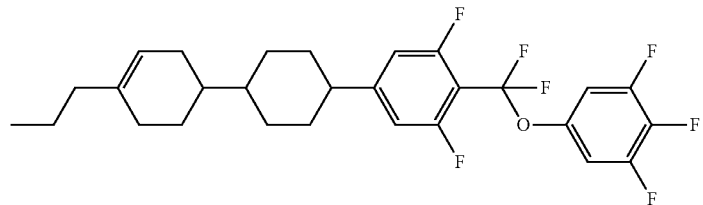 C 71.7 C 76.1 N 111.5 I<br>NI = 79.0° C., Δε = 25.4, Δn = 0.097, η = 60.5 mPa·s |
| 100 | 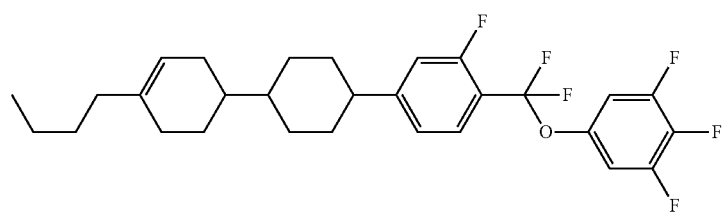 [SMILES: CCCCC1=CCC(C2CCC(c3ccc(C(F)(F)Oc4cc(F)c(F)c(F)c4)c(F)c3)CC2)CC1] |
| 101 | 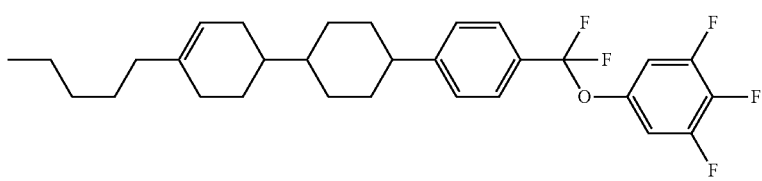 [SMILES: CCCCCC1=CCC(C2CCC(c3ccc(C(F)(F)Oc4cc(F)c(F)c(F)c4)cc3)CC2)CC1] |
| 102 | 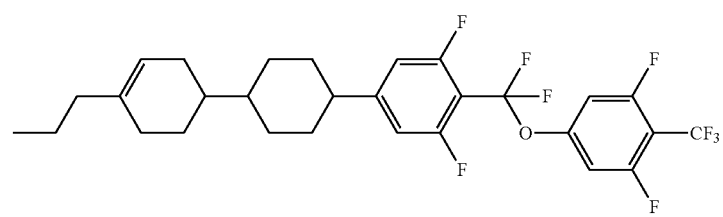 [SMILES: CCCC1=CCC(C2CCC(c3cc(F)c(C(F)(F)Oc4cc(F)c(C(F)(F)F)c(F)c4)c(F)c3)CC2)CC1] |
| 103 | 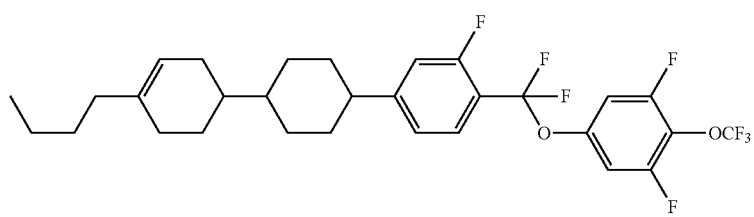 [SMILES: CCCCC1=CCC(C2CCC(c3ccc(C(F)(F)Oc4cc(F)c(OC(F)(F)F)c(F)c4)c(F)c3)CC2)CC1] |
| 104 | 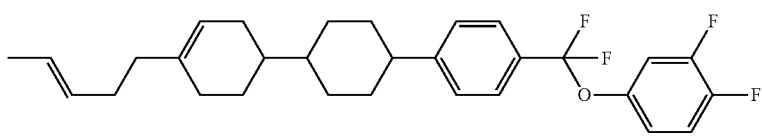 |
| 105 | 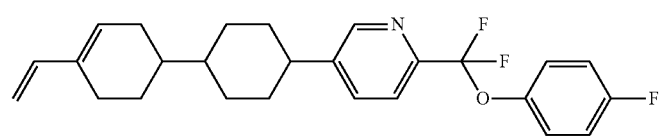 [SMILES: C=CC1=CCC(C2CCC(c3ccc(C(F)(F)Oc4ccc(F)cc4)nc3)CC2)CC1] |
| 106 | 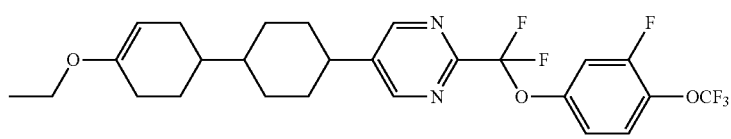 |

-continued
| No. |
|---|
| 107 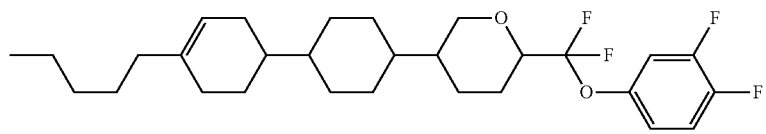 [SMILES: CCCCCC1=CCC(C2CCC(C3CCC(C(F)(F)Oc4ccc(F)c(F)c4)OC3)CC2)CC1] |
| 108 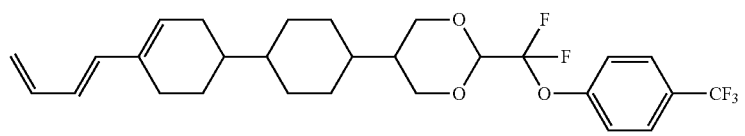 [SMILES: C=C/C=C/C1=CCC(C2CCC(C3COC(C(F)(F)Oc4ccc(C(F)(F)F)cc4)OC3)CC2)CC1] |
| 109 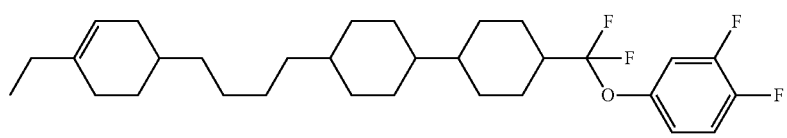 [SMILES: CCC1=CCC(CCCCC2CCC(C3CCC(C(F)(F)Oc4ccc(F)c(F)c4)CC3)CC2)CC1] |
| 110 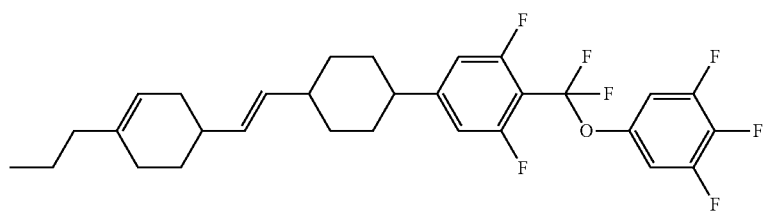 [SMILES: CCCC1=CCC(/C=C/C2CCC(c3cc(F)c(C(F)(F)Oc4cc(F)c(F)c(F)c4)c(F)c3)CC2)CC1] |
| 111 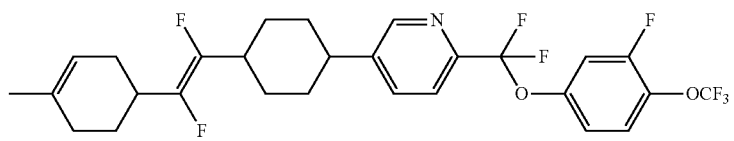 [SMILES: CC1=CCC(/C(F)=C(\F)C2CCC(c3ccc(C(F)(F)Oc4ccc(OC(F)(F)F)c(F)c4)nc3)CC2)CC1] |
| 112 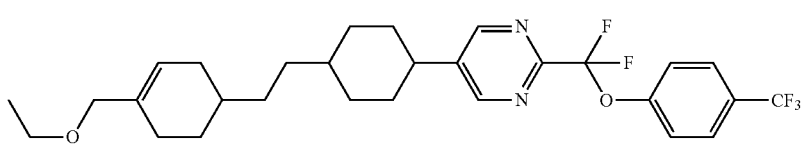 [SMILES: CCOCC1=CCC(CCC2CCC(c3cnc(C(F)(F)Oc4ccc(C(F)(F)F)cc4)nc3)CC2)CC1] |
| 113 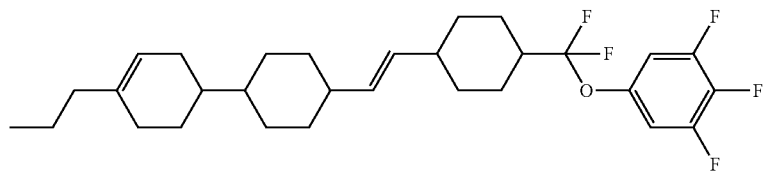 [SMILES: CCCC1=CCC(C2CCC(/C=C/C3CCC(C(F)(F)Oc4cc(F)c(F)c(F)c4)CC3)CC2)CC1] |
| 114 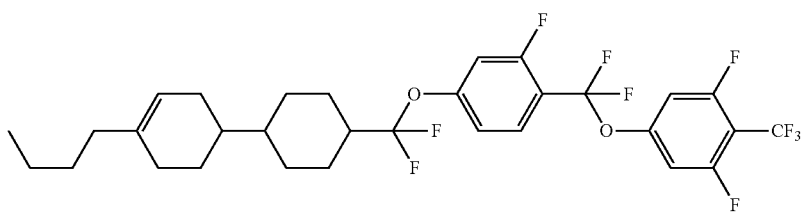 [SMILES: CCCCC1=CCC(C2CCC(C(F)(F)Oc3ccc(C(F)(F)Oc4cc(F)c(C(F)(F)F)c(F)c4)c(F)c3)CC2)CC1] |
| 115 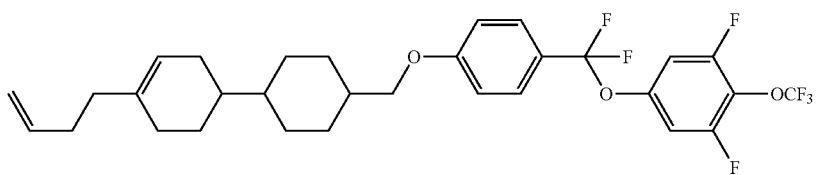 [SMILES: C=CCCC1=CCC(C2CCC(COc3ccc(C(F)(F)Oc4cc(F)c(OC(F)(F)F)c(F)c4)cc3)CC2)CC1] |

-continued
| No. |
|---|
| 116 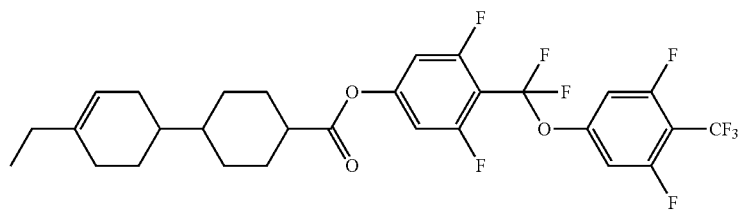 [SMILES: CCC1=CCC(C2CCC(C(=O)Oc3cc(F)c(C(F)(F)Oc4cc(F)c(C(F)(F)F)c(F)c4)c(F)c3)CC2)CC1] |
| 117 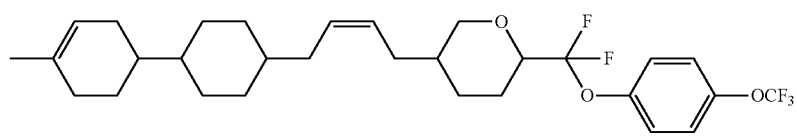 [SMILES: CC1=CCC(C2CCC(C/C=C\CC3CCC(C(F)(F)Oc4ccc(OC(F)(F)F)cc4)OC3)CC2)CC1] |
| 118 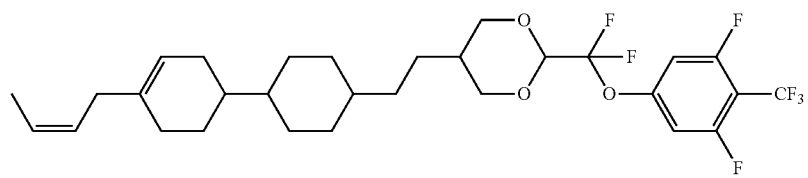 |
| 119 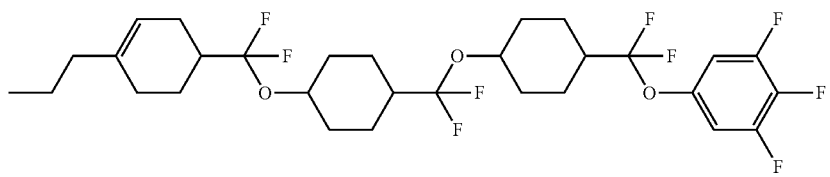 |
| 120 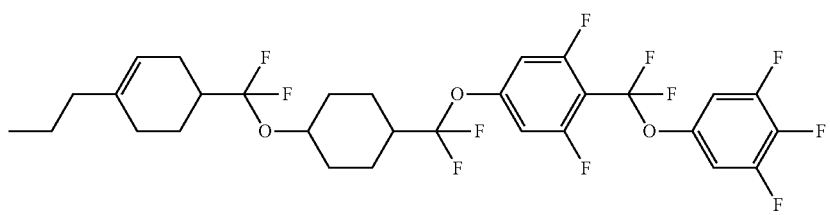 [SMILES: CCCC1=CCC(C(F)(F)OC2CCC(C(F)(F)Oc3cc(F)c(C(F)(F)Oc4cc(F)c(F)c(F)c4)c(F)c3)CC2)CC1] |
| 121 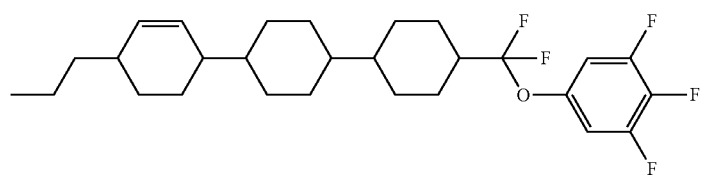 |
| 122 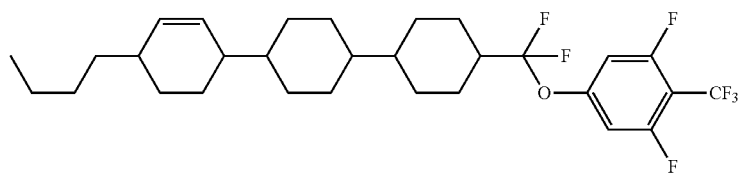 [SMILES: CCCCC1C=CC(C2CCC(C3CCC(C(F)(F)Oc4cc(F)c(C(F)(F)F)c(F)c4)CC3)CC2)CC1] |
| 123 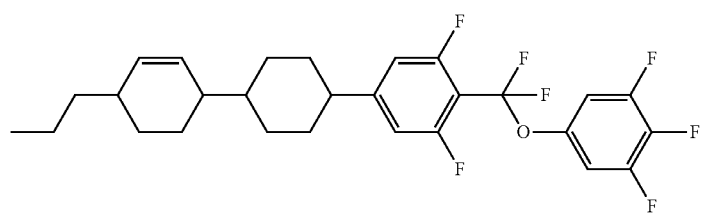 [SMILES: CCCC1C=CC(C2CCC(c3cc(F)c(C(F)(F)Oc4cc(F)c(F)c(F)c4)c(F)c3)CC2)CC1] |

| No. |
|---|
| 124 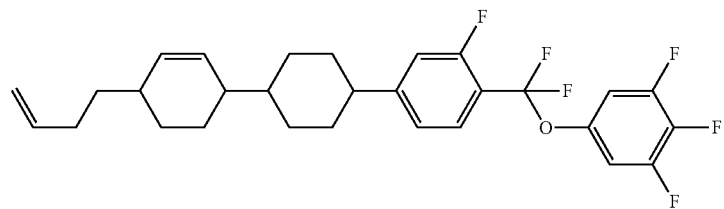 [SMILES: C=CCCC1C=CC(C2CCC(c3ccc(C(F)(F)Oc4cc(F)c(F)c(F)c4)c(F)c3)CC2)CC1] |
| 125 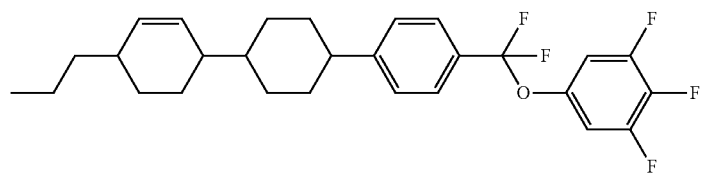 [SMILES: CCCC1C=CC(C2CCC(c3ccc(C(F)(F)Oc4cc(F)c(F)c(F)c4)cc3)CC2)CC1] |
| 126 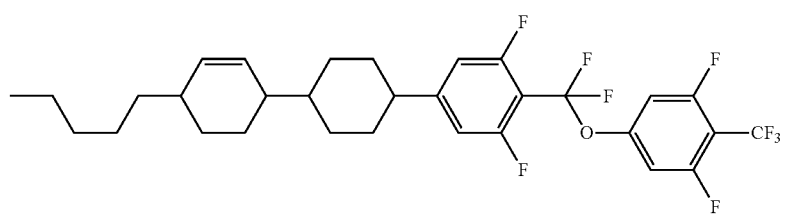 [SMILES: CCCCCC1C=CC(C2CCC(c3cc(F)c(C(F)(F)Oc4cc(F)c(C(F)(F)F)c(F)c4)c(F)c3)CC2)CC1] |
| 127 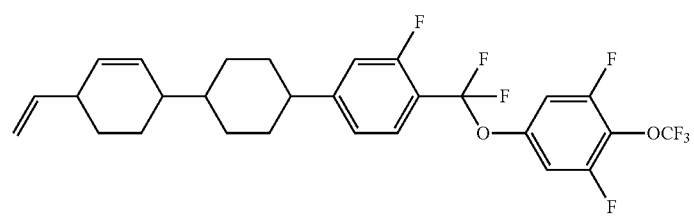 [SMILES: C=CC1C=CC(C2CCC(c3ccc(C(F)(F)Oc4cc(F)c(OC(F)(F)F)c(F)c4)c(F)c3)CC2)CC1] |
| 128 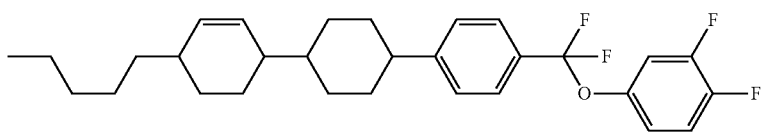 [SMILES: CCCCCC1C=CC(C2CCC(c3ccc(C(F)(F)Oc4ccc(F)c(F)c4)cc3)CC2)CC1] |
| 129 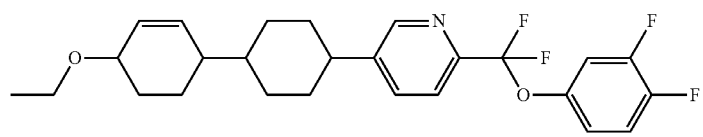 |
| 130 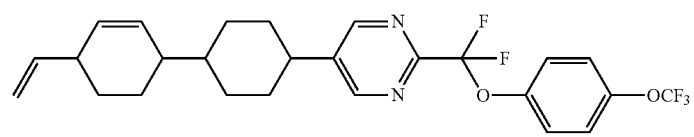 [SMILES: C=CC1C=CC(C2CCC(c3cnc(C(F)(F)Oc4ccc(OC(F)(F)F)cc4)nc3)CC2)CC1] |
| 131 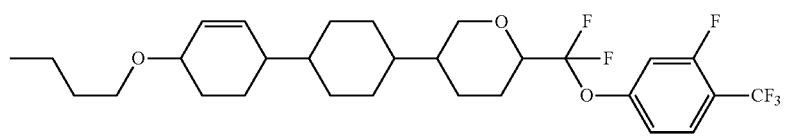 [SMILES: CCCCOC1C=CC(C2CCC(C3CCC(C(F)(F)Oc4ccc(C(F)(F)F)c(F)c4)OC3)CC2)CC1] |
| 132 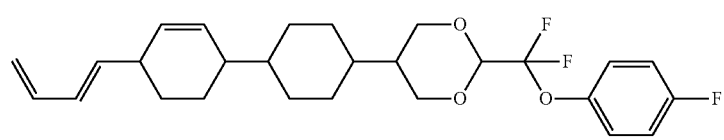 [SMILES: C=C/C=C/C1C=CC(C2CCC(C3COC(C(F)(F)Oc4ccc(F)cc4)OC3)CC2)CC1] |

-continued
| No. | |
|---|---|
| 133 | 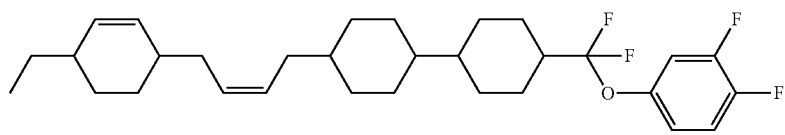 [SMILES: CCC1C=CC(C/C=C\CC2CCC(C3CCC(C(F)(F)Oc4ccc(F)c(F)c4)CC3)CC2)CC1] |
| 134 | 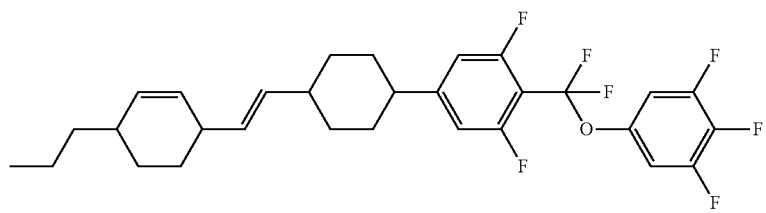 |
| 135 | 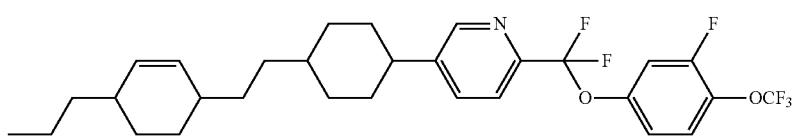 |
| 136 | 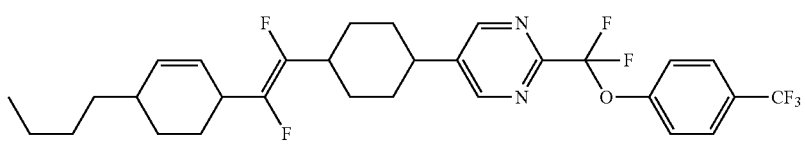 [SMILES: CCCCC1C=CC(/C(F)=C(\F)C2CCC(c3cnc(C(F)(F)Oc4ccc(C(F)(F)F)cc4)nc3)CC2)CC1] |
| 137 | 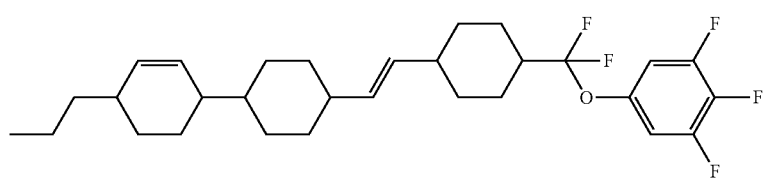 |
| 138 | 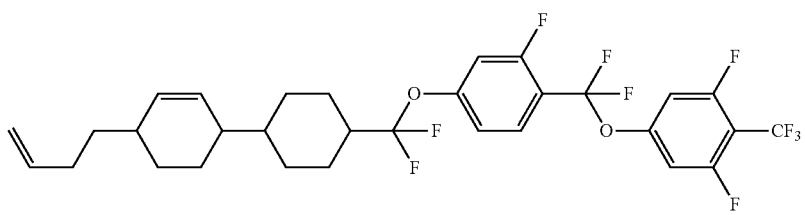 [SMILES: C=CCCC1C=CC(C2CCC(C(F)(F)Oc3ccc(C(F)(F)Oc4cc(F)c(C(F)(F)F)c(F)c4)c(F)c3)CC2)CC1] |
| 139 | 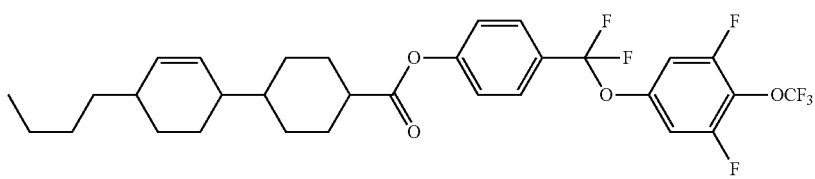 |
| 140 | 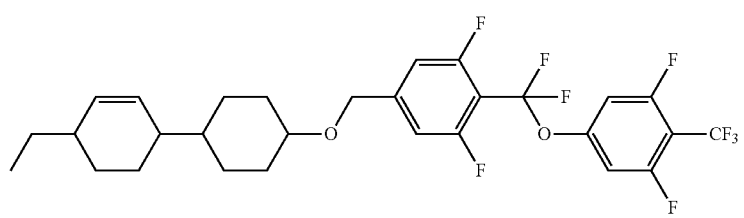 [SMILES: CCC1C=CC(C2CCC(OCc3cc(F)c(C(F)(F)Oc4cc(F)c(C(F)(F)F)c(F)c4)c(F)c3)CC2)CC1] |
| 141 | 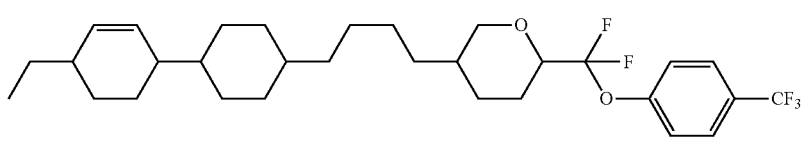 [SMILES: CCC1C=CC(C2CCC(CCCCC3CCC(C(F)(F)Oc4ccc(C(F)(F)F)cc4)OC3)CC2)CC1] |

-continued
| No. | |
|---|---|
| 142 | 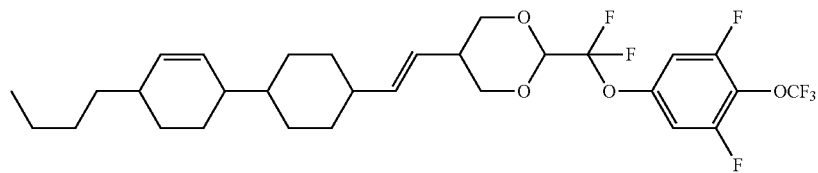 [SMILES: CCCCC1C=CC(C2CCC(/C=C/C3COC(C(F)(F)Oc4cc(F)c(OC(F)(F)F)c(F)c4)OC3)CC2)CC1] |
| 143 | 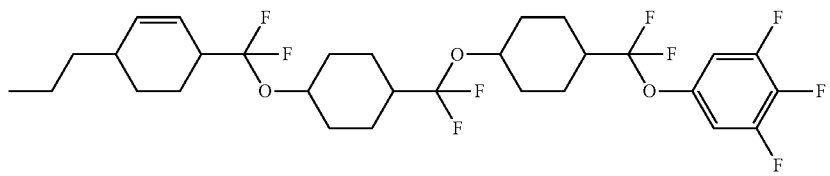 |
| 144 | 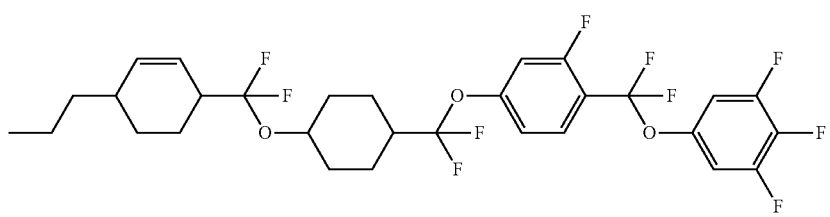 |
| 145 | 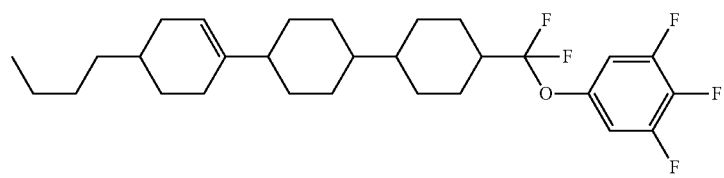 [SMILES: CCCCC1CC=C(C2CCC(C3CCC(C(F)(F)Oc4cc(F)c(F)c(F)c4)CC3)CC2)CC1] |
| 146 | 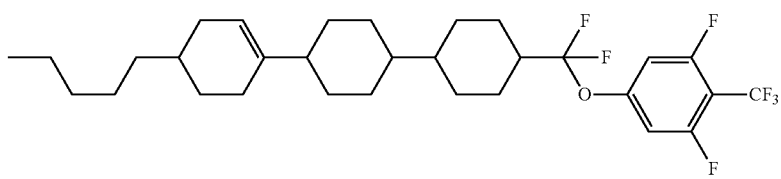 |
| 147 | 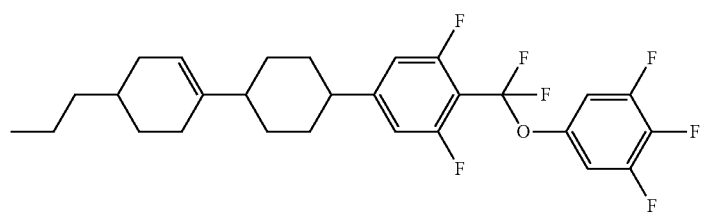 |
| | C 8.1 C 72.6 N 112.2 I<br>NI = 77.0° C., Δε = 24.2, Δn = 0.104, η = 60.5 mPa · s |
| 148 | 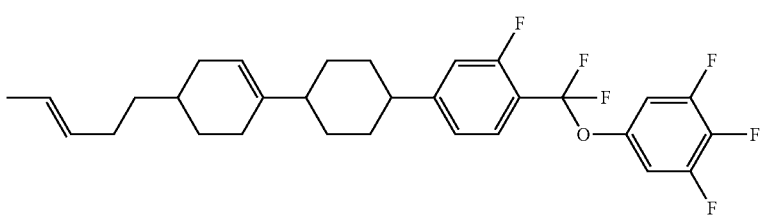 [SMILES: C/C=C/CCC1CC=C(C2CCC(c3ccc(C(F)(F)Oc4cc(F)c(F)c(F)c4)c(F)c3)CC2)CC1] |

| No. |
|---|
| 149 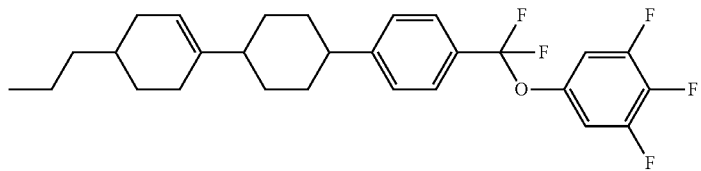 [SMILES: CCCC1CC=C(C2CCC(c3ccc(C(F)(F)Oc4cc(F)c(F)c(F)c4)cc3)CC2)CC1] |
| 150 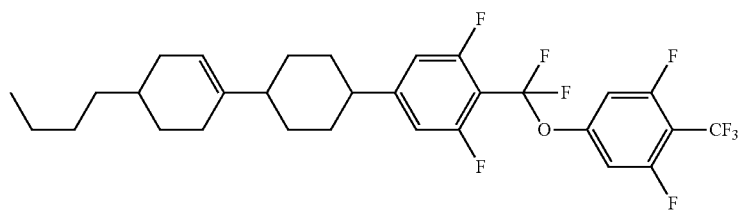 [SMILES: CCCCC1CC=C(C2CCC(c3cc(F)c(C(F)(F)Oc4cc(F)c(C(F)(F)F)c(F)c4)c(F)c3)CC2)CC1] |
| 151 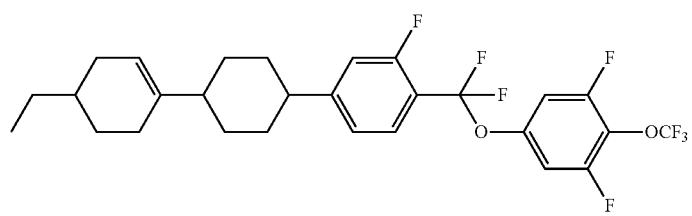 [SMILES: CCC1CC=C(C2CCC(c3ccc(C(F)(F)Oc4cc(F)c(OC(F)(F)F)c(F)c4)c(F)c3)CC2)CC1] |
| 152 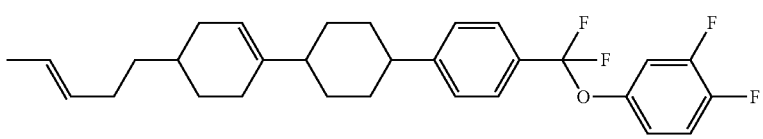 |
| 153 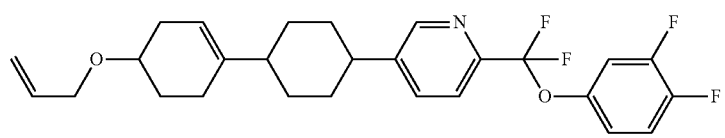 |
| 154 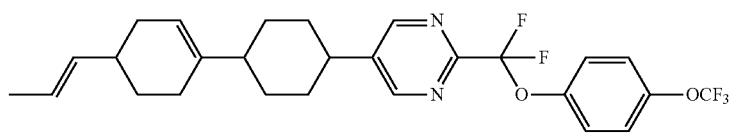 [SMILES: C/C=C/C1CC=C(C2CCC(c3cnc(C(F)(F)Oc4ccc(OC(F)(F)F)cc4)nc3)CC2)CC1] |
| 155 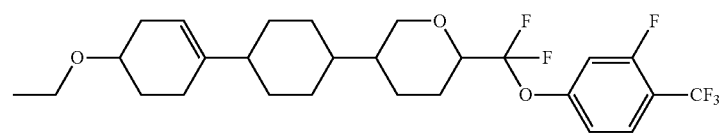 |
| 156 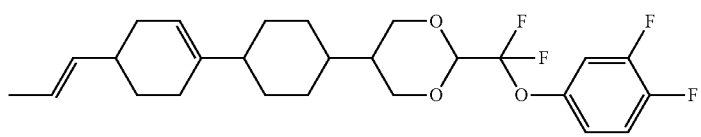 [SMILES: C/C=C/C1CC=C(C2CCC(C3COC(C(F)(F)Oc4ccc(F)c(F)c4)OC3)CC2)CC1] |
| 157 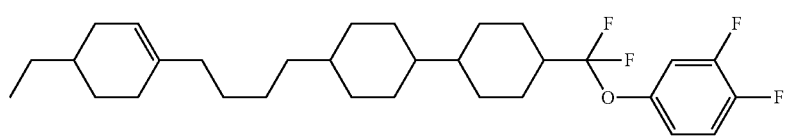 |

| No. |  |
|---|---|
| 158 | 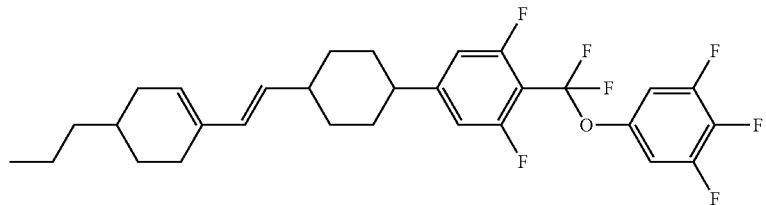 [SMILES: CCCC1CC=C(/C=C/C2CCC(c3cc(F)c(C(F)(F)Oc4cc(F)c(F)c(F)c4)c(F)c3)CC2)CC1] |
| 159 | 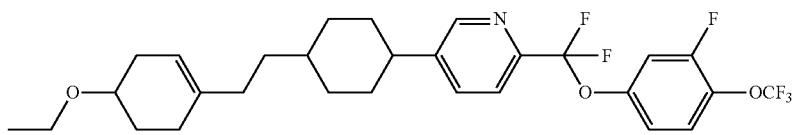 [SMILES: CCOC1CC=C(CCC2CCC(c3ccc(C(F)(F)Oc4ccc(OC(F)(F)F)c(F)c4)nc3)CC2)CC1] |
| 160 | 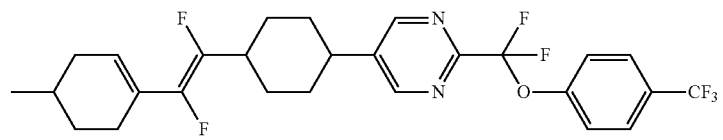 [SMILES: CC1CC=C(/C(F)=C(\F)C2CCC(c3cnc(C(F)(F)Oc4ccc(C(F)(F)F)cc4)nc3)CC2)CC1] |
| 161 | 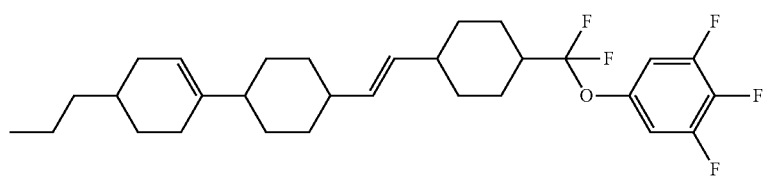 |
| 162 | 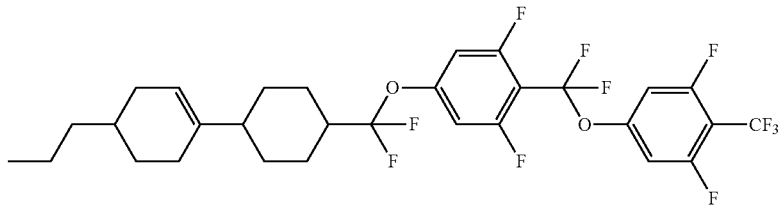 [SMILES: CCCC1CC=C(C2CCC(C(F)(F)Oc3cc(F)c(C(F)(F)Oc4cc(F)c(C(F)(F)F)c(F)c4)c(F)c3)CC2)CC1] |
| 163 | 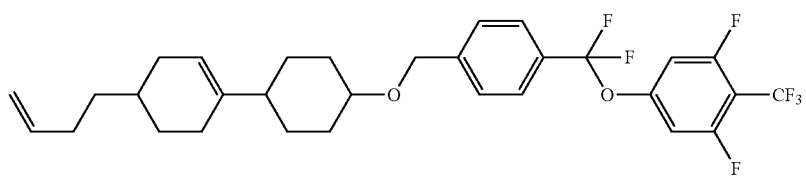 [SMILES: C=CCCC1CC=C(C2CCC(OCc3ccc(C(F)(F)Oc4cc(F)c(C(F)(F)F)c(F)c4)cc3)CC2)CC1] |
| 164 | 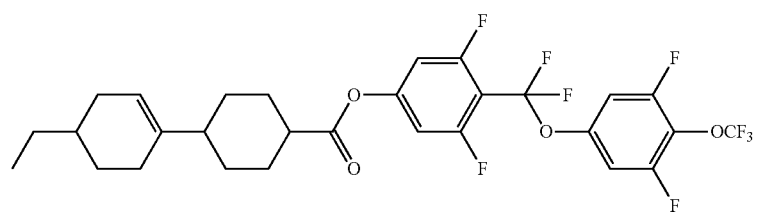 [SMILES: CCC1CC=C(C2CCC(C(=O)Oc3cc(F)c(C(F)(F)Oc4cc(F)c(OC(F)(F)F)c(F)c4)c(F)c3)CC2)CC1] |
| 165 | 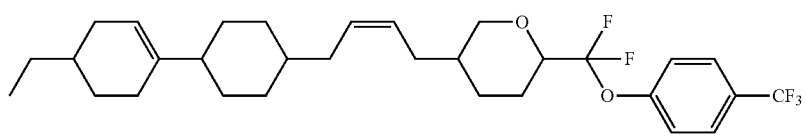 [SMILES: CCC1CC=C(C2CCC(C/C=C\CC3CCC(C(F)(F)Oc4ccc(C(F)(F)F)cc4)OC3)CC2)CC1] |

| No. |
|---|
| 166 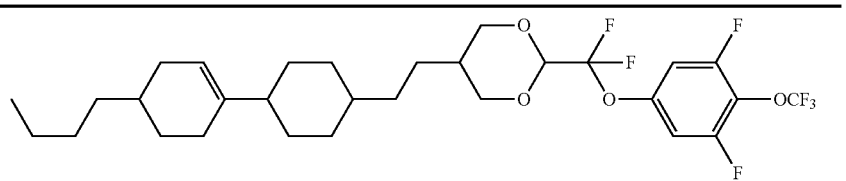 |
| 167 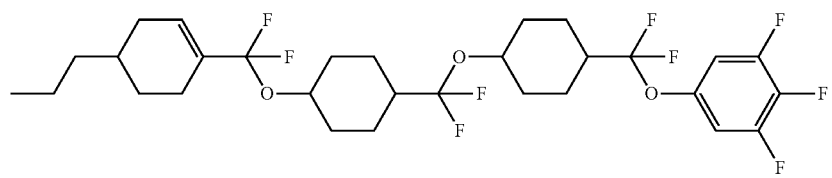 [SMILES: CCCC1CC=C(C(F)(F)OC2CCC(C(F)(F)OC3CCC(C(F)(F)Oc4cc(F)c(F)c(F)c4)CC3)CC2)CC1] |
| 168 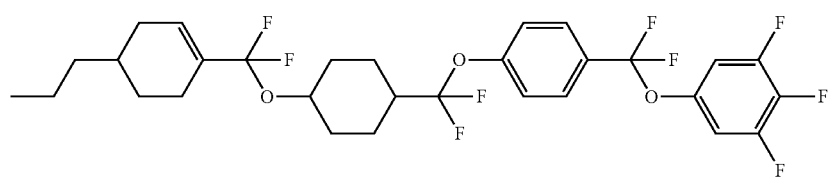 |
| 169 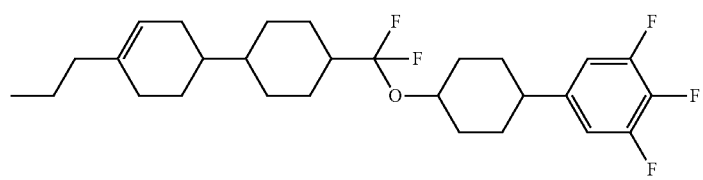 [SMILES: CCCC1=CCC(C2CCC(C(F)(F)OC3CCC(c4cc(F)c(F)c(F)c4)CC3)CC2)CC1] |
| 170 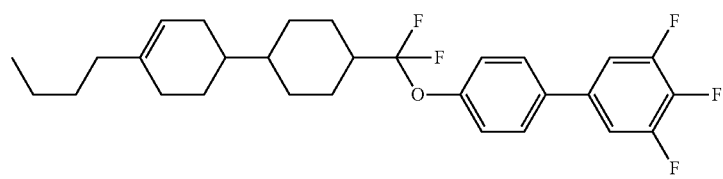 [SMILES: CCCCC1=CCC(C2CCC(C(F)(F)Oc3ccc(-c4cc(F)c(F)c(F)c4)cc3)CC2)CC1] |
| 171 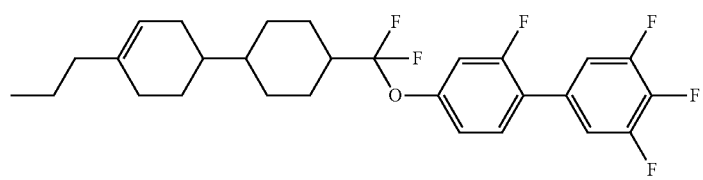 |
| 172 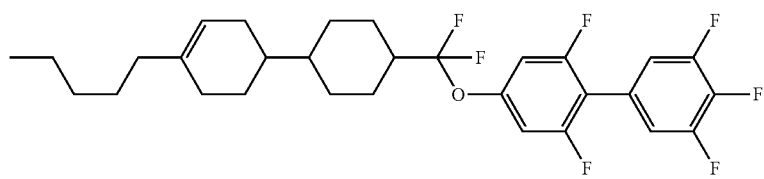 [SMILES: CCCCCC1=CCC(C2CCC(C(F)(F)Oc3cc(F)c(-c4cc(F)c(F)c(F)c4)c(F)c3)CC2)CC1] |
| 173 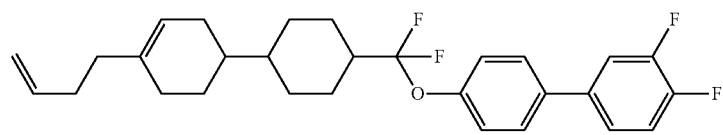 |
| 174 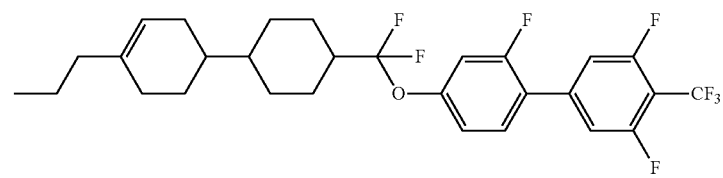 [SMILES: CCCC1=CCC(C2CCC(C(F)(F)Oc3ccc(-c4cc(F)c(C(F)(F)F)c(F)c4)c(F)c3)CC2)CC1] |

-continued
| No. | |
|---|---|
| 175 | 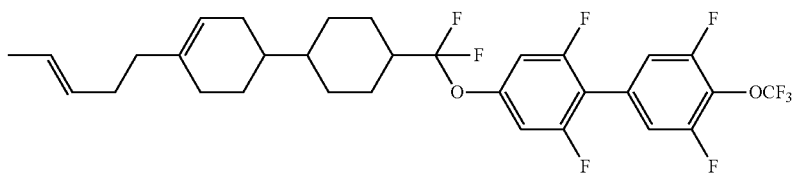 |
| 176 | 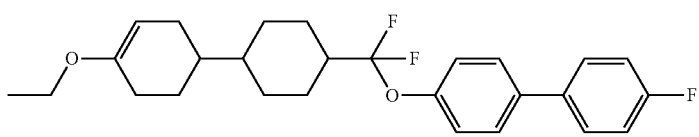 |
| 177 | 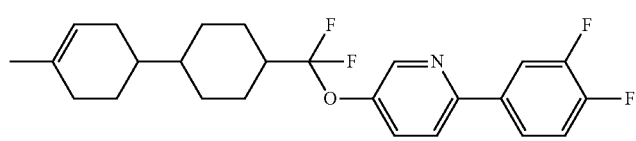 [SMILES: CC1=CCC(C2CCC(C(F)(F)Oc3ccc(-c4ccc(F)c(F)c4)nc3)CC2)CC1] |
| 178 | 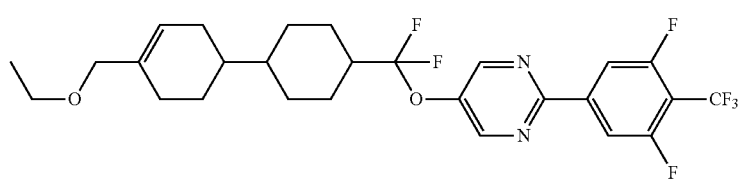 [SMILES: CCOCC1=CCC(C2CCC(C(F)(F)Oc3cnc(-c4cc(F)c(C(F)(F)F)c(F)c4)nc3)CC2)CC1] |
| 179 | 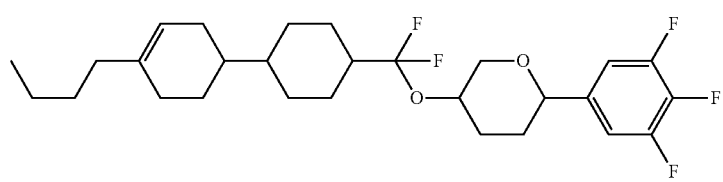 [SMILES: CCCCC1=CCC(C2CCC(C(F)(F)OC3CCC(c4cc(F)c(F)c(F)c4)OC3)CC2)CC1] |
| 180 | 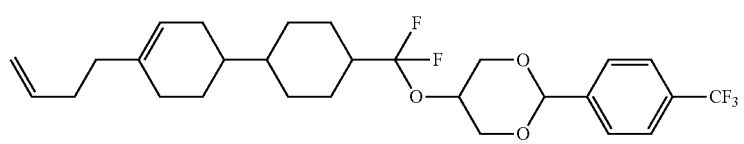 [SMILES: C=CCCC1=CCC(C2CCC(C(F)(F)OC3COC(c4ccc(C(F)(F)F)cc4)OC3)CC2)CC1] |
| 181 | 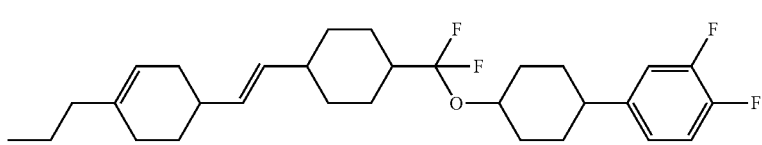 [SMILES: CCCC1=CCC(/C=C/C2CCC(C(F)(F)OC3CCC(c4ccc(F)c(F)c4)CC3)CC2)CC1] |
| 182 | 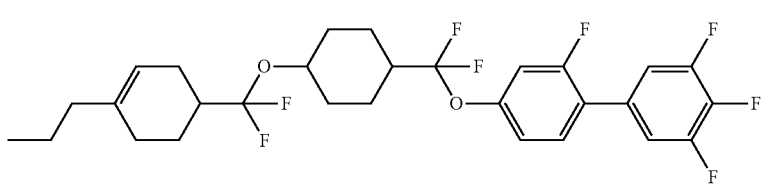 [SMILES: CCCC1=CCC(C(F)(F)OC2CCC(C(F)(F)Oc3ccc(-c4cc(F)c(F)c(F)c4)c(F)c3)CC2)CC1] |
| 183 | 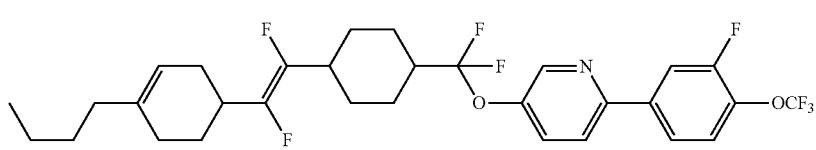 [SMILES: CCCCC1=CCC(/C(F)=C(\F)C2CCC(C(F)(F)Oc3ccc(-c4ccc(OC(F)(F)F)c(F)c4)nc3)CC2)CC1] |
| 184 | 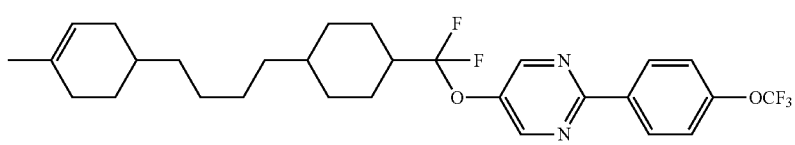 |

-continued
| No. |
|---|
| 185 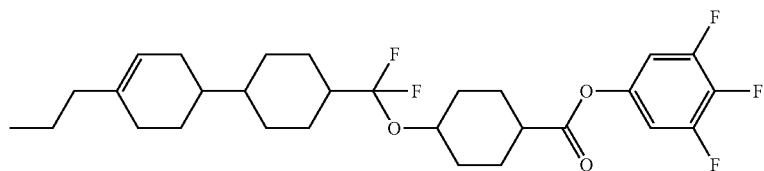 |
| 186 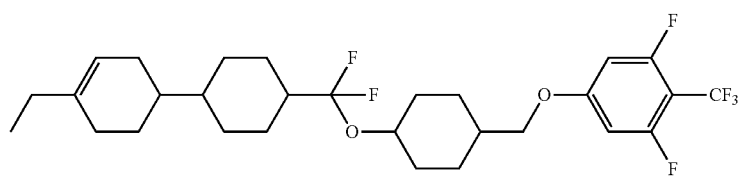 [SMILES: CCC1=CCC(C2CCC(C(F)(F)OC3CCC(COc4cc(F)c(C(F)(F)F)c(F)c4)CC3)CC2)CC1] |
| 187 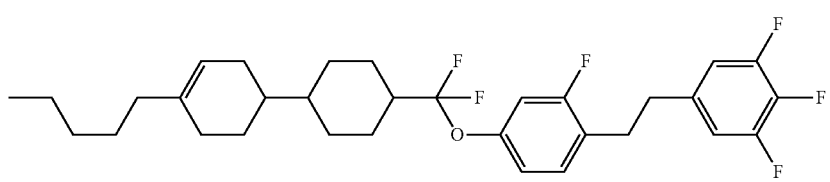 [SMILES: CCCCCC1=CCC(C2CCC(C(F)(F)Oc3ccc(CCc4cc(F)c(F)c(F)c4)c(F)c3)CC2)CC1] |
| 188 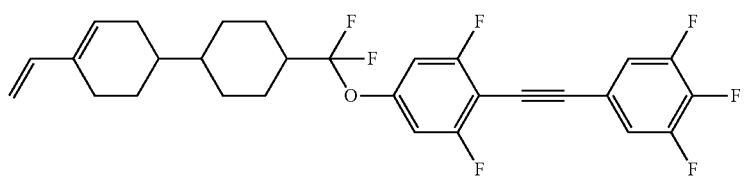 [SMILES: C=CC1=CCC(C2CCC(C(F)(F)Oc3cc(F)c(C#Cc4cc(F)c(F)c(F)c4)c(F)c3)CC2)CC1] |
| 189 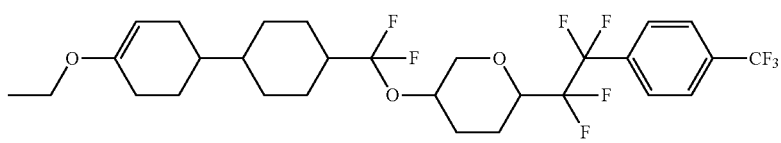 [SMILES: CCOC1=CCC(C2CCC(C(F)(F)OC3CCC(C(F)(F)C(F)(F)c4ccc(C(F)(F)F)cc4)OC3)CC2)CC1] |
| 190 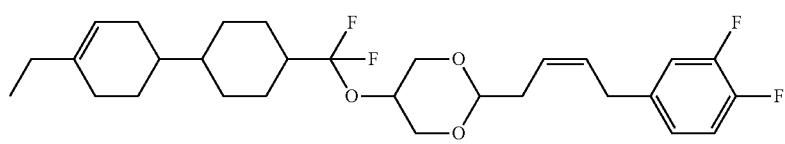 [SMILES: CCC1=CCC(C2CCC(C(F)(F)OC3COC(C/C=C\Cc4ccc(F)c(F)c4)OC3)CC2)CC1] |
| 191 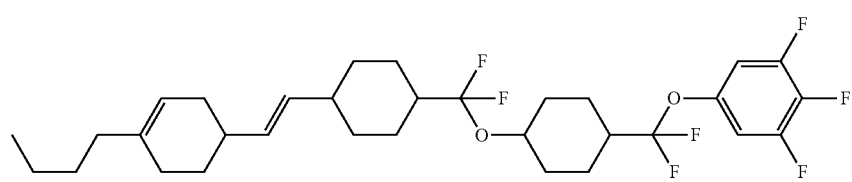 [SMILES: CCCCC1=CCC(/C=C/C2CCC(C(F)(F)OC3CCC(C(F)(F)Oc4cc(F)c(F)c(F)c4)CC3)CC2)CC1] |
| 192 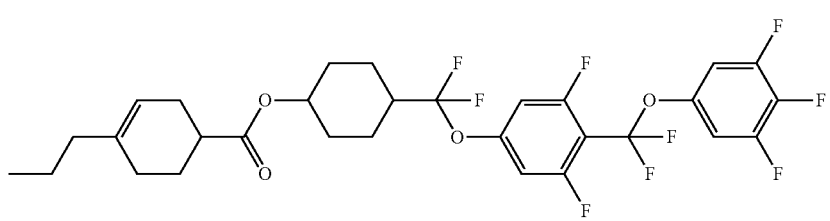 [SMILES: CCCC1=CCC(C(=O)OC2CCC(C(F)(F)Oc3cc(F)c(C(F)(F)Oc4cc(F)c(F)c(F)c4)c(F)c3)CC2)CC1] |
| 193 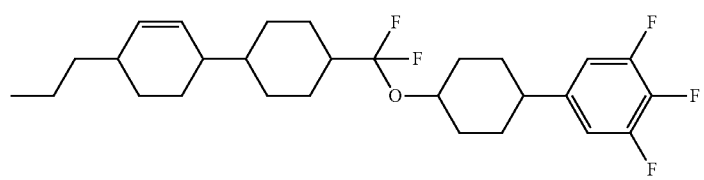 [SMILES: CCCC1C=CC(C2CCC(C(F)(F)OC3CCC(c4cc(F)c(F)c(F)c4)CC3)CC2)CC1] |

-continued
| No. | |
|---|---|
| 194 | 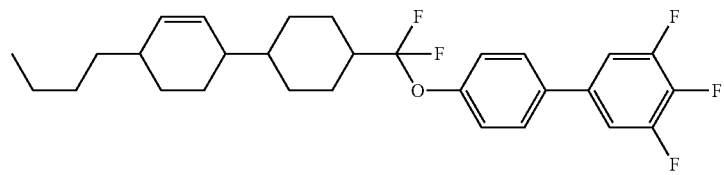 [SMILES: CCCCC1C=CC(C2CCC(C(F)(F)Oc3ccc(-c4cc(F)c(F)c(F)c4)cc3)CC2)CC1] |
| 195 | 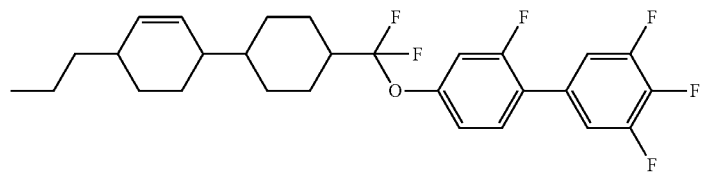 [SMILES: CCCC1C=CC(C2CCC(C(F)(F)Oc3ccc(-c4cc(F)c(F)c(F)c4)c(F)c3)CC2)CC1] |
| 196 | 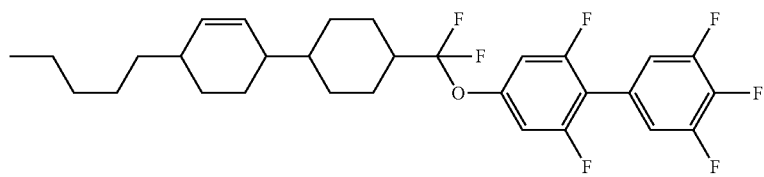 [SMILES: CCCCCC1C=CC(C2CCC(C(F)(F)Oc3cc(F)c(-c4cc(F)c(F)c(F)c4)c(F)c3)CC2)CC1] |
| 197 | 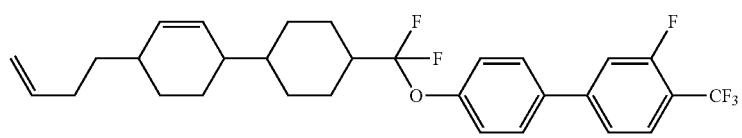 |
| 198 | 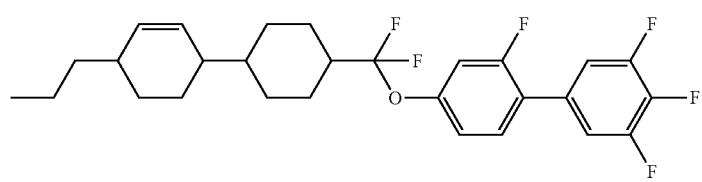 |
| 199 | 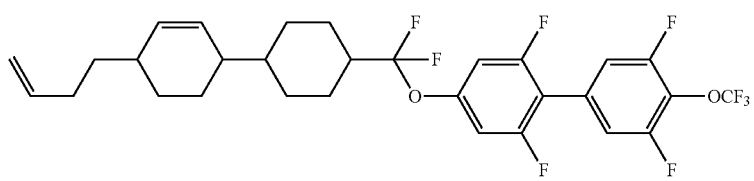 [SMILES: C=CCCC1C=CC(C2CCC(C(F)(F)Oc3cc(F)c(-c4cc(F)c(OC(F)(F)F)c(F)c4)c(F)c3)CC2)CC1] |
| 200 | 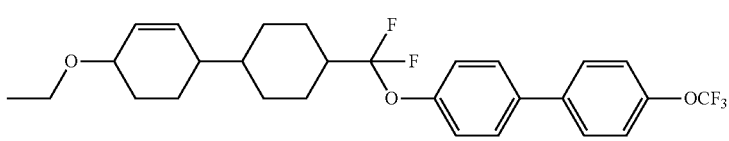 [SMILES: CCOC1C=CC(C2CCC(C(F)(F)Oc3ccc(-c4ccc(OC(F)(F)F)cc4)cc3)CC2)CC1] |
| 201 | 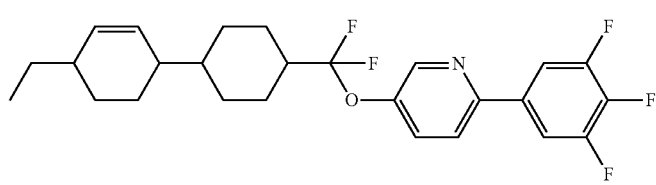 [SMILES: CCC1C=CC(C2CCC(C(F)(F)Oc3ccc(-c4cc(F)c(F)c(F)c4)nc3)CC2)CC1] |
| 202 | 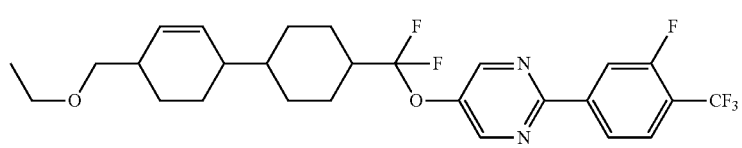 [SMILES: CCOCC1C=CC(C2CCC(C(F)(F)Oc3cnc(-c4ccc(C(F)(F)F)c(F)c4)nc3)CC2)CC1] |

-continued
| No. | |
|---|---|
| 203 | 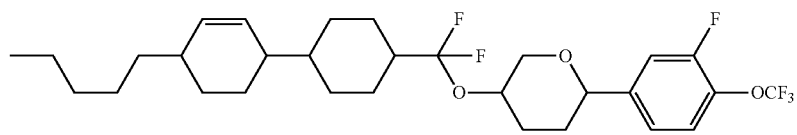 [SMILES: CCCCCC1C=CC(C2CCC(C(F)(F)OC3CCC(c4ccc(OC(F)(F)F)c(F)c4)OC3)CC2)CC1] |
| 204 | 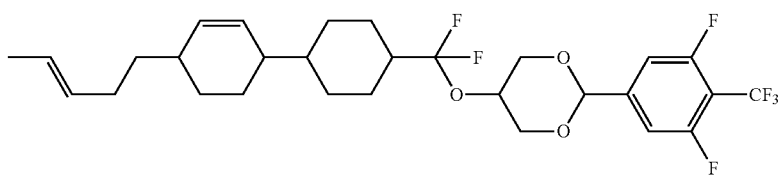 |
| 205 | 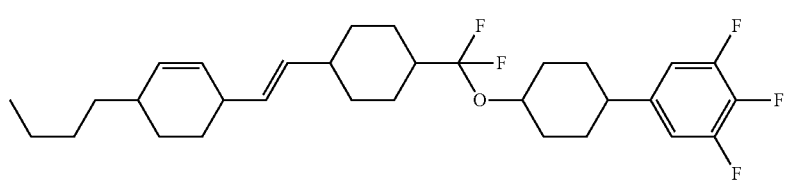 [SMILES: CCCCC1C=CC(/C=C/C2CCC(C(F)(F)OC3CCC(c4cc(F)c(F)c(F)c4)CC3)CC2)CC1] |
| 206 | 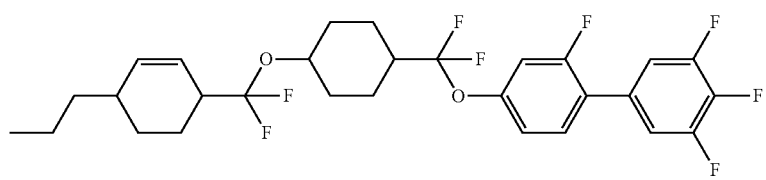 |
| 207 | 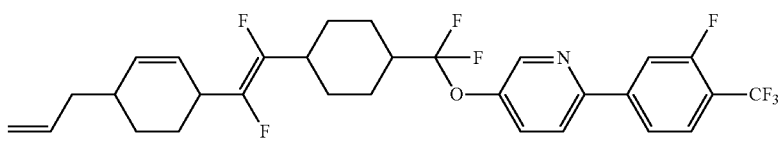 [SMILES: C=CCC1C=CC(/C(F)=C(\F)C2CCC(C(F)(F)Oc3ccc(-c4ccc(C(F)(F)F)c(F)c4)nc3)CC2)CC1] |
| 208 | 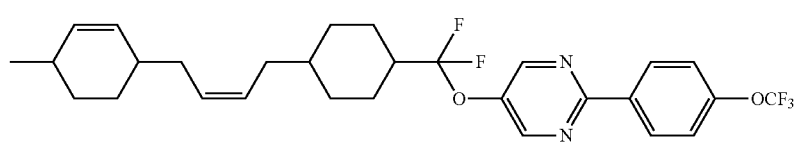 |
| 209 | 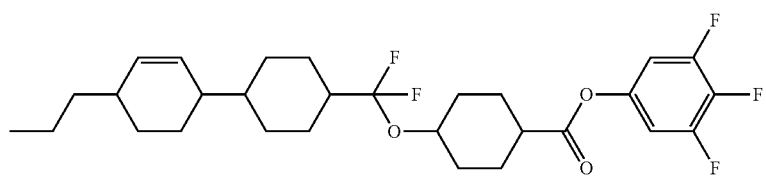 [SMILES: CCCC1C=CC(C2CCC(C(F)(F)OC3CCC(C(=O)Oc4cc(F)c(F)c(F)c4)CC3)CC2)CC1] |
| 210 | 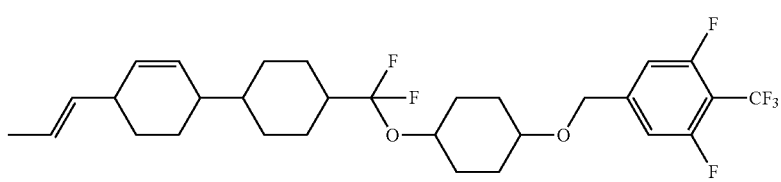 [SMILES: C/C=C/C1C=CC(C2CCC(C(F)(F)OC3CCC(OCc4cc(F)c(C(F)(F)F)c(F)c4)CC3)CC2)CC1] |
| 211 | 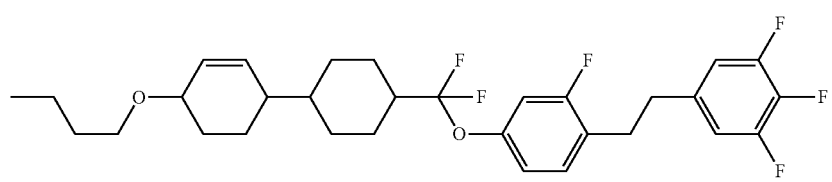 [SMILES: CCCCOC1C=CC(C2CCC(C(F)(F)Oc3ccc(CCc4cc(F)c(F)c(F)c4)c(F)c3)CC2)CC1] |

| No. | |
|---|---|
| 212 | 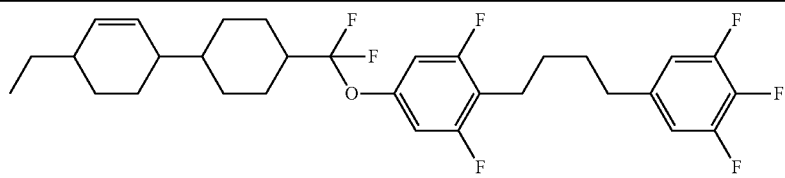 |
| 213 | 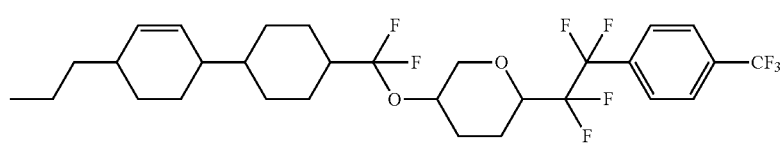 [SMILES: CCCC1C=CC(C2CCC(C(F)(F)OC3CCC(C(F)(F)C(F)(F)c4ccc(C(F)(F)F)cc4)OC3)CC2)CC1] |
| 214 | 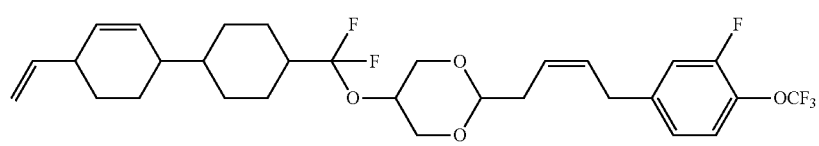 [SMILES: C=CC1C=CC(C2CCC(C(F)(F)OC3COC(C/C=C\Cc4ccc(OC(F)(F)F)c(F)c4)OC3)CC2)CC1] |
| 215 | 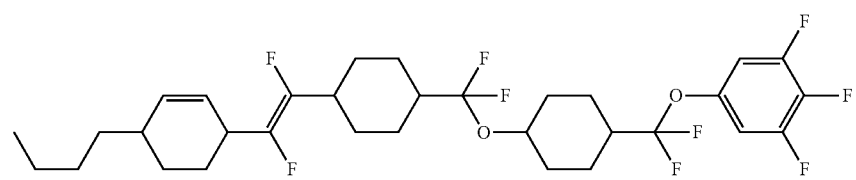 [SMILES: CCCCC1C=CC(/C(F)=C(\F)C2CCC(C(F)(F)OC3CCC(C(F)(F)Oc4cc(F)c(F)c(F)c4)CC3)CC2)CC1] |
| 216 | 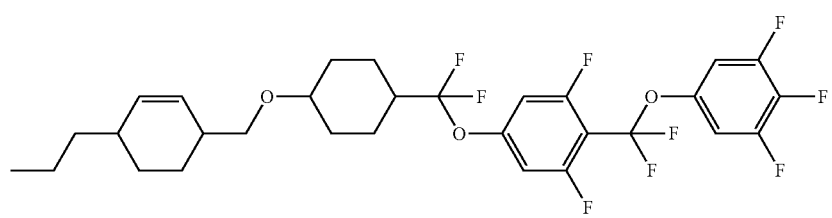 |
| 217 | 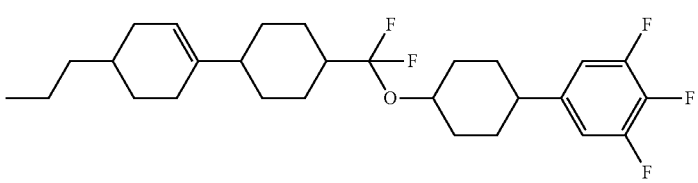 [SMILES: CCCC1CC=C(C2CCC(C(F)(F)OC3CCC(c4cc(F)c(F)c(F)c4)CC3)CC2)CC1] |
| 218 | 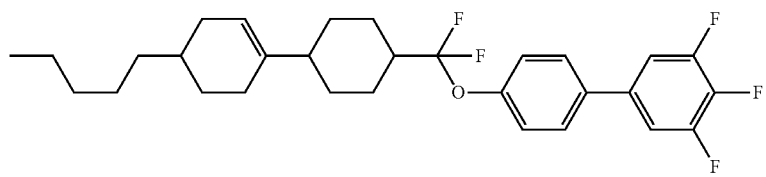 |
| 219 | 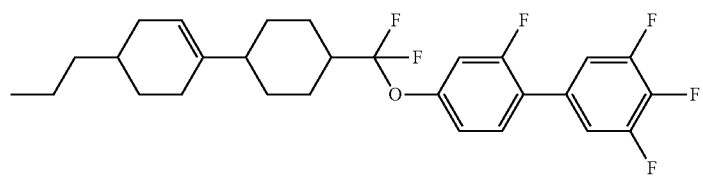 |
| 220 | 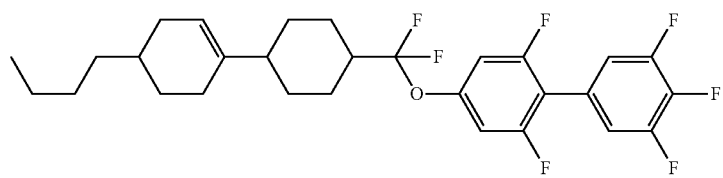 |

| No. | |
|---|---|
| 221 | 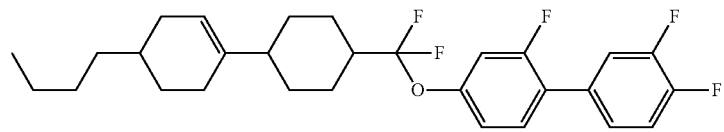 [SMILES: CCCCC1CC=C(C2CCC(C(F)(F)Oc3ccc(-c4ccc(F)c(F)c4)c(F)c3)CC2)CC1] |
| 222 | 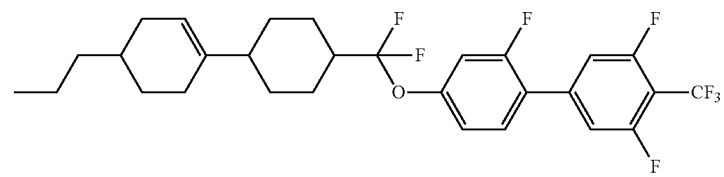 [SMILES: CCCC1CC=C(C2CCC(C(F)(F)Oc3ccc(-c4cc(F)c(C(F)(F)F)c(F)c4)c(F)c3)CC2)CC1] |
| 223 | 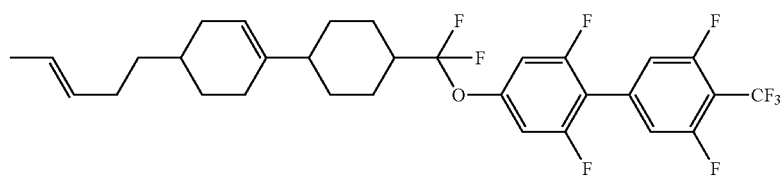 [SMILES: C/C=C/CCC1CC=C(C2CCC(C(F)(F)Oc3cc(F)c(-c4cc(F)c(C(F)(F)F)c(F)c4)c(F)c3)CC2)CC1] |
| 224 | 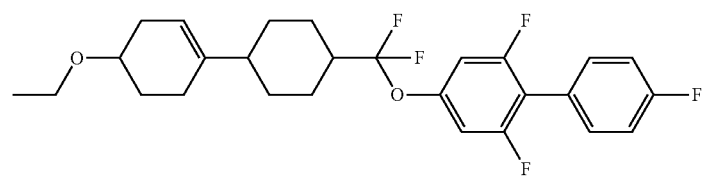 [SMILES: CCOC1CC=C(C2CCC(C(F)(F)Oc3cc(F)c(-c4ccc(F)cc4)c(F)c3)CC2)CC1] |
| 225 | 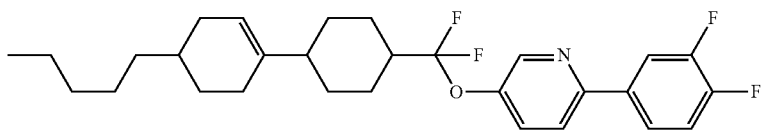 |
| 226 | 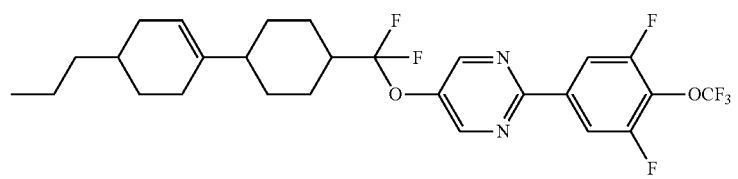 [SMILES: CCCC1CC=C(C2CCC(C(F)(F)Oc3cnc(-c4cc(F)c(OC(F)(F)F)c(F)c4)nc3)CC2)CC1] |
| 227 | 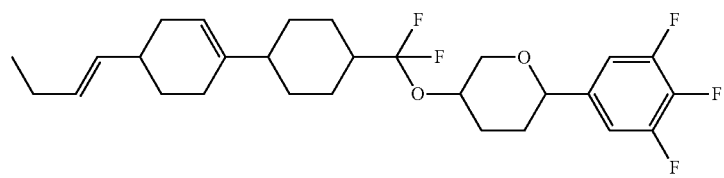 [SMILES: CC/C=C/C1CC=C(C2CCC(C(F)(F)OC3CCC(c4cc(F)c(F)c(F)c4)OC3)CC2)CC1] |
| 228 | 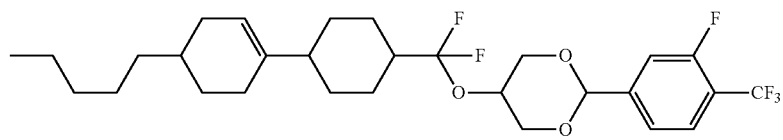 [SMILES: CCCCCC1CC=C(C2CCC(C(F)(F)OC3COC(c4ccc(C(F)(F)F)c(F)c4)OC3)CC2)CC1] |
| 229 | 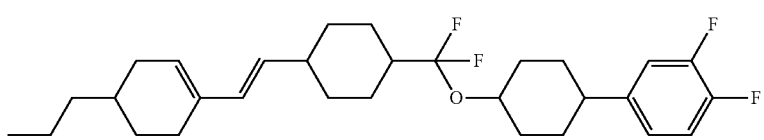 [SMILES: CCCC1CC=C(/C=C/C2CCC(C(F)(F)OC3CCC(c4ccc(F)c(F)c4)CC3)CC2)CC1] |

-continued
| No. |
|---|
| 230 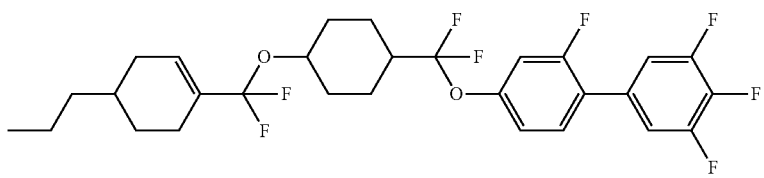 |
| 231 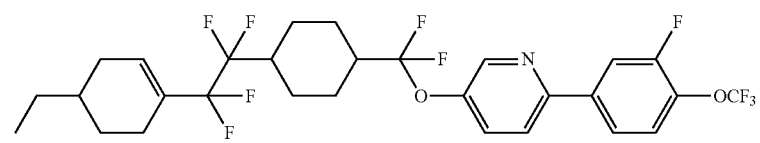 [SMILES: CCC1CC=C(C(F)(F)C(F)(F)C2CCC(C(F)(F)Oc3ccc(-c4ccc(OC(F)(F)F)c(F)c4)nc3)CC2)CC1] |
| 232 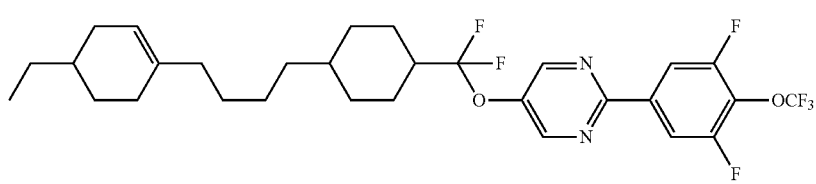 [SMILES: CCC1CC=C(CCCCC2CCC(C(F)(F)Oc3cnc(-c4cc(F)c(OC(F)(F)F)c(F)c4)nc3)CC2)CC1] |
| 233 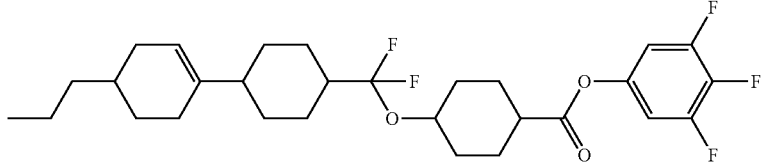 [SMILES: CCCC1CC=C(C2CCC(C(F)(F)OC3CCC(C(=O)Oc4cc(F)c(F)c(F)c4)CC3)CC2)CC1] |
| 234 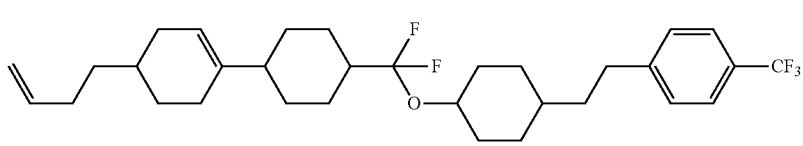 [SMILES: C=CCCC1CC=C(C2CCC(C(F)(F)OC3CCC(CCc4ccc(C(F)(F)F)cc4)CC3)CC2)CC1] |
| 235 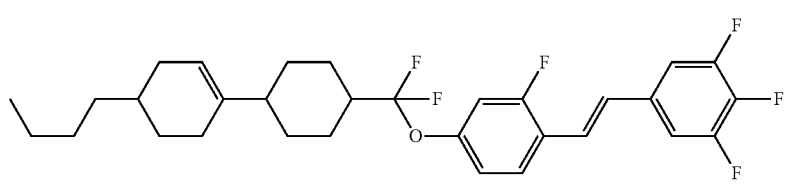 [SMILES: CCCCC1CC=C(C2CCC(C(F)(F)Oc3ccc(/C=C/c4cc(F)c(F)c(F)c4)c(F)c3)CC2)CC1] |
| 236 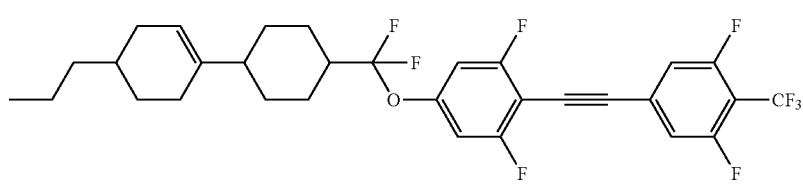 [SMILES: CCCC1CC=C(C2CCC(C(F)(F)Oc3cc(F)c(C#Cc4cc(F)c(C(F)(F)F)c(F)c4)c(F)c3)CC2)CC1] |
| 237 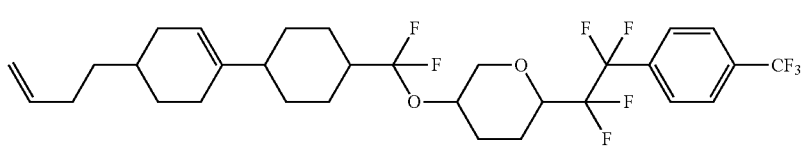 [SMILES: C=CCCC1CC=C(C2CCC(C(F)(F)OC3CCC(C(F)(F)C(F)(F)c4ccc(C(F)(F)F)cc4)OC3)CC2)CC1] |
| 238 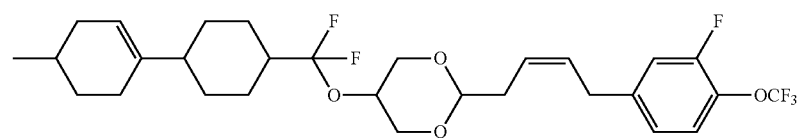 [SMILES: CC1CC=C(C2CCC(C(F)(F)OC3COC(C/C=C\Cc4ccc(OC(F)(F)F)c(F)c4)OC3)CC2)CC1] |

| No. | |
|---|---|
| 239 | 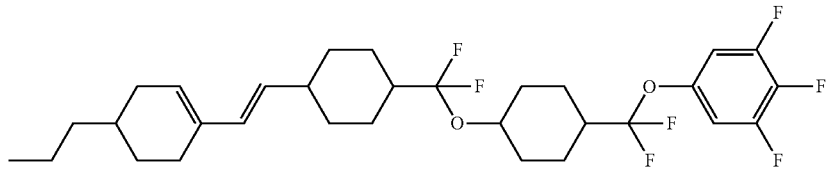 [SMILES: CCCC1CC=C(/C=C/C2CCC(C(F)(F)OC3CCC(C(F)(F)Oc4cc(F)c(F)c(F)c4)CC3)CC2)CC1] |
| 240 | 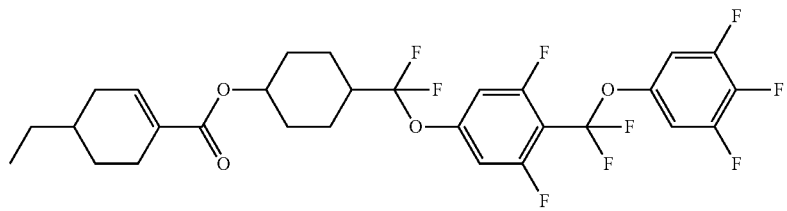 [SMILES: CCC1CC=C(C(=O)OC2CCC(C(F)(F)Oc3cc(F)c(C(F)(F)Oc4cc(F)c(F)c(F)c4)c(F)c3)CC2)CC1] |

2. Example of Composition

The composition of the invention will be described in detail by way of Examples. The invention includes a mixture of a composition in Composition Example 1 and a composition in Composition Example 2. The invention also includes a mixture of at least two compositions in Composition Examples. The compounds in Composition Examples were represented using symbols according to definitions in Table 3 described below. In Table 3, a configuration of 1,4-cyclohexylene is trans. A parenthesized number next to a symbolized compound in the Composition Examples represents a chemical formula to which the compound belongs. A symbol (-) means any other liquid crystal compound. A proportion (percentage) of the liquid crystal compound is expressed in terms of weight percent (% by weight) based on the weight of the liquid crystal composition. Values of physical properties of the composition are summarized in a last part. The physical properties were measured in accordance with the methods described above, and measured values are directly described (without extrapolation).

TABLE 3

Method for Description of Compounds using Symbols $$R-(A_1)-Z_1-\ldots-Z_n-(A_n)-R'$$

| | Symbol |
|---|---|
| 1) Left-terminal Group R— | |
| $C_nH_{2n+1}-$ | n- |
| $C_nH_{2n+1}O-$ | nO- |
| $C_mH_{2m+1}OC_nH_{2n}-$ | mOn- |
| $CH_2=CH-$ | V- |
| $C_nH_{2n+1}-CH=CH-$ | nV- |
| $CH_2=CH-C_nH_{2n}-$ | Vn- |
| $C_mH_{2m+1}-CH=CH-C_nH_{2n}-$ | mVn- |
| $CF_2=CH-$ | VFF- |
| $CF_2=CH-C_nH_{2n}-$ | VFFn- |
| 2) Right-terminal Group —R' | |
| $-C_nH_{2n+1}$ | -n |
| $-OC_nH_{2n+1}$ | -On |
| $-COOCH_3$ | -EMe |
| $-CH=CH_2$ | -V |
| $-CH=CH-C_nH_{2n+1}$ | -Vn |
| $-C_nH_{2n}-CH=CH_2$ | -nV |
| $-C_mH_{2m}-CH=CH-C_nH_{2n+1}$ | -mVn |

TABLE 3-continued

Method for Description of Compounds using Symbols $$R-(A_1)-Z_1-\ldots-Z_n-(A_n)-R'$$

| | Symbol |
|---|---|
| $-CH=CF_2$ | -VFF |
| $-F$ | -F |
| $-Cl$ | -CL |
| $-OCF_3$ | -OCF3 |
| $-OCF_2H$ | -OCF2H |
| $-CF_3$ | -CF3 |
| $-OCH=CH-CF_3$ | -OVCF3 |
| $-C\equiv N$ | -C |
| 3) Bonding Group —Zn— | |
| $-C_nH_{2n}-$ | n |
| $-COO-$ | E |
| $-CH=CH-$ | V |
| $-CH_2O-$ | 1O |
| $-OCH_2-$ | O1 |
| $-CF_2O-$ | X |
| $-C\equiv C-$ | T |
| 4) Ring Structure -An- | |
| cyclohexane ring | H |
| benzene ring | B |
| fluorobenzene (F) | B(F) |
| fluorobenzene (2F) | B(2F) |

TABLE 3-continued

Method for Description of Compounds using Symbols

R—(A$_1$)—Z$_1$— . . . —Z$_n$—(A$_n$)—R'

| | Symbol |
|---|---|
| 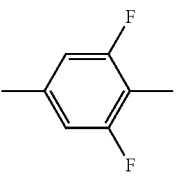 | B(F,F) |
| 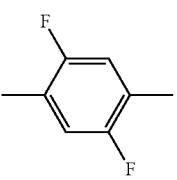 | B(2F,5F) |
| 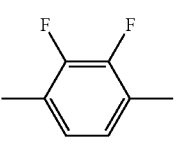 | B(2F,3F) |
| 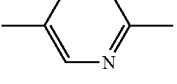 | Py |
| 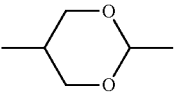 | G |
| 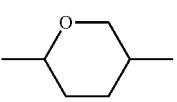 | Dh |
| 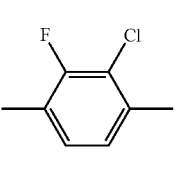 | B(2F,3CL) |
|  | Ch |
| 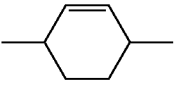 | Cx |
|  | ch |
| 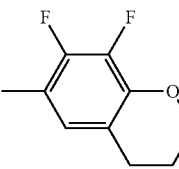 | Cro |

TABLE 3-continued

Method for Description of Compounds using Symbols

R—(A$_1$)—Z$_1$— . . . —Z$_n$—(A$_n$)—R'

Symbol

5) Examples of Description

Example 1                3-ChHB(F,F)XB(F,F)-F

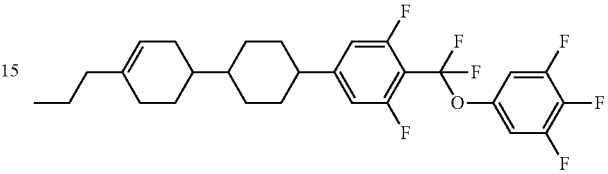

Example 2                3-BB(F,F)XB(F,F)-F

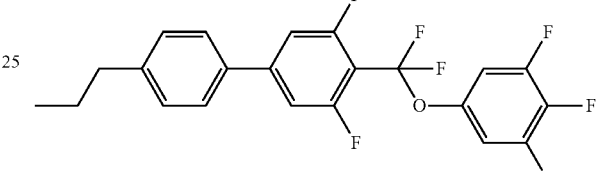

Composition Example 1

| | | |
|---|---|---|
| 3-ChHB(F,F)XB(F,F)-F | (No. 99) | 8% |
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 10% |
| 4-PyBB-F | (6-80) | 10% |
| 5-PyBB-F | (6-80) | 10% |
| 5-HBB(F)B-2 | (4-5) | 6% |
| 5-HBB(F)B-3 | (4-5) | 6% |

NI = 87.0° C.; η = 39.9 mPa · s; Δn = 0.178; Δε = 9.7.

Composition Example 2

| | | |
|---|---|---|
| 3-CxHB(F,F)XB(F,F)-F | (No. 123) | 7% |
| 2-HB-C | (8-1) | 5% |
| 3-HB-C | (8-1) | 11% |
| 3-HB-O2 | (2-5) | 13% |
| 2-BTB-1 | (2-10) | 3% |
| 3-HHB-F | (6-1) | 4% |
| 3-HHB-1 | (3-1) | 7% |
| 3-HHB-O1 | (3-1) | 5% |
| 3-HHB-3 | (3-1) | 12% |
| 3-HHEB-F | (6-10) | 4% |
| 5-HHEB-F | (6-10) | 4% |
| 2-HHB(F)-F | (6-2) | 6% |
| 3-HHB(F)-F | (6-2) | 7% |
| 5-HHB(F)-F | (6-2) | 7% |
| 3-HHB(F,F)-F | (6-3) | 5% |

Composition Example 3

| | | |
|---|---|---|
| 3-chHB(F,F)XB(F,F)-F | (No. 147) | 6% |
| 7-HB(F,F)-F | (5-4) | 3% |
| 3-HB-O2 | (2-5) | 7% |
| 2-HHB(F)-F | (6-2) | 9% |
| 3-HHB(F)-F | (6-2) | 10% |
| 5-HHB(F)-F | (6-2) | 10% |
| 2-HBB(F)-F | (6-23) | 9% |
| 3-HBB(F)-F | (6-23) | 8% |
| 5-HBB(F)-F | (6-23) | 13% |
| 2-HBB-F | (6-22) | 4% |
| 3-HBB-F | (6-22) | 4% |
| 5-HBB-F | (6-22) | 3% |
| 3-HBB(F,F)-F | (6-24) | 4% |
| 5-HBB(F,F)-F | (6-24) | 10% |

Composition Example 4

| | | |
|---|---|---|
| 3-ChHB(F,F)XB(F,F)-F | (No. 99) | 10% |
| 5-HB-CL | (5-2) | 15% |
| 3-HH-4 | (2-1) | 12% |
| 3-HH-5 | (2-1) | 4% |
| 3-HHB-F | (6-1) | 4% |
| 3-HHB-CL | (6-1) | 3% |
| 4-HHB-CL | (6-1) | 4% |
| 3-HHB(F)-F | (6-2) | 9% |
| 4-HHB(F)-F | (6-2) | 8% |
| 5-HHB(F)-F | (6-2) | 8% |
| 7-HHB(F)-F | (6-2) | 8% |
| 5-HBB(F)-F | (6-23) | 3% |
| 1O1-HBBH-5 | (4-1) | 3% |
| 3-HHBB(F,F)-F | (7-6) | 3% |
| 5-HHBB(F,F)-F | (7-6) | 3% |
| 3-HH2BB(F,F)-F | (7-15) | 3% |

NI = 108.8° C.; η = 19.8 mPa · s; Δn = 0.089; Δε = 5.4.

Composition Example 5

| | | |
|---|---|---|
| 3-CxHB(F,F)XB(F,F)-F | (No. 123) | 9% |
| 3-HHB(F,F)-F | (6-3) | 8% |
| 3-H2HB(F,F)-F | (6-15) | 6% |
| 4-H2HB(F,F)-F | (6-15) | 6% |
| 5-H2HB(F,F)-F | (6-15) | 8% |
| 3-HBB(F,F)-F | (6-24) | 20% |
| 5-HBB(F,F)-F | (6-24) | 18% |
| 3-H2BB(F,F)-F | (6-27) | 10% |
| 5-HHBB(F,F)-F | (7-6) | 3% |
| 5-HHEBB-F | (7-17) | 3% |
| 3-HH2BB(F,F)-F | (7-15) | 3% |
| 1O1-HBBH-4 | (4-1) | 3% |
| 1O1-HBBH-5 | (4-1) | 3% |

Composition Example 6

| | | |
|---|---|---|
| 3-chHB(F,F)XB(F,F)-F | (No. 147) | 8% |
| 5-HB-F | (5-2) | 10% |
| 6-HB-F | (5-2) | 8% |
| 7-HB-F | (5-2) | 7% |
| 2-HHB-OCF3 | (6-1) | 6% |
| 3-HHB-OCF3 | (6-1) | 7% |
| 4-HHB-OCF3 | (6-1) | 7% |
| 5-HHB-OCF3 | (6-1) | 4% |
| 3-HH2B-OCF3 | (6-4) | 4% |
| 5-HH2B-OCF3 | (6-4) | 4% |
| 3-HHB(F,F)-OCF2H | (6-3) | 4% |
| 3-HHB(F,F)-OCF3 | (6-3) | 4% |
| 3-HH2B(F)-F | (6-5) | 3% |
| 3-HBB(F)-F | (6-23) | 9% |
| 5-HBB(F)-F | (6-23) | 9% |
| 5-HBBH-3 | (4-1) | 3% |
| 3-HB(F)BH-3 | (4-2) | 3% |

Composition Example 7

| | | |
|---|---|---|
| 3-ChHB(F,F)XB(F,F)-F | (No. 99) | 7% |
| 5-HB-CL | (5-2) | 10% |
| 3-HH-4 | (2-1) | 8% |
| 3-HHB-1 | (3-1) | 5% |
| 3-HHB(F,F)-F | (6-3) | 6% |
| 3-HBB(F,F)-F | (6-24) | 19% |
| 5-HBB(F,F)-F | (6-24) | 15% |
| 3-HHEB(F,F)-F | (6-12) | 9% |
| 4-HHEB(F,F)-F | (6-12) | 3% |
| 5-HHEB(F,F)-F | (6-12) | 3% |
| 2-HBEB(F,F)-F | (6-39) | 3% |
| 3-HBEB(F,F)-F | (6-39) | 3% |
| 5-HBEB(F,F)-F | (6-39) | 3% |
| 3-HHBB(F,F)-F | (7-6) | 6% |

NI = 81.2° C.; η = 24.1 mPa · s; Δn = 0.103; Δε = 9.5.

Composition Example 8

| | | |
|---|---|---|
| 3-CxHB(F,F)XB(F,F)-F | (No. 123) | 8% |
| 3-HB-CL | (5-2) | 4% |
| 5-HB-CL | (5-2) | 3% |
| 3-HHB-OCF3 | (6-1) | 4% |
| 3-H2HB-OCF3 | (6-13) | 4% |
| 5-H4HB-OCF3 | (6-19) | 15% |
| V-HHB(F)-F | (6-2) | 5% |
| 3-HHB(F)-F | (6-2) | 5% |
| 5-HHB(F)-F | (6-2) | 5% |
| 3-H4HB(F,F)-CF3 | (6-21) | 8% |
| 5-H4HB(F,F)-CF3 | (6-21) | 8% |
| 5-H2HB(F,F)-F | (6-15) | 5% |
| 5-H4HB(F,F)-F | (6-21) | 6% |
| 2-H2BB(F)-F | (6-14) | 5% |
| 3-H2BB(F)-F | (6-14) | 10% |
| 3-HBEB(F,F)-F | (6-12) | 5% |

Composition Example 9

| | | |
|---|---|---|
| 3-chHB(F,F)XB(F,F)-F | (No. 147) | 5% |
| 5-HB-CL | (5-2) | 15% |
| 7-HB(F,F)-F | (5-4) | 3% |
| 3-HH-4 | (2-1) | 10% |
| 3-HH-5 | (2-1) | 5% |
| 3-HB-O2 | (2-5) | 13% |
| 3-HHB-1 | (3-1) | 8% |
| 3-HHB-O1 | (3-1) | 6% |
| 2-HHB(F)-F | (6-2) | 6% |
| 3-HHB(F)-F | (6-2) | 6% |
| 5-HHB(F)-F | (6-2) | 7% |
| 3-HHB(F,F)-F | (6-3) | 6% |
| 3-H2HB(F,F)-F | (6-15) | 5% |
| 4-H2HB(F,F)-F | (6-15) | 5% |

Composition Example 10

| | | |
|---|---|---|
| 3-ChHB(F,F)XB(F,F)-F | (No. 99) | 6% |
| 5-HB-CL | (5-2) | 3% |
| 7-HB(F)-F | (5-3) | 6% |
| 3-HH-4 | (2-1) | 9% |
| 3-HH-EMe | (2-2) | 22% |
| 3-HHEB-F | (6-10) | 7% |
| 5-HHEB-F | (6-10) | 7% |
| 3-HHEB(F,F)-F | (6-12) | 10% |
| 4-HHEB(F,F)-F | (6-12) | 5% |
| 4-HGB(F,F)-F | (6-103) | 5% |
| 5-HGB(F,F)-F | (6-103) | 5% |
| 2-H2GB(F,F)-F | (6-106) | 4% |
| 3-H2GB(F,F)-F | (6-106) | 5% |
| 5-GHB(F,F)-F | (6-109) | 6% |

NI = 79.8° C.; η = 21.8 mPa · s; Δn = 0.066; Δε = 6.7.

Composition Example 11

| | | |
|---|---|---|
| 3-CxHB(F,F)XB(F,F)-F | (No. 123) | 7% |
| 3-HB-O1 | (2-5) | 13% |
| 3-HH-4 | (2-1) | 5% |
| 3-HB(2F,3F)-O2 | (9-1) | 10% |
| 5-HB(2F,3F)-O2 | (9-1) | 11% |
| 2-HHB(2F,3F)-1 | (10-1) | 12% |
| 3-HHB(2F,3F)-1 | (10-1) | 12% |
| 3-HHB(2F,3F)-O2 | (10-1) | 13% |
| 5-HHB(2F,3F)-O2 | (10-1 ) | 12% |
| 3-HHB-1 | (3-1) | 5% |

Composition Example 12

| | | |
|---|---|---|
| 3-chHB(F,F)XB(F,F)-F | (No. 147) | 9% |
| 2-HH-5 | (2-1) | 3% |
| 3-HH-4 | (2-1) | 13% |
| 3-HH-5 | (2-1) | 3% |
| 3-HB-O2 | (2-5) | 11% |
| 3-H2B(2F,3F)-O2 | (9-4) | 15% |
| 5-H2B(2F,3F)-O2 | (9-4) | 13% |
| 3-HHB(2F,3CL)-O2 | (10-12) | 5% |
| 2-HBB(2F,3F)-O2 | (10-7) | 3% |
| 3-HBB(2F,3F)-O2 | (10-7) | 8% |
| 5-HBB(2F,3F)-O2 | (10-7) | 8% |
| 3-HHB-1 | (3-1) | 3% |
| 3-HHB-3 | (3-1) | 3% |
| 3-HHB-O1 | (3-1) | 3% |

Composition Example 13

| | | |
|---|---|---|
| 3-ChHB(F,F)XB(F,F)-F | (No. 99) | 10% |
| 2-HH-3 | (2-1) | 18% |
| 3-HH-4 | (2-1) | 8% |
| 1-BB-3 | (2-8) | 8% |
| 3-HB-O2 | (2-5) | 3% |
| 3-BB(2F,3F)-O2 | (9-3) | 8% |
| 5-BB(2F,3F)-O2 | (9-3) | 5% |
| 2-HH1OB(2F,3F)-O2 | (10-5) | 9% |
| 3-HH1OB(2F,3F)-O2 | (10-5) | 19% |
| 5-HBB(2F,3F)-O2 | (10-7) | 4% |
| 3-HHB-1 | (3-1) | 3% |
| 3-HHB-O1 | (3-1) | 3% |
| 5-B(F)BB-2 | (3-8) | 2% |

NI = 76.8° C.; η = 19.5 mPa · s; Δn = 0.101; Δε = −2.9.

Composition Example 14

| | | |
|---|---|---|
| 3-CxHB(F,F)XB(F,F)-F | (No. 123) | 6% |
| 2-HH-3 | (2-1) | 14% |
| 7-HB-1 | (2-5) | 10% |
| 5-HB-O2 | (2-5) | 7% |
| 3-HB(2F,3F)-O2 | (9-1) | 16% |
| 5-HB(2F,3F)-O2 | (9-1) | 15% |
| 3-HHB(2F,3CL)-O2 | (10-12) | 3% |
| 4-HHB(2F,3CL)-O2 | (10-12) | 3% |
| 5-HHB(2F,3CL)-O2 | (10-12) | 2% |
| 3-HH1OCro(7F,8F)-5 | (13-6) | 4% |
| 5-HBB(F)B-2 | (4-5) | 10% |
| 5-HBB(F)B-3 | (4-5) | 10% |

Composition Example 15

| | | |
|---|---|---|
| 3-chHB(F,F)XB(F,F)-F | (No. 147) | 10% |
| 2-HH-3 | (2-1) | 5% |
| 1-BB-3 | (2-8) | 8% |
| 3-HH-V | (2-1) | 20% |
| 3-BB(2F,3F)-O2 | (9-3) | 11% |
| 2-HH1OB(2F,3F)-O2 | (10-5) | 18% |
| 3-HH1OB(2F,3F)-O2 | (10-5) | 12% |
| 3-HHB-1 | (3-1) | 7% |
| 5-B(F)BB-2 | (3-8) | 5% |
| 2-BB(2F,3F)B-3 | (11-1) | 4% |

Composition Example 16

| | | |
|---|---|---|
| 3-ChHB(F,F)XB(F,F)-F | (No. 99) | 9% |
| 2-HH-3 | (2-1) | 6% |
| 1-BB-3 | (2-8) | 5% |
| 3-HH-V1 | (2-1) | 8% |
| 1V2-HH-1 | (2-1) | 8% |
| 1V2-HH-3 | (2-1) | 7% |
| 3-BB(2F,3F)-O2 | (9-3) | 6% |
| 5-BB(2F,3F)-O2 | (9-3) | 3% |
| 3-H1OB(2F,3F)-O2 | (9-5) | 6% |
| 2-HH1OB(2F,3F)-O2 | (10-5) | 8% |
| 3-HH1OB(2F,3F)-O2 | (10-5) | 16% |
| 3-HDhB(2F,3F)-O2 | (10-3) | 5% |
| 3-HHB-1 | (3-1) | 3% |
| 3-HHB-3 | (3-1) | 2% |
| 2-BB(2F,3F)B-3 | (11-1) | 8% |

NI = 80.2° C.; η = 21.9 mPa · s; Δn = 0.106; Δε = −3.7.

Composition Example 17

| | | |
|---|---|---|
| 3-CxHB(F,F)XB(F,F)-F | (No. 123) | 5% |
| 1V2-BEB(F,F)-C | (8-15) | 6% |
| 3-HB-C | (8-1) | 16% |
| 2-BTB-1 | (2-10) | 10% |
| 5-HH-VFF | (2-1) | 26% |
| 3-HHB-1 | (3-1) | 6% |
| VFF-HHB-1 | (3-1) | 6% |
| VFF2-HHB-1 | (3-1) | 11% |

-continued

| 3-H2BTB-2 | (3-17) | 6% |
| 3-H2BTB-3 | (3-17) | 4% |
| 3-H2BTB-4 | (3-17) | 4% |

Composition Example 18

| 3-chHB(F,F)XB(F,F)-F | (No. 147) | 8% |
| 5-HB(F)B(F,F)XB(F,F)-F | (7-41) | 4% |
| 3-BB(F)B(F,F)XB(F,F)-F | (7-47) | 3% |
| 4-BB(F)B(F,F)XB(F,F)-F | (7-47) | 5% |
| 5-BB(F)B(F,F)XB(F,F)-F | (7-47) | 3% |
| 3-HH-V | (2-1) | 39% |
| 3-HH-V1 | (2-1) | 6% |
| 3-HHEH-5 | (3-13) | 3% |
| 3-HHB-1 | (3-1) | 4% |
| V-HHB-1 | (3-1) | 4% |
| V2-BB(F)B-1 | (3-6) | 5% |
| 1V2-BB-F | (5-1) | 3% |
| 3-BB(F,F)XB(F,F)-F | (6-97) | 10% |
| 3-HHBB(F,F)-F | (7-6) | 3% |

Composition Example 19

| 3-ChHB(F,F)XB(F,F)-F | (No. 99) | 5% |
| 3-GB(F)B(F,F)XB(F,F)-F | (7-57) | 4% |
| 3-BB(F)B(F,F)XB(F,F)-F | (7-47) | 3% |
| 4-BB(F)B(F,F)XB(F,F)-F | (7-47) | 6% |
| 5-BB(F)B(F,F)XB(F,F)-F | (7-47) | 3% |
| 3-HH-V | (2-1) | 38% |
| 3-HH-V1 | (2-1) | 6% |
| 3-HHEH-5 | (3-13) | 3% |
| 3-HHB-1 | (3-1) | 4% |
| V-HHB-1 | (3-1) | 6% |
| V2-BB(F)B-1 | (3-6) | 5% |
| 1V2-BB-F | (5-1) | 3% |
| 3-BB(F,F)XB(F,F)-F | (6-97) | 5% |
| 3-GB(F,F)XB(F,F)-F | (6-113) | 5% |
| 3-HHBB(F,F)-F | (7-6) | 4% |

NI = 84.6° C.; η = 15.6 mPa · s; Δn = 0.104; Δε = 7.8.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal compound of the invention has excellent physical properties. A liquid crystal composition containing the compound can be widely applied to a liquid crystal display device used in a personal computer, a television and so forth.

What is claimed is:

1. A compound represented by formula (1):

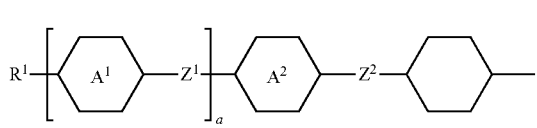

(1)

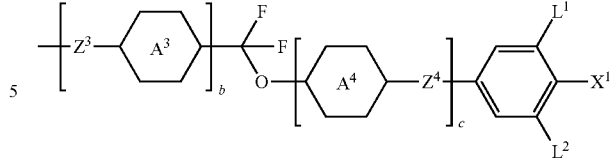

wherein, in formula (1),
R$^1$ is hydrogen, fluorine, chlorine or alkyl having 1 to 10 carbons, and in R$^1$, at least one piece of —CH$_2$— may be replaced by —O—, at least one piece of —CH$_2$CH$_2$— may be replaced by —CH=CH—, and at least one piece of hydrogen may be replaced by fluorine;
ring A$^1$, ring A$^3$ and ring A$^4$ are independently 1,4-cyclohexylene, 1,4-phenylene, 1,4-phenylene in which at least one piece of hydrogen is replaced by fluorine, tetrahydropyran-2,5-diyl, 1,3-dioxane-2,5-diyl, pyridine-2,5-diyl or pyrimidine-2,5-diyl, and ring A$^2$ is a divalent group represented by any one of formula (Ch), formula (Cx) and formula (ch);

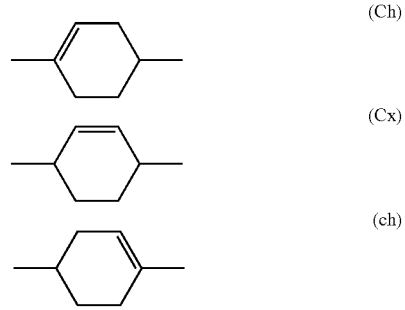

wherein, Z$^1$, Z$^2$, Z$^3$ and Z$^4$ are independently a single bond, —COO—, —OCH$_2$—, —CF$_2$O—, —CH$_2$CH$_2$—, —CH=CH—, —C≡C—, —CF$_2$CF$_2$—, —CF=CF—, —(CH$_2$)$_4$— or —CH$_2$CH=CHCH$_2$—;
X$^1$ is hydrogen, fluorine, —CF$_3$ or —OCF$_3$;
L$^1$ and L$^2$ are independently hydrogen or fluorine; and
a, b and c are independently 0 or 1, and a sum of a, b and c is 0 or 1.

2. The compound according to claim 1, wherein, in formula (1) described in claim 1,
R$^1$ is alkyl having 1 to 10 carbons, and in R$^1$, at least one piece of —CH$_2$— may be replaced by —O—, at least one piece of —CH$_2$CH$_2$— may be replaced by —CH=CH—, and at least one piece of hydrogen may be replaced by fluorine;
ring A$^1$, ring A$^3$ and ring A$^4$ are independently 1,4-cyclohexylene, 1,4-phenylene, 1,4-phenylene in which at least one piece of hydrogen is replaced by fluorine, tetrahydropyran-2,5-diyl or 1,3-dioxane-2,5-diyl, and ring A$^2$ is a divalent group represented by any one of formula (Ch), formula (Cx) and formula (ch);

(Ch)

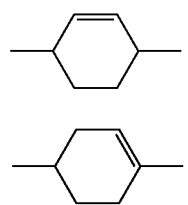

(Cx)

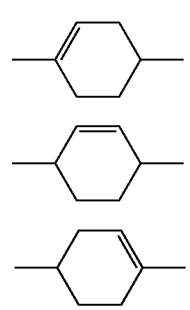

(Ch)

(ch)

(Cx)

(ch)

wherein, $Z^1$, $Z^2$, $Z^3$ and $Z^4$ are independently a single bond, —COO—, —OCH$_2$—, —CF$_2$O—, —CH$_2$CH$_2$—, —CH═CH— or —C≡C—;

$X^1$ is hydrogen, fluorine, —CF$_3$ or —OCF$_3$;

$L^1$ and $L^2$ are independently hydrogen or fluorine; and a, b and c are independently 0 or 1, and a sum of a, b and c is 0 or 1.

3. The compound according to claim 1, represented by any one of formula (1-1), formula (1-2), formula (1-3) and formula (1-4):

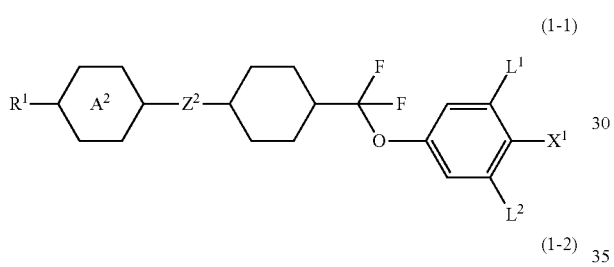

(1-1)

(1-2)

(1-3)

(1-4)

wherein, in formula (1-1) to formula (1-4),

R$^1$ is alkyl having 1 to 10 carbons, alkoxy having 1 to 10 carbons, alkenyl having 2 to 10 carbons or alkenyloxy having 2 to 10 carbons;

ring A$^1$, ring A$^3$ and ring A$^4$ are independently 1,4-cyclohexylene, 1,4-phenylene, or 1,4-phenylene in which at least one piece of hydrogen is replaced by fluorine, and ring A$^2$ is a divalent group represented by any one of formula (Ch), formula (Cx) and formula (ch);

wherein, $Z^1$, $Z^2$, $Z^3$ and $Z^4$ are independently a single bond, —COO—, —OCH$_2$—, —CF$_2$O—, —CH$_2$CH$_2$—, —CH═CH— or —C≡C—;

$X^1$ is fluorine, —CF$_3$ or —OCF$_3$; and $L^1$ and $L^2$ are independently hydrogen or fluorine.

4. The compound according to claim 1, wherein, in formula (1-1), formula (1-2), formula (1-3) and formula (1-4) described in claim 3, R$^1$ is alkyl having 1 to 10 carbons, alkoxy having 1 to 10 carbons, alkenyl having 2 to 10 carbons or alkenyloxy having 2 to 10 carbons;

ring A$^1$, ring A$^3$ and ring A$^4$ are independently 1,4-cyclohexylene, 1,4-phenylene, or 1,4-phenylene in which at least one or two pieces of hydrogen are replaced by fluorine, and ring A$^2$ is a divalent group represented by any one of formula (Ch), formula (Cx) and formula (ch);

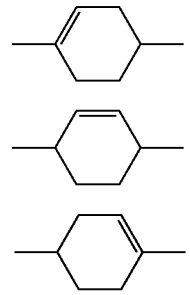

(Ch)

(Cx)

(ch)

wherein, $Z^1$, $Z^2$, $Z^3$ and $Z^4$ are independently a single bond, —COO—, —OCH$_2$—, —CF$_2$O— or —CH$_2$CH$_2$—;

$X^1$ is fluorine, —CF$_3$ or —OCF$_3$; and $L^1$ is fluorine, and $L^2$ is hydrogen or fluorine.

5. The compound according to claim 1, represented by any one of formula (1-3a), formula (1-3b) and formula (1-3c):

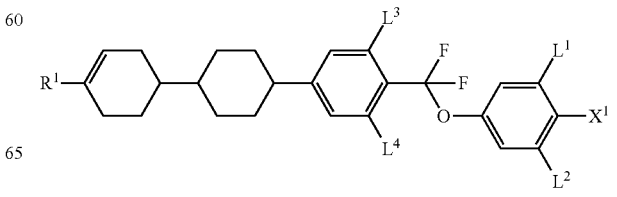

(1-3a)

-continued

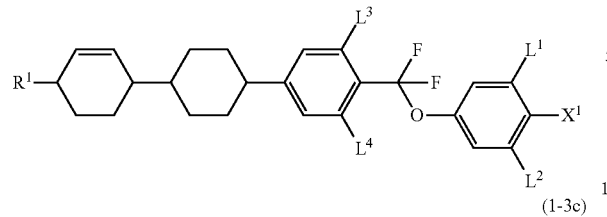
(1-3b)

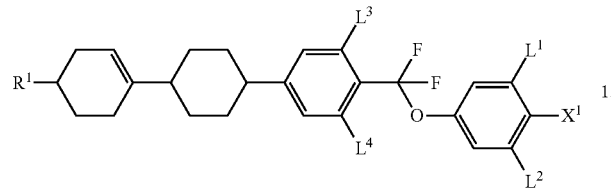
(1-3c)

wherein, in formula (1-3a), formula (1-3b) and formula (1-3c), $R^1$ is alkyl having 1 to 10 carbons, alkoxy having 1 to 10 carbons, alkenyl having 2 to 10 carbons or alkenyloxy having 2 to 10 carbons; $X^1$ is fluorine, —$CF_3$ or —$OCF_3$; and $L^1$, $L^2$, $L^3$ and $L^4$ are independently hydrogen or fluorine.

6. The compound according to claim 1, wherein, in formula (1-3a), formula (1-3b) and formula (1-3c) described in claim 5, $L^1$, $L^2$, $L^3$ and $L^4$ are independently hydrogen or fluorine, and at least two pieces of $L^1$, $L^2$, $L^3$ and $L^4$ are fluorine.

7. The compound according to claim 1, represented by any one of formula (1-2a), formula (1-2b) and formula (1-2c):

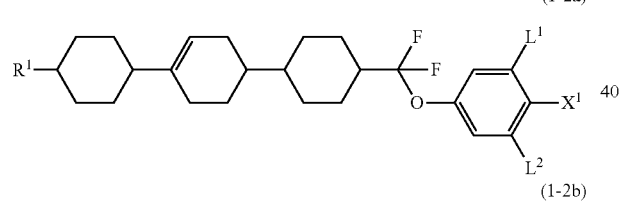
(1-2a)

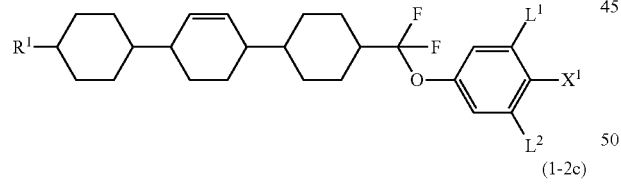
(1-2b)

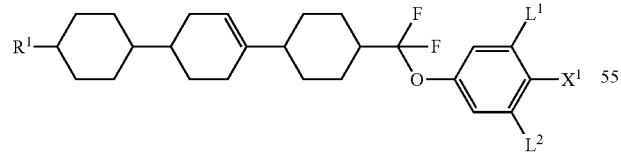
(1-2c)

wherein, in formula (1-2a), formula (1-2b) and formula (1-2c), $R^1$ is alkyl having 1 to 10 carbons, alkoxy having 1 to 10 carbons, alkenyl having 2 to 10 carbons or alkenyloxy having 2 to 10 carbons; $X^1$ is fluorine, —$CF_3$ or —$OCF_3$; and $L^1$ and $L^2$ are independently hydrogen or fluorine.

8. The compound according to claim 1, represented by any one of formula (1-2d), formula (1-2e) and formula (1-2f):

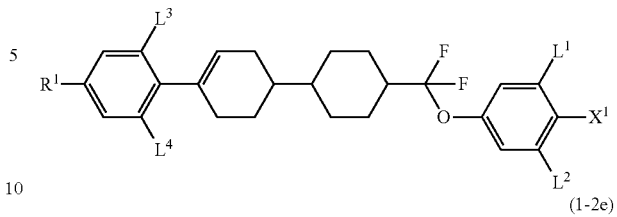
(1-2d)

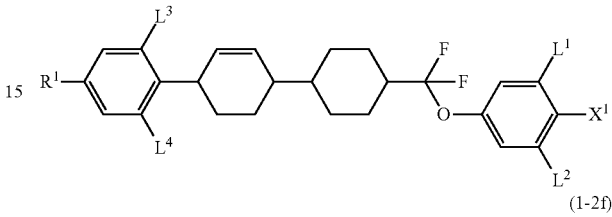
(1-2e)

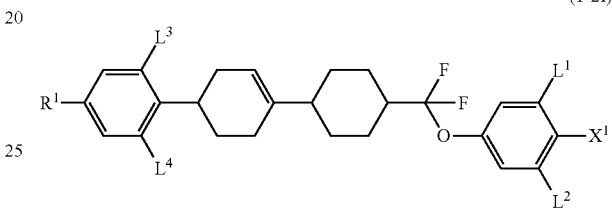
(1-2f)

wherein, in formula (1-2d), formula (1-2e) and formula (1-2f), $R^1$ is alkyl having 1 to 10 carbons, alkoxy having 1 to 10 carbons, alkenyl having 2 to 10 carbons or alkenyloxy having 2 to 10 carbons; $X^1$ is fluorine, —$CF_3$ or —$OCF_3$; and $L^1$, $L^2$, $L^3$ and $L^4$ are independently hydrogen or fluorine.

9. The compound according to claim 1, represented by any one of formula (1-1a), formula (1-1b) and formula (1-1c):

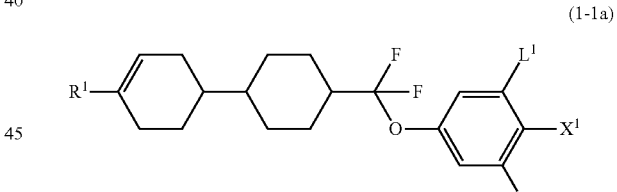
(1-1a)

(1-1b)

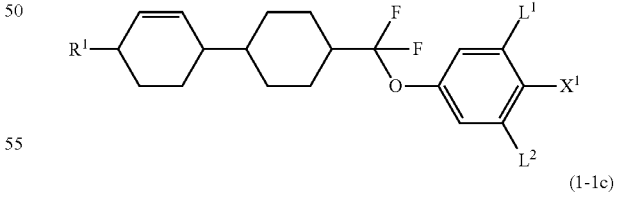

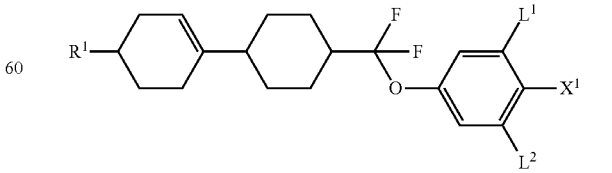
(1-1c)

wherein, in formula (1-1a), formula (1-1b) and formula (1-1c), $R^1$ is alkyl having 1 to 10 carbons, alkoxy having 1 to 10 carbons, alkenyl having 2 to 10 carbons or alkenyloxy having 2 to 10 carbons; $X^1$ is fluorine, —$CF_3$ or —$OCF_3$; and $L^1$ and $L^2$ are independently hydrogen or fluorine.

10. A liquid crystal composition, containing at least one compound according to claim 1.

11. The liquid crystal composition according to claim 10, further containing at least one compound selected from the group of compounds represented by formulas (2) to (4):

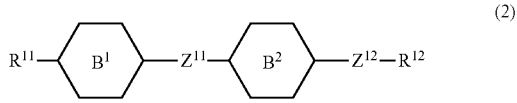
(2)

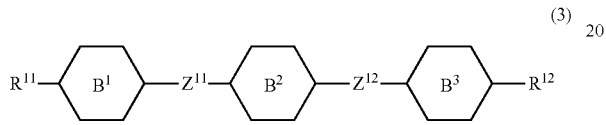
(3)

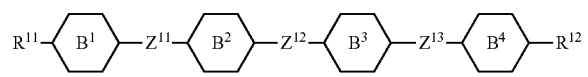
(4)

wherein, in formulas (2) to (4),
$R^{11}$ and $R^{12}$ are independently alkyl having 1 to 10 carbons or alkenyl having 2 to 10 carbons, and in $R^{11}$ and $R^{12}$, at least one piece of —$CH_2$— may be replaced by —O—, and at least one piece of hydrogen may be replaced by fluorine;
ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and
$Z^{11}$, $Z^{12}$ and $Z^{13}$ are independently a single bond, —$CH_2CH_2$—, —CH=CH—, —C≡C— or —COO—.

12. The liquid crystal composition according to claim 10, further containing at least one compound selected from the group of compounds represented by formulas (5) to (7):

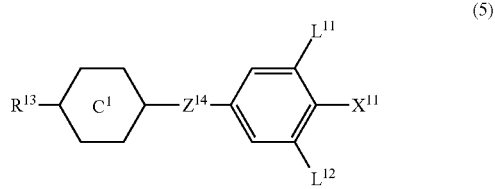
(5)

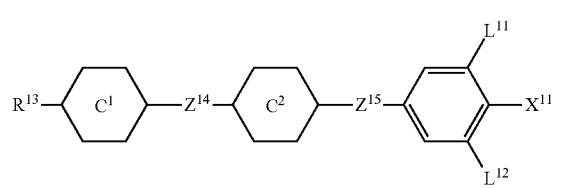
(6)

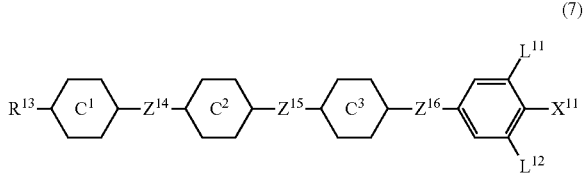
(7)

wherein, in formulas (5) to (7),
$R^{13}$ is alkyl having 1 to 10 carbons or alkenyl having 2 to 10 carbons, and in $R^{13}$, at least one piece of —$CH_2$— may be replaced by —O—, and at least one piece of hydrogen may be replaced by fluorine;
$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;
ring $C^1$, ring $C^2$ and ring $C^3$ are independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;
$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and
$L^{11}$ and $L^{12}$ are independently hydrogen or fluorine.

13. The liquid crystal composition according to claim 10, further containing at least one compound selected from the group of compounds represented by formula (8):

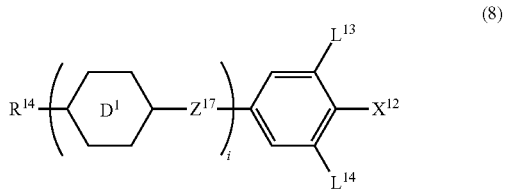
(8)

wherein, in formula (8),
$R^{14}$ is alkyl having 1 to 10 carbons or alkenyl having 2 to 10 carbons, and in $R^{14}$, at least one piece of —$CH_2$— may be replaced by —O—, and at least one piece of hydrogen may be replaced by fluorine;
$X^{12}$ is —C≡N or —C≡C—C≡N;
ring $D^1$ is 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl, and when a plurality of rings $D^1$ exist, rings $D^1$ may be identical or different;
$Z^{17}$ is independently a single bond, —$CH_2CH_2$—, —C≡C—, —COO—, —$CF_2O$—, —$OCF_2$— or —$CH_2O$—, and when a plurality of $Z^{17}$ exist, $Z^{17}$ may be identical or different;
$L^{13}$ and $L^{14}$ are independently hydrogen or fluorine; and
$i$ is 1, 2, 3 or 4.

14. The liquid crystal composition according to claim 10, further containing at least one compound selected from the group of compounds represented by formulas (9) to (15):

(9)
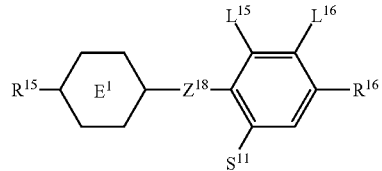

(10)
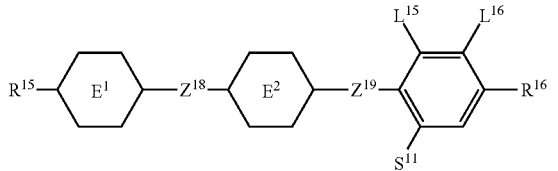

(11)
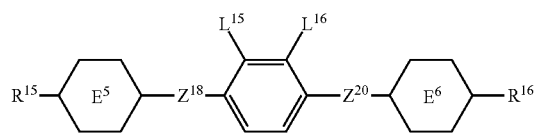

(12)
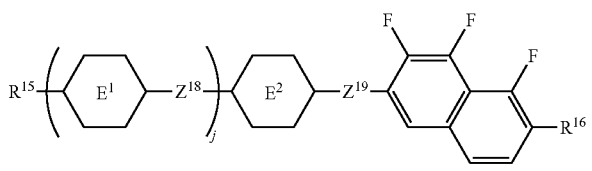

(13)
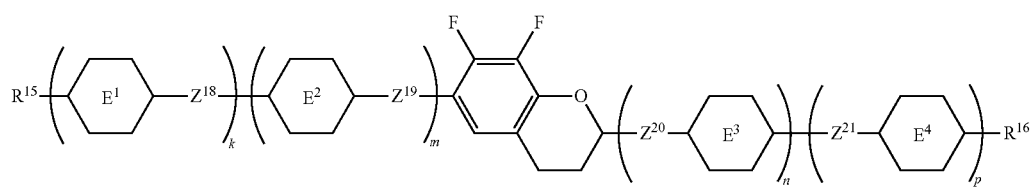

(14)
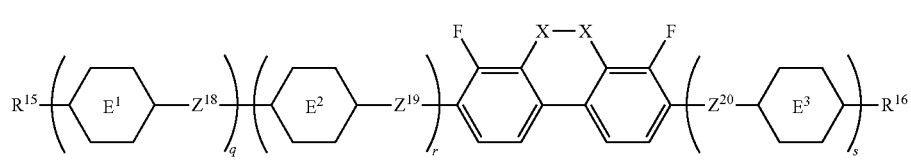

(15)
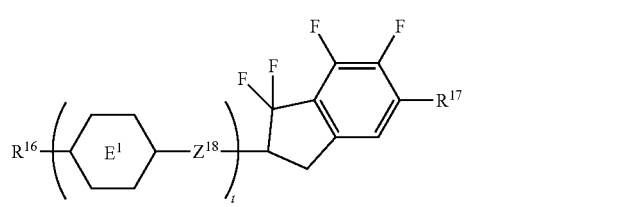

wherein, in formulas (9) to (15), $R^{15}$ and $R^{16}$ are independently alkyl having 1 to 10 carbons or alkenyl having 2 to 10 carbons, and in $R^{15}$ or $R^{16}$, at least one piece of —$CH_2$— may be replaced by —O—, and at least one piece of hydrogen may be replaced by fluorine;

$R^{17}$ is hydrogen, fluorine, alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

ring $E^1$, ring $E^2$, ring $E^3$ and ring $E^4$ are independently 1,4-cyclohexylene, 1,4-cyclohexenylene, 1,4-phenylene in which at least one piece of hydrogen may be replaced by fluorine, tetrahydropyran-2,5-diyl or decahydronaphthalene-2,6-diyl, and when a plurality of ring $E^1$, ring $E^2$, ring $E^3$ and ring $E^4$ exist, respectively, ring $E^1$, ring $E^2$, ring $E^3$ and ring $E^4$ may be identical or different;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —$CH_2CH_2$—, —COO—, —$CH_2O$—, —$OCF_2$— or —$OCF_2CH_2CH_2$—, and when a plurality of $Z^{18}$, $Z^{19}$, $Z^{20}$ and $Z^{21}$ exist, respectively, $Z^{18}$, $Z^{19}$, $Z^{20}$ and $Z^{21}$ may be identical or different;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3, and t is 1, 2 or 3.

15. The liquid crystal composition according to claim 10, further containing at least one additive selected from the group of a polymerizable compound, a polymerization initiator, a polymerization inhibitor, an optically active compound, an antioxidant, an ultraviolet light absorber, a light stabilizer, a heat stabilizer, a dye and an antifoaming agent.

16. A liquid crystal display device, including the liquid crystal composition according to claim 10.

* * * * *